United States Patent [19]
Kucherlapati et al.

[11] Patent Number: 6,114,598
[45] Date of Patent: Sep. 5, 2000

[54] GENERATION OF XENOGENEIC ANTIBODIES

[75] Inventors: Raju Kucherlapati, Darien, Conn.; Aya Jakobovits, Menlo Park, Calif.; Sue Kalpholz, Stanford, Calif.; Daniel G. Brenner, Redwood City, Calif.; Daniel J. Capon, Hillsborough, Calif.

[73] Assignee: Abgenix, Inc., Fremont, Calif.

[21] Appl. No.: 08/464,582

[22] Filed: Jun. 5, 1995

Related U.S. Application Data

[62] Continuation of application No. 08/031,801, Mar. 15, 1993, which is a continuation-in-part of application No. 07/919,297, filed as application No. PCT/US91/00245, Jan. 11, 1991, abandoned, which is a continuation-in-part of application No. 07/610,515, Nov. 8, 1990, abandoned, which is a continuation-in-part of application No. 07/466,008, Jan. 12, 1990, abandoned.

[51] Int. Cl.[7] .............................. C12N 5/10; C12N 15/79; A61K 48/00
[52] U.S. Cl. .................................. 800/18; 800/18; 800/3; 800/4; 800/22; 800/25; 435/325; 435/354
[58] Field of Search .............................. 800/2, 3, 4, 18, 800/22, 25; 435/172.5, 325, 354, 326, 328, 375

[56] References Cited

U.S. PATENT DOCUMENTS

| | | | |
|---|---|---|---|
| 4,950,599 | 8/1990 | Bertling | 435/456 |
| 4,959,313 | 9/1990 | Taketo | 435/69.1 |
| 5,204,244 | 4/1993 | Fell et al. | 435/68 |
| 5,545,806 | 8/1996 | Lonberg et al. | 800/13 |
| 5,545,807 | 8/1996 | Surani et al. | 800/13 |
| 5,591,669 | 1/1997 | Krimpenfort | 800/2 |

FOREIGN PATENT DOCUMENTS

| | | |
|---|---|---|
| 0 298 807 A1 | 6/1988 | European Pat. Off. |
| 0 459 372 A3 | 5/1991 | European Pat. Off. |
| WO 91/10741 | of 0000 | WIPO |
| WO 92/03918 | 3/1992 | WIPO |
| WO 93/05165 | 3/1993 | WIPO |
| WO 94/00569 | 1/1994 | WIPO |
| WO 94/02602 | 2/1994 | WIPO |

OTHER PUBLICATIONS

Dorfman, Nickolas A., 1985, "The Optimal Technological Approach to the Development of Human Hybridomas," *Journal of Biological Response Modifiers* 4:213–239.
Taggart et al., 1983, "Stable Antibody–Producing Murine Hybridomas," *Science* 219:1228–1230.
Thomas and Capecchi (1987) *Cell* 51:503–512.
Pachnis, et al. (1990) P.N.A.S. 87:5109–5113.
Traver, et al. (1989) P.N.A.S. 86:5898–5902.
Joyner, et al. (1989) *Nature* 338:153–155.
Blankenstein and Kruwinkel (1987) *Eur. J. Imm.* 17:1351–1357.
Tucker, et al. (1981) P.N.A.S. 78:7684–7688.
Sakano, et al. (1981) *Nature* 290:562–565.
Brownstein, et al. (1989) *Science* 244:1348–1351.
Garza, et al. (1989) *Science* 246:641–646.
Burke, et al. (1987) *Science* 236:806–812.
Berman, et al. (1988) *EMBO J.* 7:727–738.
Koller adn Smithies (1989) P.N.A.S. 86:8932–8935.
Miller, J. et al. *Nature* (1982) 295:428–430.
Shin et al., "Physical map of the 3' region of the human immunoglobulin heavy chain locus: clustering of autoantibody–related variable segments in one haplotype" (1991) *EMBO* 10:3641–3645.
Yamaura et al., "Cell–Type–Specific and Regulated Expression of a Human γ1 Heavy–Chain Immunoglobulin Gene in Transgenic Mice", *Proc. Natl. Acad. Sci., USA* 83:2152–2156 (1986).
Ayares et al., "Sequence Homology Requirements for Intermolecular Recombination in Mammalian Cells", *Proc. Natl. Acad. Sci. USA* 83:5199–5203 (1986).
Brinster et al., "Introns Increase Transcriptional Efficiency in Transgenic Mice", *Proc. Natl. Acad. Sci., USA* 85:836–840 (1988).
Kucherlapalati, R., "Homologous Recombination in Mammalian Somatic Cells", *Prog. Nucleic Acid Res. Mol. Biol.* 36:301–310 (1989).
Shimizu et al., "Immunoglobulin Double–Isotype Expression by Trans–mRNA in a Human Immunoglobulin Transgenic Mouse", *Proc. Natl. Acad. Sci., USA* 86:8020–8023 (1989).
Thomas, et al., "Site–Directed Mutagenesis by Gene Targeting in Mouse Embryo–Derived Stem Cells" (1987) *Cell* 51:503–512.
Koller, et al., "Inactivating the $\beta_2$–microglobulin locus in mouse embryonic stem cells by homologous recombination" (1989) *Proc. Nat'l. Acad. Sci.* 86:8932–8935.
Berman, et al., "Content and organization of the human Ig $V_H$ locus: definition of three new $V_H$ families and linkage to the Ig $C_H$ locus" (1988) *EMBO J.* 7:727–738.
Burke, et al., "Cloning of Large Segments of Exogenous DNA into Yeast by Means of Artificial Chromosome Vectors" (1987) *Science* 236:806–812.
Garza, et al., "Mapping the Drosophila Genome with Yeast Artificial Chromosomes" (1989) *Science* 246:641–646.

(List continued on next page.)

*Primary Examiner*—Brian R. Stanton
*Assistant Examiner*—Karen M. Hauda
*Attorney, Agent, or Firm*—Fish & Neave; James F. Haley, Jr., Esq; Jane T. Gunnison, Esq

[57] ABSTRACT

The subject invention provides non-human mammalian hosts characterized by inactivated endogenous Ig loci and functional human Ig loci for response to an immunogen to produce human antibodies or analogs thereof. The hosts are produced by multiple genetic modifications of embryonic cells in conjunction with breeding. Different strategies are employed for recombination of the human loci randomly or at analogous host loci. Chimeric and transgenic mammals, particularly mice, are provided, having stably integrated large, xenogeneic DNA segments. The segments are introduced by fusion with yeast spheroplasts comprising yeast artificial chromosomes (YACs) which include the xenogeneic DNA segments and a selective marker such as HPRT, and embryonic stem cells.

5 Claims, 27 Drawing Sheets

OTHER PUBLICATIONS

Brownstein, et al., "Isolation of Single–Copy Human Genes from a Library of Yeast Artificial Chromosome Clones" (1989) *Science 244*:1348–1351.

Sakano, et al., "Identification and nucleotide sequence of a diversity DNA segment (D) of immunoglobulin heavy–chain genes" (1981) *Nature 290*:562–565.

Tucker, et al., "Mouse IgA heavy chain gene sequence: Implications for evolution of immunoglobulin hinge exons" (1981) *Proc. Nat'l. Acad. Sci. 78*:7684–7688.

Blankenstein, et al., "Immunoglobulin $V_H$ region genes of the mouse are organized in overlapping clusters" (1987) *Eur. J. Immunol. 17*:1351–1357.

Joyner, et al., "Production of a mutation in mouse En–2 gene by homologous recombination in embryonic stem cells" (1989) *Nature 338*:153–155.

Traver, et al., "Rapid screening of a human genomic library in yeast artificial chromosomes for single–copy sequences" (1989) *Proc. Nat'l. Acad. Sci. 86*:5898–5902.

Pachnis, et al., "Transfer of a yeast artificial chromosomes carrying human DNA from *Saccharomyces cerevisiae* into mammalian cells" (1990) *Pro. Nat'l. Acad. Sci. 87*:5109–5113.

Brüggemann et al., "A repertoire of monoclonal antibodies with human heavy chains from transgenic mice" (1989) *Proc. Nat'l. Acad. Sci. 86*:6709–6713.

Brüggemann et al., "Construction, Function and Immunogenicity of Recombinant Monoclonal Antibodies" (1990) *Behring Inst. Mitt. 87*:21–24.

Brüggemann et al., "Human antibody production in transgenic mice: expression from 100 kb of the human IgH locus" (1991) *Eur. J. Immunolog. 21*:1323–1326.

Albertsen et al., "Construction and characterization of a yeast artificial chromosome library containing seven haploid human genome equivalents" (1990) *Proc. Nat'l. Acad. Sci. 87*:4256–4260.

Pavan et al., "Modification and Transfer into an Embryonal Carcinoma Cell Line of a 360–Kilobase Human–Derived Yeast Artificial Chromosome" (1990) *Mol. and Cell. Biol. 10*(8):4163–4169.

Gnirke et al., "Cloning and in vivo expression of the human GART gene using yeast artificial chromosomes" (1991) *EMBO Journal 10*(7):1629–1634.

Eliceiri et al., "Stable integration and expression in mouse cells of yeast artificial chromosomes harboring human genes" (1991) *Proc. Nat'l. Acad. Sci. 88*:2179–2183.

Huxley et al., "The Human HPRT Gene on a Yeast Artificial Chromosome is Functional When Transferred to Mouse Cells by Cell Fusion" (1991) *Genomics 9*:742–750.

Mortensen et al., "Production of Homozygous Mutant ES Cells with a Single Targeting Construct" (1992) *Mol. and Cell. Biol. 12*(5):2391–2395.

Davies et al., "Targeted alterations in yeast artificial chromosomes for inter–species gene transfer" (1992) *Nucl. Acids Res. 20*:2693–2698.

Zachau, "The Human Immunoglobulin K Locus and Some of its Acrobatics" (1990) *Biol. Chem. 371*:1–6.

Matsuda et al., "Structure and physical map of 64 variable segments in the 3' 0.8–megabase region of the human immunoglobulin heavy–chain locus" (1993) *Nature Genetics 3*:88–94.

Capecchi et al., "Altering The Genome By Homologous Recombination," (1989) 244:1288–92.

Choi et al., "RNA Splicing Generates A Variant Light Chain From An Aberrantly Arranged K Gene," (1980) 286:776–779.

Doetschman et al., "Targeted Mutation Of The Hprt Gene In Mouse Embryonic Stem Cells," (1988) 85:8583–8587.

Jakobovits et al., "Germ–line Transmission and Expression of A Human–derived Yeast Artificial Chromosome," (1993) 362:252–258.

Johnson et al., "Targeting Of Nonexpressed Genes In Embryonic Stem Cells Via Homologous Recombination," (1989) 245:1234–1236.

Kucherlapati et al., "Homologous Recombination In Mammalian Somatic Cells," (1989) 36:301–310.

Mansour et al., "Disruption of the Proto–oncogene Int–2 In Mouse Embryo–derived Stem Cells: A General Strategy For Targeting Mutations To Non–selectable Genes," (1988) 336:348–352.

Max et al., "Sequences of Five Potential Recombination Sites Encoded Close To An Immunoglobulin K Constant Region Gene." (1979) 76:3450–3454.

Orkin et al., "Mutation In An Intervening Sequence Splice Junction In Man," (1981) 78:5041–5045.

Rajewski et al., "Evolutionary and Somatic Selection of the Antibody Repertoire in the Mouse," (1987) 238:1088–1094.

Ramirez–Solis et al., "Chromosome Engineering In Mice," (1995) 378:720–724.

Sakano et al., "Sequences At The Somatic Recombination Sites Of Immunoglobulin Light–chain Genes," (1979) 280:288–294.

Sakano et al., "Two Types Of Somatic Recombination Are Necessary For The Generation Of Complete Immunoglobulin Heavy–Chain Genes," (1980) 280:676–683.

Schedl et al., "Transgenic Mice Generated By Pronuclear Injection Of A Yeast Artificial Chromosome," (1992) 20:3073–3077.

Schwartzberg et al., "Germ–line Transmission Of A c–abl Mutation Produced By Targeted Gene Disruption In ES Cells," (1989) 246:799–803.

Seidman and Leder, "A Mutant Immunoglobulin Light Chain Is Formed By Aberrant DNA– and RNA–Splicing Events," (1980) 286:779–783.

Treisman et al., "Specific Transcription and RNA Splicing Defects In Five Cloned β–Thalassaemia Genes," (1983) 302:591–596.

Zjilstra et al., "Germ–line Transmission Of A Disrupted β2–Microglobulin Gene Produced By Homologous Recombination in Embryonic Stem Cells," (1989) 342:435–438.

Shenigin PNAS 86: 8020,1909.

Berna EMBO J. 7(3): 727,1988.

Pachnis PNAS 87: 5709,1990.

Huxley Genomics 9:742,1991.

Taki Science 262: 1268,1993.

Morrison Nature, 368: 812,1994.

Green Nature Genetics 7: 13,1994.

Cos declaration, submitted in 08/112848.

Hooper Nature 326: 292,1987.

Traver PNAS 86: 5898,1989.

Joyner et al.; Nature 338:153–155 (1989).

Traver et al.; Proc. Nat. Acad. Sci. USA 86:5898–5902 (1989).

Panchis et al. Proc. Nat. Acad. Sci. USA 87:5109–5113 (1990).

Bruggemann et al.; Proc. Natl. Acad. Sci. USA 86:6709–6713 (1989); A Repertoire of Monoclonal antibodies with Human Heavy Chains from Transgenic Mice.

Buttin G.; Trends in Genetics 3(8):205–206 (1987); Exogenous Ig Gene Rearrangement in Transgenic Mice: A New Strategy for Human Monocloanl Antibody Production.

Yancopoulus et al.; Science 241 1581–1583 (1988); Reconstruction of an Immune System.

Bruggemann, "A repertoire of monoclonal antibodies with human heavy chains from transgenic mice," Proc. Natl. Acad. Sci., vol. 86: 6709–6713, Sep. 1989.

Thomas et al.; Cell, vol. 51:503–512 (1987); Site–Directed Mutagenesis by Gene Targeting in Mouse Embryo–Derived Stem Cells.

Koller et al.; Proc. Natl. Acad. Sci. USA, vol. 86:8932–8935 (1989); Inactivating the $\beta_2$–microglobulin locus in mouse embryonic stem cells by homologous recombination.

Berman et al.; EMBO Journal, 7(3):727–738 (1988); Content and Organization of the human Ig $V_H$ locus: definition of three new $V_H$ families and linkage to the Ig $C_H$ locus.

Burke et al.; Science, 236:806–812 (1987); Cloning of Large Segments of Exogenous DNA into Yeast by Means of Artificial Chromosome Vectors.

Garza et al.; Science 246:641–646 (1989); Mapping the Drosphila Genome with Yeast Artificial Chromosomes.

Brownstein et al.; Science 244:1348–1351 (1989); Isolation of Single–Copy Human Genes from a Library of Yeast Artificial Chromosome Clones.

Sakano et al.; Nature 290:562–565 (1981); Identification and Nucleotide Sequence of a Diversity DNA Segment (D) of Immunoglobulin Heavy–Chain Genes.

Tucker et al.; Proc. Natl. Acad. Sci. USA 78(12):7684–7688 (1981); Mouse IgA Heavy Chain Gene Sequence: Implications for Evolution of Immunoglobulin Hinge Exons.

Blankenstein and Kruwinkel; Eur. J. Immunol. 17:1351–1357 (1987).

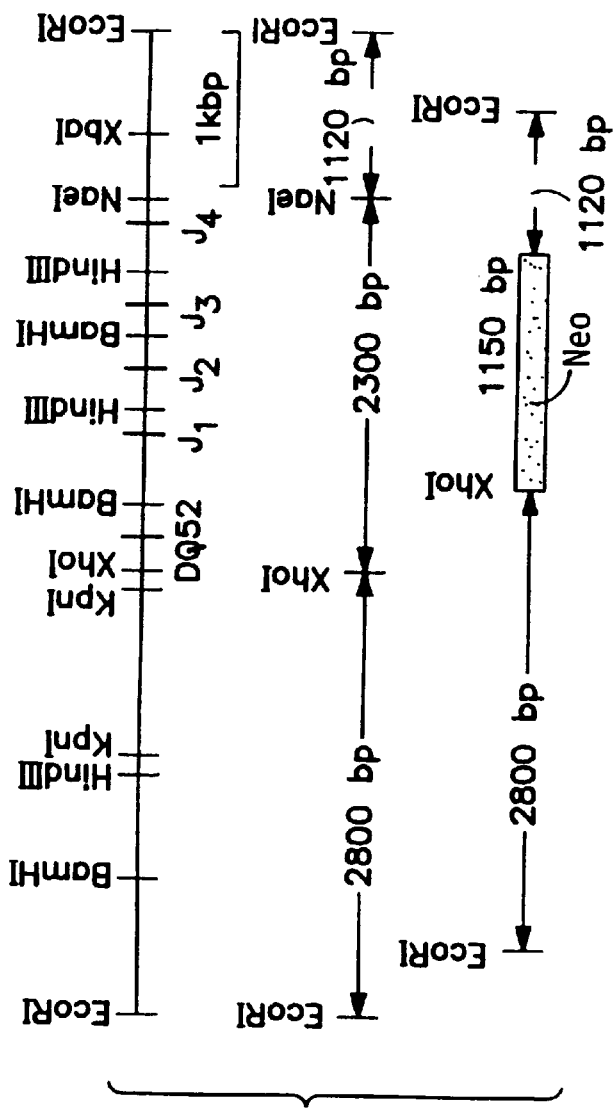
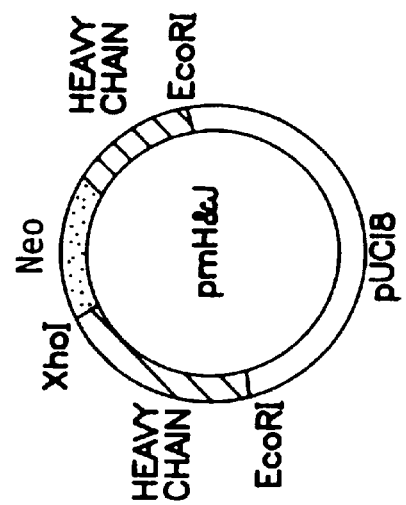
FIG. 2A
FIG. 2B a allotype b allotype

SOUTHERN ANALYSIS OF LIGHT CHAIN Cκ TARGETED E14-1 CELLS

SCHEME A

Mouse Breeding Scheme

Cross IA.

heterozygous inactive Murine IgH
           X
heterozygous inactive Murine IgK $\frac{\text{MIgH (inactive)}}{\text{MIgH}}$  $\frac{\text{MIgK}}{\text{MIgK}}$

X $\frac{\text{MIgH}}{\text{MIgH}}$  $\frac{\text{MIgK (inactive)}}{\text{MIgK}}$
    ↓

F1 (cross I A)

$\frac{\text{MIgH (inactive)}}{\text{MIgH}}$  $\frac{\text{MIgK (inactive)}}{\text{MIgK}}$ Cross IB.

heterozygous Human IgH
           X
heterozygous Human IgK $\frac{\text{MIgH}}{\text{MIgH}}$  $\frac{\text{MIgK}}{\text{MIgK}}$  HIgH

X $\frac{\text{MIgH}}{\text{MIgH}}$  $\frac{\text{MIgK}}{\text{MIgK}}$  HIgK
    ↓

F1 (cross I B)

$\frac{\text{MIgH}}{\text{MIgH}}$  $\frac{\text{MIgK}}{\text{MIgK}}$  HIgH  HIgK Cross II.     F1 (cross I A) x F1 (cross I B)
                           ↓
       F2   Quadruple  Heterozygotes $\frac{\text{MIgH (inactive)}}{\text{MIgH}}$  $\frac{\text{MIgK (inactive)}}{\text{MIgK}}$  HIgH  HIgK Cross III.     Intercross  F2 mice
                         ↓
       F3   DOUBLE   Homozygotes $\frac{\text{MIgH (inactive)}}{\text{MIgH (inactive)}}$  $\frac{\text{MIgK (inactive)}}{\text{MIgK (inactive)}}$  HIgH  HIgK

MAMMALIAN HOST GENOTYPES

| Hetero- or Hemi-zygous Mice | Intercross Product Mice * |
|---|---|
| I. ΔmIgL/mIgL  mIgH/mIgH | ΔmIgL/ΔmIgL  mIgH/mIgH |
| II. mIgL/mIgL  ΔmIgH/mIgH | mIgL/mIgL  ΔmIgH/ΔmIgH |
| III. mIgL/mIgL  mIgH/mIgH  hIgH | mIgL/mIgL  mIgH/mIgH  hIgH/hIgH |
| IV. mIgL/mIgL  mIgH/mIgH  hIgL | mIgL/mIgL  mIgH/mIgH  hIgL/hIgL |
| V. Animal I X Animal II | ΔmIgL/ΔmIgL  ΔmIgH/ΔmIgH |
| VI. Animal III X Animal V | mIgL/mIgL  mIgH/mIgH  hIgH/hIgH and ΔmIgL/ΔmIgL  ΔmIgH/ΔmIgH  hIgH/hIgH |
| VII. Animal IV X Animal V | mIgL/mIgL  mIgH/mIgH  hIgL/hIgL and ΔmIgL/ΔmIgL  ΔmIgH/ΔmIgH  hIgL/hIgL |
| VIII. Animal VI X Animal VII | ΔmIgL/ΔmIgL  ΔmIgH/ΔmIgH  hIgL/hIgL  hIgH/hIgH and ΔmIgL/ΔmIgL  ΔmIgH/ΔmIgH  hIgL  hIgH |

FIG. 18B

IX. Animal III X Animal IV $\frac{mIgL}{mIgL}$ $\frac{mIgH}{mIgH}$ $\frac{hIgL}{hIgH}$ $\frac{hIgH}{}$ $\frac{mIgL}{mIgL}$ $\frac{mIgH}{mIgH}$ $\frac{hIgL}{hIgH}$ $\frac{hIgH}{}$ X. Animal II X Animal IX $\frac{mIgL}{mIgL}$ $\frac{\Delta mIgH}{mIgH}$ $\frac{hIgL}{hIgH}$ and $\frac{mIgL}{mIgL}$ $\frac{\Delta mIgH}{\Delta mIgH}$ $\frac{hIgL}{hIgH}$ $\frac{hIgH}{}$ XI. Animal I X Animal IX $\frac{\Delta mIgL}{mIgL}$ $\frac{mIgH}{mIgH}$ $\frac{hIgL}{hIgH}$ $\frac{hIgH}{}$ and $\frac{\Delta mIgL}{\Delta mIgL}$ $\frac{\Delta mIgH}{\Delta mIgH}$ $\frac{mIgH}{mIgH}$ $\frac{hIgL}{hIgH}$ $\frac{hIgH}{}$

*Not all possible genotypes from intercrosses are shown.

Δ = functionally inactive locus
m = mouse endogenous gene
h = human transgene
IgH = immunoglobulin heavy chain
IgL = immunoglobulin light chain

GENERATION OF XENOGENEIC ANTIBODIES

This application is a continuation of application Ser. No. 08/031,801 filed Mar. 15, 1993, now pending.

CROSS-REFERENCE TO RELATED APPLICATIONS

This application which is a continuation-in-part of application Ser. No. 07/919,297 filed Jul. 24, 1992, now abandoned, which was a continuation-in-part of application Ser. No. 07/610,515 filed Nov. 8, 1990, now abandoned, which was a continuation-in-part of application Ser. No. 07/466,008 filed Jan. 12, 1990, now abandoned, the entire disclosures of which are all incorporated herein by reference.

TECHNICAL FIELD

The field of this invention is the production of xenogeneic specific binding proteins in a viable mammalian host.

BACKGROUND

The ability to produce transgenic animals has been revolutionized with the advent of the ability to culture murine embryonic stem cells, and to introduce genetic modifications in these cells for subsequent transmission to the mouse germline. Thus one has the opportunity to modify endogenous genes to produce animal strains capable of producing novel products by introduction of foreign genes into the host, particularly human genes to produce xenogeneic binding proteins. The expression of such genes in vivo in an animal model may provide for investigation of the function of the gene, the regulation of gene expression, its processing, response to various agents and the like. In addition, animals with new phenotypes, including those that mimic a variety of diseases, may be produced. For example, there is interest in introducing a dominant mutation or complementing a recessive mutation. Depending on the particular gene, the difficulty of achieving the desired mutation will vary greatly. While some gene targets have proven to be relatively amenable to modification, other targets have proven to be extremely resistant to modification.

Because of the opportunity for generating transgenic animals, there is substantial interest in providing new procedures that increase the success of production of transgenic animals. Particularly, where one wishes to introduce large DNA fragments, encompassing hundreds of kilobases, there is substantial concern about the ability to introduce the large fragments in intact form into mammalian cells, the efficiency of integration, the functional capability of the gene(s) present on the fragment and transmission in the germline to the progeny. In addition, such procedures for introduction of large DNA fragments provide for determination of the function of large DNA fragments identified in the ongoing human genome project.

In particular, there is interest in producing xenogeneic specific binding proteins, for example human monoclonal antibodies, in small laboratory animals such as mice. Monoclonal antibodies find use in both diagnosis and therapy. Because of their ability to bind to a specific epitope, they can be uniquely used to identify molecules carrying that epitope or may be directed, by themselves or in conjunction with another moiety, to a specific site for diagnosis or therapy.

Monoclonal antibodies comprise heavy and light chains which join together to define a binding region for the epitope. Each of the chains is comprised of a variable region and a constant region. The constant region amino acid sequence is specific for a particular isotype of the antibody, as well as the host which produces the antibody.

Because of the relationship between the sequence of the constant region and the species from which the antibody is produced, the introduction of a xenogeneic antibody into the vascular system of the host can produce an immune response. Where the xenogeneic antibody is introduced repetitively, in the case of chronic diseases, it becomes impractical to administer the antibody, since it will be rapidly destroyed and may have an adverse effect. There have been, therefore, many efforts to provide a source of syngeneic or allogeneic antibodies. One technique has involved the use of recombinant DNA technology where the genes for the heavy and light chains from a host were identified and the regions encoding the constant region isolated. These regions were then joined to the variable region encoding portion of other immunoglobulin genes from another species directed to a specific epitope.

While the resulting chimeric partly xenogeneic antibody is substantially more useful than using a fully xenogeneic antibody, it still has a number of disadvantages. The identification, isolation and joining of the variable and constant regions requires substantial work. In addition, the joining of a constant region from one species to a variable region from another species may change the specificity and affinity of the variable regions, so as to lose the desired properties of the variable region. Also, there are framework and hypervariable sequences specific for a species in the variable region. These framework and hypervariable sequences may result in undesirable antigenic responses.

It would therefore be more desirable to produce allogeneic antibodies for administration to a host by immunizing the host with an immunogen of interest. For primates, particularly humans, this approach is not practical. The human antibodies which have been produced have been based on the adventitious presence of an available spleen, from a host which had been previously immunized to the epitope of interest. While human peripheral blood lymphocytes may be employed for the production of monoclonal antibodies, these have not been particularly successful in fusions and have usually led only to IgM. Moreover, it is particularly difficult to generate a human antibody response against a human protein, a desired target in many therapeutic and diagnostic applications. There is, therefore, substantial interest in finding alternative routes to the production of allogeneic antibodies for humans.

Relevant Literature

Thomas and Capecchi (1987), *Cell*, 51:503–512 and Koller and Smithies (1989), *Proc. Natl. Acad. Sci. USA*, 86:8932–8935 describe inactivating the β2-microglobulin locus by homologous recombination in embryonic stem cells. Berman et al. (1988), *EMBO J.* 7:727–738 describe the human Ig VH locus. Burke, et al. (1987), *Science*, 236:806–812 describe yeast artificial chromosome vectors. See also, Garza et al. (1989), *Science*, 246:641–646 and Brownstein et al. (1989), *Science*, 244:1348–1351. Sakano, et al., describe a diversity segment of the immunoglobulin heavy chain genes in Sakano et al. (1981), *Nature*, 290:562–565. Tucker et al. (1981), *Proc. Natl. Acad. Sci. USA*, 78:7684–7688 describe the mouse IgA heavy chain gene sequence. Blankenstein and Kruwinkel (1987), *Eur. J. Immunol.*, 17:1351–1357 describe the mouse variable heavy chain region. See also, Joyner et al. (1989), *Nature*, 338:153–155, Traver et al. (1989), *Proc. Nat. Acad. Sci. USA* 86:5898–5902, Pachnis et al. (1990), *Proc. Nat. Acad. Sci.*

USA, 87:5109–5113 and PCT application PCT/US91/00245. Bruggemann et al., *Proc. Nat. Acad. Sci. USA;* 86:6709–6713 (1989); *Behring Inst. Mitt.* 87:21–24 (1990); *Eur. J. Immunol.* 21:1323–1326 (1991), describe monoclonal antibodies with human heavy chains. Albertsen et al., *Proc. Nat. Acad. Sci. USA* 87:4256–4260 (1990), describe the construction of a library of yeast artificial chromosomes containing human DNA fragments. Yeast artificial chromosome vectors are described by Burke et al., *Science* 236:806–812 (1987). Pavan et al., *Mol. and Cell. Biol.* 10(8):4163–4169 (1990) describe the introduction of a neomycin resistance cassette into the human-derived insert of a yeast artificial chromosomes using homologous recombination and transfer into an embryonal carcinoma cell line using polyethylene glycol-mediated spheroplast fusion. Pachnis et al., *Proc. Nat. Acad. Sci. USA* 87:5109–5113 (1990), and Gnirke et al., *EMBO Journal* 10(7):1629–1634 (1991), describe the transfer of a yeast artificial chromosome carrying human DNA into mammalian cells. Eliceiri et al., *Proc. Nat. Acad.USA* 88:2179–2183 (1991), describe the expression in mouse cells of yeast artificial chromosomes containing human genes. Huxley et al., *Genomics* 9:742–750 (1991) describe the expression in mouse cells of yeast artificial chromosomes containing the human HPRT gene. Mortensen et al., *Mol. and Cell. Biol.* 12(5):2391–2395 (1992) describe the use of high concentrations of G418 to grow heterozygous embryonic stem cells for selection of homozygous mutationally altered cells. Yeast protoplast fusion with mouse fibroblasts is described by Traver et al., *Proc. Nat. Acad. Sci. USA* 86:5898–5902 (1989) and Pachnis et al., *Proc. Nat. Acad. Sci. USA* 87:5109–5113 (1990). Davies et al., *Nucl. Acids Res.* 20:2693–2698 (1992) describe targeted alterations in YACs. Zachau, *Biol. Chem.* 371:1–6 (1990) describes the human immunoglobulin light (kappa) (IgK) locus; Matsuda et al., *Nature Genetics* 3:88–94 (1993) and Shin et al., *EMBO* 10:3641–3645 (1991) describe the cloning of the human immunoglobulin heavy (IgH) locus in YACs.

SUMMARY OF THE INVENTION

Xenogeneic specific binding proteins are produced in a non-human viable host by immunization of the host with an appropriate immunogen.

A preferred non-human host is characterized by: (1) being incapable of producing endogenous immunoglobulin heavy chain; (2) being substantially incapable of producing endogenous immunoglobulin light chains; and (3) capable of producing xenogeneic immunoglobulin light and heavy chains to produce a xenogeneic immunoglobulin or immunoglobulin analog. Thus, the host may have an entire endogenous immunoglobulin locus substituted by a portion of, or an entire, xenogeneic immunoglobulin locus, or may have a xenogeneic immunoglobulin locus inserted into a chromosome of the host cell and an inactivated endogenous immunoglobulin region. These various alternatives will be achieved, at least in part, by employing homologous recombination for inactivation or replacement at the immunoglobulin loci for the heavy and light chains.

Additionally, novel methods are provided for introducing large segments of xenogeneic DNA of at least 100 kb, particularly human DNA, into host animals, particularly mice, by introducing a yeast artificial chromosome (YAC) containing a xenogeneic DNA segment of at least 100 kb, into an embryonic stem cell for integration into the genome of the stem cell, selection of stem cells comprising the integrated YAC by means of a marker present in the YAC, introduction of the YAC-containing ES cells into embryos and generation of chimeric mice from the embryos. The chimeric animals may be mated to provide animals that are heterozygous for the YAC. The heterozygous animals may be mated to generate progeny homozygous for the integrated YAC.

DESCRIPTION OF THE DRAWINGS

FIGS. 2A–C is a diagram of the DNA restriction map for the plasmid pmHδJ and the targeted mouse heavy chain J genes, as described in Example II, infra.

FIG. 9 is a diagram of the construction of vectors for inactivating the kappa light chain J and constant regions as described in Example IV, infra.

FIG. 17 is a diagram of a mouse breeding scheme, as described in Example VIII, infra.

FIG. 18 depicts the genotypes of some of the host animals produced by the methods of the invention.

DESCRIPTION OF SPECIFIC EMBODIMENTS

Figure 1A:
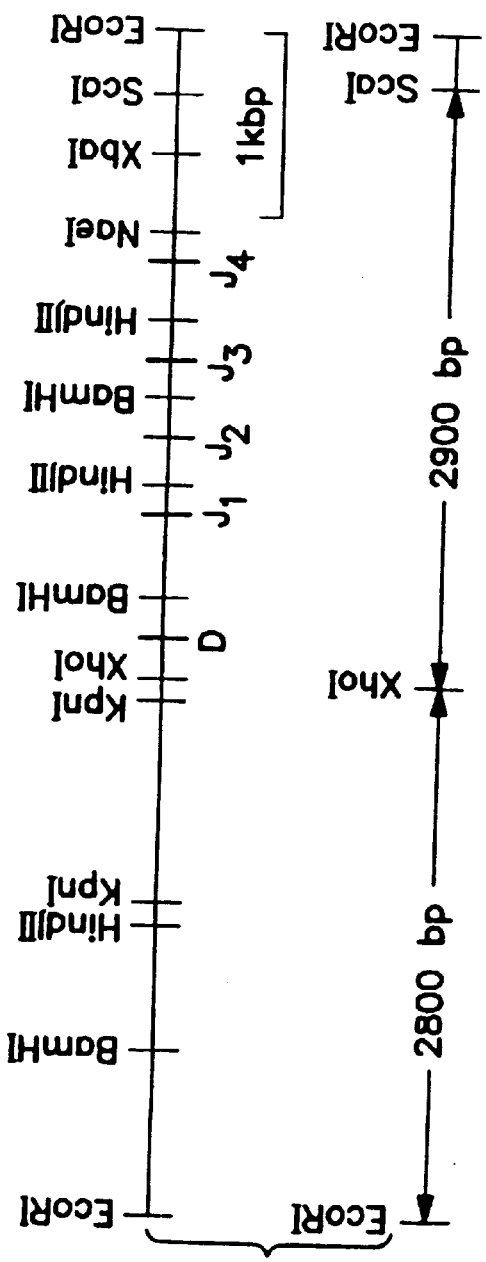
FIGS. 1A & B is a diagram of the inactivation vector for the mouse heavy chain J region, as described in Example I, infra.

Novel transgenic non-human hosts, particularly mammalian hosts, usually murine, are provided, where the host is capable of mounting an immune response to an immunogen, where the response produces antibodies having xenogeneic, particularly primate, and more particularly human, constant and/or variable regions or such other effector peptide sequences of interest. By "transgenic" is meant an animal that contains a genetically engineered modification, particularly, as to this invention, the introduction of a human immunoglobulin gene, in all of its cells. The hosts are characterized by being capable of producing xenogeneic immunoglobulins or analogs thereof as a result of inactivation of the endogenous immunoglobulin subunit encoding loci and introduction of xenogeneic DNA, for example DNA encoding human immunoglobulin. The modifications may retain at least a portion of the xenogeneic constant regions which provide for assembly of the variable region binding site bonded at the C-terminus to a functional peptide. The functional peptide may take many forms or conformations and may serve as an enzyme, growth factor, binding protein, ligand, cytokine, effector protein, chelating proteins, etc. The antibodies may be of any isotype, e.g., IgA, D, E, G or M or subtypes within the isotype.

In a first strategy, as individual steps, the xenogeneic, e.g. human, heavy and light chain immunoglobulin genes are introduced into the host germ line (e.g. sperm or oocytes) and in separate steps the corresponding host genes are rendered non-functional by inactivation using homologous recombination. Human heavy and light chain immunoglobulin genes are reconstructed in an appropriate eukaryotic or prokaryotic microorganism and the resulting DNA fragments can be introduced into the appropriate host, for example into the pronuclei of fertilized mouse oocytes or embryonic stem cells. Inactivation of the endogenous host immunoglobulin loci is achieved by targeted disruption of the appropriate loci by homologous recombination in the host cells, particularly embryonic stem cells or pronuclei of fertilized mouse oocytes. The targeted disruption can involve introduction of a lesion or deletion in the target locus, or deletion within the target locus accompanied by insertion into the locus, for example, insertion of a selectable marker. In the case of embryonic stem cells, chimeric animals are generated which are derived in part from the modified embryonic stem cells and are capable of transmitting the genetic modifications through the germ line. The mating of hosts with introduced human immunoglobulin loci to strains with inactivated endogenous loci will yield animals whose antibody production is purely xenogeneic, e.g. human.

In a second, alternative strategy, at least portions of the human heavy and light chain immunoglobulin loci are used to directly replace the corresponding endogenous immunoglobulin loci by homologous recombination in embryonic stem cells. This results in simultaneous inactivation and replacement of the endogenous immunoglobulin. This is followed by the generation of chimeric animals in which the embryonic stem cell-derived cells can contribute to the germ line.

These strategies are based on the known organization of the immunoglobulin chain loci in a number of animals, since the organization, relative location of exons encoding individual domains, and location of splice sites and transcriptional elements is understood to varying degrees. In the human, the immunoglobulin heavy chain ($IgH_{hu}$) locus is located on chromosome 14. In the 5'-3' direction of transcription, the locus comprises a large cluster of variable region genes ($V_H$), the diversity (D) region genes, followed by the joining ($J_H$) region genes and the constant ($C_H$) gene cluster. The size of the locus is estimated to be about from 1,500 to about 2,500 kilobases (kb). During B-cell development, discontinuous gene segments from the germ line IgH locus are juxtaposed by means of a physical rearrangement of the DNA. In order for a functional heavy chain Ig polypeptide to be produced, three discontinuous DNA segments, from the $V_H$, D, and $J_H$ regions must be joined in a specific sequential fashion; first D to $J_H$ then $V_H$ to $DJ_H$, generating the functional unit $V_H DJ_H$. Once a $V_H DJ_H$ has been formed, specific heavy chains are produced following transcription of the Ig locus, utilizing as a template the specific $V_H DJ_H C_H$ unit comprising exons and introns.

There are two loci for immunoglobulin light chains (IgL), the kappa locus on human chromosome 2 and the lambda locus on human chromosome 22. The organization of the IgL loci is similar to that of the IgH locus, except that the D region is not present. Following IgH rearrangement, rearrangement of a light chain locus is similarly accomplished by $V_L$ to $J_L$ joining of the kappa or lambda chain. The sizes of the lambda and kappa loci are each approximately 1000 kb to 2000 kb. Expression of rearranged IgH and an Igκ or Igλ light chain in a particular B-cell allows for the generation of antibody molecules.

In order to isolate, clone and transfer the $IgH_{hu}$ locus, a yeast artificial chromosome or "YAC" may be employed. A YAC carrying the xenogeneic DNA may be introduced into ES cells or oocytes by a variety of methods, including yeast spheroplast: ES cell fusion, microinjection and lipofection. The YAC will integrate randomly (i.e. non-homologously) into the host genome. If yeast spheroplast:ES cell fusion is employed to introduce a YAC carrying xenogeneic DNA into ES host cells, then two or more YACs in a single yeast host cell may be introduced simultaneously into the same host ES cell. The advantage of this approach is that multiple YACs each containing xenogeneic DNA, for example human heavy and light chain immunoglobulin loci, can be introduced into a single chromosome in a host cell. This eliminates the need for breeding of animals containing individual human Ig genes in order to generate a host capable of producing fully human immunoglobulins. For example, a strain of yeast containing a single YAC is targeted with a vector such as PLUTO (described infra) to introduce a mammalian selectable marker such as HPRT, and a yeast selectable marker such as LYS2 into an arm of the YAC. Chromosomal DNA from the targeted strain is then used to transform a second, usually haploid, lys2 mutant yeast strain containing a second, different YAC. Lys+ colonies are then analyzed by pulsed-field gel electrophoresis (PFGE) to identify clones harboring the two YACs and to confirm that they are unaltered in size. Additional YACs with different selectable markers, for example ADE2 (if the host is an ade2 mutant), can subsequently be added by transformation. Alternatively, a YAC-containing strain of yeast is targeted with a vector such as pLUTO to introduce a mammalian selectable marker (e.g. HPRT), as above, and then mated to a second YAC-containing strain of opposite mating type. The presence of the two YACs is then confirmed in the diploid yeast cells as described above. The diploid yeast strain is used directly for fusion or put through meiosis and ascosporogenesis (sporulation) using standard procedures. The meiotic products are then screened to identify a haploid clone containing the two YACs. With either approach described above, the second YAC can be targeted with HPRT or another selectable marker prior to introduction of the first YAC. Also, if each YAC contains a different yeast selectable marker, maintenance of both YACS during strain propagation may be genetically selected. Fusion with ES cells is then carried out in the same manner as with yeast cells containing a single YAC. Because many yeast chromosomes may integrate along with the YAC, it is expected that a substantial portion of ES clones expressing the mammalian selectable marker present in one YAC (e.g. HATR clones if the YAC marker is HPRT, and the ES cells are HPRT-), will have integrated both YACS. Methods such as Southern analysis and/or PCR may be used to identify such clones, and Southern analysis employing pulsed-field gel electrophoresis used to characterize the extent of YAC integration.

The entire $IgH^{hu}$ locus can be contained within one or a few YAC clones along with a mammalian marker such as Neo, HPRT, GPT, β-gal, etc. The same is true for the Ig light chain loci. Reconstitution of intact germ line Ig loci by homologous recombination between YACs with overlapping regions of homology can be achieved in yeast. In this manner, the isolation of DNA fragments encoding the human Ig chain is obtained. Alternatively, one can directly clone an intact germline locus in a single YAC.

In order to obtain a broad spectrum of high affinity antibodies, it is not necessary that one include the entire V region. Various V region gene families are interspersed within the V region cluster in humans. Thus, by obtaining a subset of the known V region genes of the human heavy and light chain Ig loci (Berman et al., EMBO J. (1988) 7:727–738) rather than the entire complement of V regions, the transgenic host may be immunized and be capable of mounting a strong immune response and provide high affinity antibodies. In this manner, relatively small DNA fragments of the chromosome may be employed. For example, a reported 670 kb fragment of the $Ig_{Hu}$ locus is contained on a NotI—NotI restriction fragment, which would serve to provide a variety of V regions (Berman et al., supra). Increased diversity is also provided by recombination with the various D and J regions and somatic mutation.

To render the host immunoglobulin loci non-functional, homologous recombination may be employed, where DNA is introduced at the endogenous host immunoglobulin heavy chain and light chain loci which inhibits the production of endogenous immunoglobulin. Because there are two heavy chain alleles and two light chain loci, kappa and lambda, each with two alleles, although one may choose to ignore the lambda loci, there will have to be multiple transformations which result in inactivation of each of the alleles. Homologous recombination may be employed to functionally inactivate each of the loci, by introduction of the homologous DNA via a construct that can disrupt or delete the target locus into embryonic stem cells, followed by introduction of the modified cells into recipient blastocysts. Subsequent breeding allows for germ- line transmission of the inactivated locus. One can therefore choose to breed heterozygous offspring and select for homozygous offspring from the heterozygous parents.

In the second, alternative strategy described above, the number of steps may be reduced by providing at least a fragment of the human immunoglobulin locus within the construct used for homologous recombination with the analogous endogenous immunoglobulin, so that the human locus is substituted for at least a part of the host immunoglobulin locus, with resulting inactivation of the host immunoglobulin subunit locus. Of particular interest is the use of transformation for a single inactivation, followed by breeding of the heterozygous offspring to produce a homozygous offspring. Where the human locus is employed for substitution or insertion into the host locus for inactivation, the number of transformations may be limited to three transformations and as already indicated, one may choose to ignore the less used locus and limit the transformations to two transformations. Alternatively, one may choose to provide for inactivation as a separate step for each locus, employing embryonic stem cells from offspring which have previously had one or more loci inactivated. In the event that only transformation is used and the human locus is integrated into the host genome in random fashion, a total of eight or more transformations may be required.

For inactivation, any lesion in the target locus resulting in the prevention of expression of an immunoglobulin subunit of that locus may be employed. Thus, the lesion may be in a region comprising enhancers, e.g., a 5' or 3' enhancer, or intron, in the V, J or C regions, and with the heavy chain, the opportunity exists in the D region, or combinations thereof. The important factor is that Ig germ line gene rearrangement is inhibited, or a functional message encoding the enodgenous immunoglobulin cannot be produced, either due to failure of transcription, failure of processing of the message, or the like. Such a lesion may take the form of a deletion in the target gene, an insertion of a foreign gene, a combination of an insertion and deletion, or a replacement using xenogeneic sequences with or without introduction of a deletion in the endogenous gene.

Preferably, when one is interested in inactivating the immunoglobulin subunit locus, the lesion will be introduced into one or more of the exons contained in the immunoglobulin subunit locus, for example in the constant or J region of the locus. Thus, one produces a targeting construct which lacks functional exons in this region and may comprise the sequences adjacent to and upstream and/or downstream from the J and/or C region or comprises all or part of the region with an inactivating insertion in the J or C exons. The insertion may be 50 bp or more, where such an insertion results in disruption of formation of a functional mRNA. Desirably, usually at least about 75% of the exon sequence, preferably at least about 90% of the exon sequence, is deleted.

Desirably, a marker gene is used in the targeting construct to replace the deleted sequences. Various markers may be employed, particularly those which allow for positive selection. Of particular interest is the use of G418 resistance, resulting from expression of the gene for neomycin phosphotransferase ("neo").

In the targeting construct, upstream and/or downstream from the target gene, may be a gene which provides for identification of whether a homologous double crossover has occurred (negative selection). For this purpose, the Herpes simplex virus thymidine kinase gene may be employed, since cells expressing the thymidine kinase gene may be killed by the use of nucleoside analogs such as acyclovir or gancyclovir, by their cytotoxic effects on cells that contain a functional HSV-tk (Mansour et al., *Nature* 336:348–352 (1988)). The absence of sensitivity to these nucleoside analogs indicates the absence of the HSV-thymidine kinase gene and, therefore, where homologous recombination has occurred, that a double crossover has also occurred.

While the presence of the marker gene in the genome will indicate that integration has occurred, it will still be necessary to determine whether homologous integration has occurred. This can be achieved in a number of ways. For the most part, DNA analysis by Southern blot hybridization will be employed to establish the location of the integration. By employing probes for the insert and the sequences at the 5' and 3' regions flanking the region where homologous integration would occur, one can demonstrate that homologous targeting has occurred.

PCR may also be used with advantage in detecting the presence of homologous recombination. PCR primers may be used which are complementary to a sequence within the targeting construct and complementary to a sequence outside the construct and at the target locus. In this way, one can only obtain DNA molecules having both the primers present in the complementary strands if homologous recombination has occurred. By demonstrating the expected size fragments, e.g. using Southern blot analysis, the occurrence of homologous recombination is supported.

The targeting construct may further include a replication system which is functional in the host cell. For the most part, these replication systems will involve viral replication systems, such as Simian virus 40, Epstein-Barr virus, polyoma virus, papilloma virus, and the like. Various transcriptional initiation systems may be employed, either from viruses or from mammalian genes, such as SV40, metallathionein-I and II genes, β-actin gene, adenovirus early and late genes, phosphoglycerate kinase gene, RNA polymerase II gene, or the like. In addition to promoters, wild-type enhancers may be employed to further enhance the expression of the marker gene.

In preparing the targeting constructs for homologous recombination, a replication system for procaryotes, particularly *E. coli*, may be included for preparing the targeting construct, subcloning after each manipulation, analysis such as restriction mapping or sequencing, expansion and isolation of the desired sequence. In the case of the replacement strategy, where the xenogeneic DNA insert is large, generally exceeding about 50 kbp, usually exceeding 100 kbp, and usually not more than about 1000 kbp, a yeast artificial chromosome (YAC) may be used for cloning of the targeting construct.

Once a targeting construct has been prepared and any undesirable sequences removed, e.g., procaryotic sequences, the construct may now be introduced into the target cell, for example an ES cell. Any convenient technique for introducing the DNA into the target cells may be employed. Techniques include protoplast fusion, e.g. yeast spheroplast:cell fusion, lipofection, electroporation, calcium phosphate-mediated DNA transfer or direct microinjection.

After transformation or transfection of the target cells, target cells may be selected by means of positive and/or negative markers, as previously indicated, neomycin resistance and acyclovir or gancyclovir resistance. Those cells which show the desired phenotype may then be further analyzed by restriction analysis, electrophoresis, Southern analysis, PCR, or the like. By identifying fragments which show the presence of the lesion(s) at the target locus, one can identify cells in which homologous recombination has occurred to inactivate a copy of the target locus.

The above described process may be performed first to inactivate a heavy chain locus in an embryonic stem cell whereby the cells are microinjected into host blastocysts which develop into a chimeric animal. The chimeric animals are bred to obtain heterozygous hosts. Then, by breeding of the heterozygous hosts, a homozygous host may be obtained or embryonic stem cells may be isolated and transformed to inactivate the second IgH locus, and the process repeated until all the desired loci have been inactivated. Alternatively, the light chain locus may be the first to be inactivated. For complete elimination of the ability to produce light chain immunoglobulin, it is desirable to inactivate both the lambda and the kappa light chain immunoglobulin loci. At any stage, the xenogeneic loci may be introduced.

As already indicated, the target locus may be substituted with the analogous xenogeneic locus. In this way, the xenogeneic locus will be placed substantially in the same region as the analogous host locus, so that any regulation associated with the position of the locus will be substantially the same for the xenogeneic immunoglobulin locus. For example, by isolating the variable region of the human IgH locus (including V, D, and J sequences), or portion thereof, and flanking the human locus with sequences from the murine locus, preferably sequences separated by at least about 5 kbp, in the host locus, preferably at least about 10 kbp in the host locus, one may insert the human fragment into this region in a recombinational event(s), substituting the human immunoglobulin locus for the endogenous variable region of the host immunoglobulin locus. In this manner, one may disrupt the ability of the host to produce an endogenous immunoglobulin subunit, while allowing for the promoter of the human immunoglobulin locus to be activated by the host enhancer and regulated by the regulatory system of the host.

In order to provide for the production of xenogeneic binding proteins in a host, it is necessary that the host be competent to provide the necessary enzymes and other factors involved with the production of antibodies, while lacking competent endogenous genes for the expression of heavy and light subunits of immunoglobulins. Thus, those enzymes and other factors associated with germ line rearrangement, splicing, somatic mutation, and the like will be functional in the host. What will be lacking is a functional natural region comprising the various exons associated with the production of endogenous immunoglobulin.

The integration of introduced xenogeneic DNA may be random or homologous depending on the particular strategy to be employed. Thus, by using transformation, using repetitive steps or in combination with breeding, transgenic animals may be obtained which are able to produce xenogeneic binding proteins in the substantial absence of light or heavy endogenous immunoglobulin. By transformation is intended any technique for introducing DNA into a viable cell, such as conjugation, PEG-mediated cell fusion, transformation, transfection, transduction, electroporation, lipofection, biolistics, or the like.

Once the xenogeneic loci, have been introduced into the host genome, either by homologous recombination or random integration, and host animals have been produced with the endogenous immunoglobulin loci inactivated by appropriate breeding of the various transgenic animals or animals derived from chimeric animals, one can produce a host which lacks the native capability to produce endogenous immunoglobulin, but has the capacity to produce xenogeneic immunoglobulins with at least a significant portion of the repertoire of the xenogeneic source.

The functional inactivation of the two copies of each of the three host Ig loci (heavy, kappa and lambda), where the host then contains the human IgH and the human Ig kappa and/or lambda loci would allow for the production of purely human antibody molecules without the production of host or host/human chimeric antibodies. Such a host strain, by immunization with specific antigens, would respond by the production of murine B-cells producing specific human antibodies, which B-cells could be fused with murine myeloma cells or be immortalized in any other manner for the continuous stable production of human monoclonal antibodies. Methods are well known in the art for obtaining continuous stable production of monoclonal antibodies.

The subject methodology and strategies need not be limited to producing complete immunoglobulins, but provides the opportunity to provide for regions joined to a portion of the constant region, e.g., $C_{H1}$, $C_{H2}$, $C_{H3}$, or $C_{H4}$, or combination thereof. Alternatively, one or more of the exons of the $C_H$ and $C_k$ or $C_\lambda$ regions may be replaced or joined to a sequence encoding a different protein, such as an enzyme, e.g., plasminogen activator, superoxide dismutase, etc.; toxin, e.g., ricin, abrin, diphtheria toxin, etc.; growth factor; cytotoxic agent, e.g., TNF; receptor ligand, or the like. See, for example, Wo 89/07142; WO 89/09344; and WO 88/03559. By inserting the protein of interest into a constant region exon and providing for splicing of the variable region to the modified constant region exon, the resulting binding protein may have a different C-terminal region from the immunoglobulin. By providing for a stop sequence with the inserted gene, the protein product will have the inserted protein as the C-terminal region. If desired, the constant region may be entirely substituted by the other protein, by providing for a construct with the appropriate splice sites for joining the variable region to the other protein.

The B-cells from the transgenic host producing immunoglobulin or immunoglobulin analog may be used for fusion to a murine myeloid cell to produce hybridomas or immortalized by other conventional process, e.g., transfection with oncogenes. These immortalized cells may then be grown in continuous culture or introduced into the peritoneum of a compatible host for production of ascites.

The subject invention provides for the production of polyclonal human anti-serum or human monoclonal antibodies or antibody analogs. Where the mammalian host has been immunized with an immunogen, the resulting human antibodies may be isolated from other proteins by using an affinity column, having an Fc binding moiety, such as protein A, or the like.

The invention includes the following embodiments of non-human hosts (see also FIG. 18):

I. Animals heterozygous for an inactive endogenous light chain immunoglobulin gene (homozygous animals are obtained by interbreeding);

II. Animals heterozygous for an inactive endogenous heavy chain immunoglobulin gene (homozygous animals are obtained by interbreeding);

III. Animals homozygous for functional endogenous light and heavy chain immunoglobulin genes and hemizygous for (i.e. containing one copy of) foreign, preferably human, heavy chain immunoglobulin genes (homozygous animals are obtained by interbreeding);

IV. Animals homozygous for functional endogenous light and heavy chain immunoglobulin genes and hemizygous for foreign, preferably human, light chain immunoglobulin genes (homozygous animals are obtained by interbreeding);

V. Animals heterozygous for inactive endogenous heavy and light chain immunoglobulin genes obtained by crossbreeding animals of category I with animals from category II (homozygous animals are obtained by interbreeding);

VI. Animals heterozygous for inactive endogenous heavy and light chain immunoglobulin genes and hemizygous for foreign, preferably human, heavy chain immunoglobulin genes obtained by crossbreeding animals of category III with animals from category V (animals homozygous for the inactive endogenous loci and homo- or hemizygous for the foreign gene are obtained by interbreeding);

VII. Animals heterozygous for inactive endogenous heavy and light chain immunoglobulin genes and hemizygous for foreign, preferably human, light chain immunoglobulin genes obtained by crossbreeding animals of category IV with animals from category V (animals homozygous for the inactive endogenous loci and homo- or hemizygous for the foreign gene are obtained by interbreeding);

VIII. Animals homozygous or heterozygous for inactive endogenous heavy and light chain immunoglobulin genes and hemizygous for foreign, preferably human, light and heavy chain immunoglobulin genes, obtained by crossbreeding animals of category VI and VII (animals homozygous for the inactive endogenous loci and homo- or hemizygous for the foreign gene are obtained by interbreeding);

In a preferred embodiment, the homozygous animals of category VIII are used to produce human antibodies.

IX. Animals homozygous for functional endogenous heavy and light chain immunoglobulin genes and hemizygous for foreign, preferably human, heavy and light chain immunoglobulin genes, obtained by crossbreeding animals of category III and IV (homozygous animals are obtained by interbreeding);

X. Animals heterozygous for an inactive endogenous heavy chain immunoglobulin gene and hemizygous for foreign, preferably human, heavy and light chain immunoglobulin genes, obtained by crossbreeding animals of category II and IX (animals homozygous for the inactive endogenous loci and homo- or hemizygous for the foreign gene are obtained by interbreeding).

XI. Animals heterozygous for an inactive endogenous light chain immunoglobulin gene and hemizygous for foreign, preferably human, heavy and light chain immunoglobulin genes, obtained by crossbreeding animals of category I and IX (animals homozygous for the inactive endogenous loci and homo- or hemizygous for the foreign gene are obtained by interbreeding).

The invention also provides a method for introducing large continuous, xenogeneic DNA sequences into a-non-human, e.g. mammalian, host. Usually, the sequences will be at least 100 kb, more usually at least about 200 kb, generally ranging from about 200 to 1000 kb. Thus, one may wish to transfer a locus of interest, such as the immunoglobulin locus, T-cell receptor locus, major histocompatibility locus; regions of an xenogeneic chromosome, which may include one or more genes of interest, which may or may not have been characterized, such as the Low Density Lipoprotein (LDL) receptor, Apolipoprotein (Apo) B, Apo E, cystic fibrosis transmembrane conductor regulator, dystrophin, or regions of xenogeneic chromosomes that may be involved in partial chromosome trisomy (e.g. chromosomes 21, 7 and 10); and viruses. The DNA may comprise wild type or defective genes for studying a variety of diseases by creating dominant mutations or complementing recessive mutations, for example the LDL receptor and Apo B genes can be introduced for the study of hypercholesterolemia, hyperlipoproteinemia and atherosclerosis, Factor VIII or IX can be introduced for hemophilia, cystic fibrosis transmembrane conductance regulator can be introduced for cystic fibrosis and the dystrophin gene for muscular dystrophy. The xenogeneic DNA to be introduced using a YAC is from a mammalian source, particularly primates, more particularly human, other vertebrates or invertebrates and the like. One can thus impart numerous novel capabilities to the host, create genetic responses related to the xenogeneic source of the DNA, provide for the production of antibodies, provide for specific combinations of transcription factors, provide for metabolic systems, introduce dominant mutations or complement recessive mutations. The xenogeneic DNA may be modified when present in a YAC. Because homologous recombination is efficient in yeast, giving a high ratio of site-specific integration of homologous DNA, where the homologous DNA flanks other DNA of interest, one is able to modify the xenogeneic DNA before introduction into an ES cell. In this way, one can introduce defective genes into the host which express defective proteins to mimic diseased states of the xenogeneic host, to study various mechanisms of the interaction of defective proteins with other xenogeneic proteins or endogenous proteins, or to study genes or gene systems.

In general, to transfer large DNA segments, as described in detail herein, YACs are employed which comprise a yeast centromere, an origin of replication and telomeres bounding the DNA of interest. Various centromeres or telomeres may be used, particularly the centromeres from yeast chromosomes 4 and 5. The YAC has a marker which allows for selection or screening of cells into which the YAC becomes integrated. Not all markers allow for efficient selection. Particularly, the HPRT gene, more particularly human HPRT, is found to permit efficient selection of HPRT-deficient ES cells carrying the YAC. Other known selectable or screenable markers include hygromycin, neomycin, β-gal, and GPT. The ES cell may be derived from any non-human host, from which ES cells are available, and can be expanded in culture, which remain viable and functional, for which a marker for selection exists, and where the ES cell can be introduced into an embryo and can repopulate the host, including the germline. For the most part this capability has been established with rodents, e.g. mice and rats, and to a lesser extent with guinea pigs. Mice have been used for the production of antibodies or B-lymphocytes for immortalization for the production of antibodies. Because mice are easy to handle, can be produced in large quantities, and are known to have an extensive immune repertoire, mice will usually be the animal of choice. As other species of ES cells become available, these may also be employed in accordance with the subject invention. Of particular interest will be small laboratory animals, or domestic animals particularly rodents, including mice, rats, rabbits, cows, pigs, hamsters, horses, dogs, sheep and guinea pigs, or birds such as chickens, turkeys, etc. The ES cells may have one or more mutations, for example lacking a particular activity. Of particular interest in this invention are ES cells that are deficient in HPRT. In addition, fertilized eggs of certain species may find use in accordance with the invention.

The YAC may be obtained by screening existing human YAC libraries such as those available from the Centre d'Etude du Polymorphisme Human (C.E.P.H.), Paris, France, and Washington University, St. Louis, Mo., using standard procedures. Alternatively, the YAC is readily prepared as described in detail herein, by joining the yeast flanking segments comprising one arm with a centromere and telomere and another with a telomere together with the DNA of interest. Usually there will also be one or more markers present that allow for selection in the yeast host cells. For yeast selection, of particular interest are markers which complement mutations of the yeast host, such as genes involved in the production of amino acids, purines or pyrimidines, URA3, TRP1, LYS2, ADE2 on the YAC to complement ura3, trp1, lys2 and Ade2 mutations in the host. By providing for complementation, for the most part only yeast cells carrying the entire YAC will be able to survive in a selective medium. In addition to genetic verification that both YAC arms have been retained, it is desirable to confirm the integrity of the YAC using a method such as pulsed-field gel electrophoresis.

Those yeast hosts carrying the YAC may then be used as a source of the YAC for introduction into the ES cell. Transfer of the YAC is efficiently achieved by preparing yeast spheroplasts in accordance with conventional ways. By degrading the outer wall, under mild conditions, in an isotonic medium, spheroplasts are produced in high yield. Exponentially growing ES cells are protease-treated, e.g. trypsinized, and combined with the spheroplasts. Conveniently, a pellet of yeast spheroplasts can be prepared and the ES cells are spun with the pellet and exposed to a fusogenic agent such as PEG for 1–2 minutes. The cells are then resuspended and incubated in appropriate serrum-free medium. The cells are then plated onto feeder cells, followed by selection in accordance with the selective marker. For the HPRT gene, HAT medium may be employed for selection. Surviving fusion colonies are then, picked, expanded and analyzed. Analysis may be performed by restriction enzyme analysis, combined with Southern blotting or pulsed-field gel electrophoresis, or by the polymerase chain reaction (PCR), employing appropriate primers, at least one of which is complementary to the DNA insert, and probing with repetitive sequences present in the xenogeneic DNA, such as Alu, for detection of human DNA sequences. Ty, Y', rDNA, delta sequences are used to probe for for yeast sequences. Probes for YAC ends are used to confirm integrity of the YAC. Those cells that demonstrate the intact or substantially intact YAC DNA integrated into the host genome are then used in the next steps. In some clones, only a portion or little or none of the yeast DNA becomes integrated into the mouse genome. The integrated yeast DNA ranges from more than about 90% of the original yeast genome to less than about 10%.

In a preferred embodiment, efficient production of transgenic non-human hosts is provided using a process which integrates large, at least 100 kb, xenogeneic DNA fragments, in substantially intact form, into a host embryonic stem (ES) cell or fertilized egg (zygote). The introduction of the xenogeneic DNA is efficiently achieved by fusion of the ES cell with yeast spheroplasts that contain YACs carrying the 100 kb DNA and a selectable marker, under conditions allowing for integration of the YAC DNA containing the marker into the ES cell genome, or by transfection of a purified YAC into ES cells. ES cells comprising the YAC integrated into the genome are then selected by means of the marker, which is functional in the ES cell. For example, the hypoxanthine phosphoribosyl transferase (HPRT) gene may be used as a marker in HPRT deficient (HPRT-) ES cells. For producing animals from embryonic stem cells, after transformation, the cells may be plated onto a feeder layer in an appropriate medium, e.g. fetal bovine serum enhanced DMEM. The ES cell may have a single targeted locus (heterozygous), or may be manipulated by the process of homogenotization to have both loci targeted (homozygous). The process of homogenotization (formation of homozygotes) uses selective pressure to grow out those cells which have the gene targeting event on both chromosomes. Cells containing the two targeted alleles may be detected by employing a selective medium and after sufficient time for colonies to grow, colonies may be picked and analyzed for the occurrence of integration or homologous recombination. As described previously, the PCR may be used, with primers within or outside of the construct sequence, but at the target locus.

Those colonies which show homologous recombination may then be used for embryo manipulation and blastocyst injection. The selected ES cells are then introduced into embryos, by microinjection or other means, into the appropriate host. For example, murine blastocyts may be obtained from female animals by flushing the uterus 3.5 days after ovulation. The modified ES cells are then trypsinized and at least 1 and up to 15 cells may be injected into the blastocoel of the blastocyst. After injection, at least 1 and no more than about 10 of the blastocysts are returned to each uterine horn of pseudo-pregnant females. The females proceed to term and the resulting chimeric animals can be analyzed for the presence of the YAC in their somatic cells. By "chimeric" is meant an animal that carries cells derived from more than one source, e.g. from the host and another animal. For example, in the present invention a chimeric murine animal contains a genetically engineered modification, particularly a human gene, in some of its cells, e.g. in cells that develop from the modified embryonic stem cells. The presence of the integrated YAC in chimeric hosts that are generated is then analyzed. The chimeric hosts are evaluated for germline transmission of the ES cell genome by mating, for example chimeric mice are mated with C57BL/6J mice. Chimeric hosts may be bred with non-chimeric hosts, either syngeneic or allogeneic, to screen for chimeras that carry the YAC in their germ cells. offspring that are heterozygous for the genetic modification are then interbred to produce progeny that are homozygous for the modification, stably transmitting the functioning YAC construct to their progeny.

The method of the invention for introduction of large xenogeneic DNA segments into a non-human host, particularly a rodent and usually a murine animal, provides for stable integration of the DNA. Genes in the inserted DNA are found to be functional and the resulting chimeric hosts are able to provide for germline transmission of the integrated DNA. After breeding of the chimeric host, transgenic heterozygous hosts are produced and are mated to produce a homozygous animal that may be used for a wide variety of purposes, including production of products, such as binding proteins, for example immunoglobulins, for screening of various drugs, for gene therapy, for example to complement for recessive genetic disorders, to study various diseases, to study the function and regulation of poorly mapped large DNA fragments.

The following examples are offered by way of illustration and not by way of limitation.

EXPERIMENTAL

EXAMPLE I

I. Inactivation of the mouse heavy chain J ($J_H$) genes

A. Construction of the targeting inactivation vector

Figure 1B:
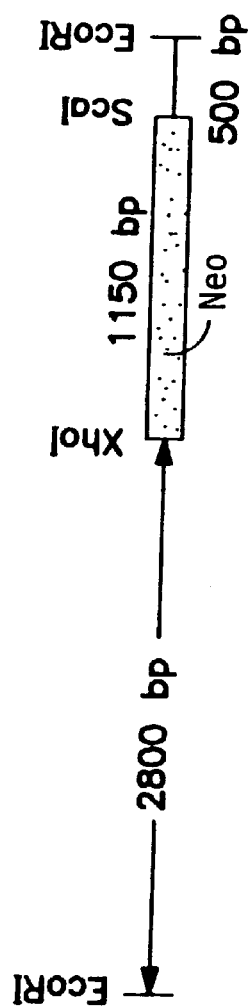

A 6.4 kb EcoRI fragment, containing the mouse heavy chain J genes and flanking sequences, is cloned from a Balb/c mouse embryo genomic library using the probes described in Sakano et al. (1981), Nature 290:562–565. This fragment (mDJ) is inserted into EcoRI-digested pUC19 plasmid (pmDJ). A 2.9 Kb fragment, containing the 4 J genes, is deleted by XhoI-ScaI digestion (pmDδJNeo, see FIG. 1). An 1150 bp XhoI-BamHI fragment, containing a neomycin-resistance gene driven by the Herpes simplex virus thymidine kinase gene (HSV-tk) promoter and a polyoma enhancer is isolated from pMC1Neo (Thomas and Capecchi (1987), Cell, 51, 503–512). A synthetic adaptor is added onto this fragment to convert the BamHI end into a ScaI end and the resulting fragment is joined to the XhoI-ScaI pmDSJ to form the inactivation vector (pmDδJ.Neo) in which the 5' to 3' orientation of the neomycin and the heavy chain promoters is identical. This plasmid is linearized by NdeI digestion before transfection to ES cells. The sequences driving the homologous recombination event are 3 kb and 0.5 kb fragments, located 5' and 3' to the neomycin gene, respectively.

B. Culturing, Electroporation and Selection of ES Cells

The ES cell line E14TG2a (Hooper et al. (1987), Nature, 326:292–295) is cultured on mitomycin treated primary embryonic fibroblast-feeder layers essentially as described (Doetschman et al. (1985), J. Embryol. ExP. Morphol. 87:27–45). The embryonic fibroblasts are prepared from embryos from C57BL/6 females that are mated 14 to 17 days earlier with a male homozygous for a neomycin transgene (Gossler et al. (1986), PNAS 83:9065–9069). These cells are capable of growth in media containing G418. Electroporation conditions are described by (Boggs et al. (1986), Ex. Hematol. (NY) 149:988–994). ES cells are trypsinized, resuspended in culture media at a concentration of $4\times10^7$/ml and electroporated in the presence of the targeting DNA construct at a concentration of 12 nM in the first experiment and 5 nM DNA in the second. A voltage of 300 V with a capacitance of 150–250 µF is found optimal with an electroporation cell of 5 mm length and 100 mm2 cross-section. 5×10⁶ electroporated cells are plated onto mitomycin-treated fibroblasts in 100 mm dishes in the presence of Dulbecco's modified Eagle's media (DMEM) supplemented with 15% fetal bovine serum (FBS) and 0.1 mM 2-mercaptoethanol. The media is replaced 24 hrs after electroporation with media containing 200 µg/ml G418.

ES colonies resulting 10–14 days after electroporation are picked with drawn out capillary pipettes for analysis using PCR. Half of each picked colony is saved in 24-well plates already seeded with mitomycin-treated feeder cells. The other halves, combined in pools of 3–4, are transferred to Eppendorf tubes containing approximately 0.5 ml of PBS and analyzed for homologous recombination by PCR. Conditions for PCR reactions are essentially as described (Kim and Smithies (1988), Nucleic Acids Res. 16:8887–8893). After pelleting, the ES cells are resuspended in 5 µl of PBS and are lysed by the addition of 55 µl of H₂O to each tube. DNAses are inactivated by heating each tube at 95° C. for 10 min. After treatment with proteinase K at 55° C. for 30 min, 30 µl of each lysate is transferred to a tube containing 20 µl of a reaction mixture including PCR buffer: 1.5 µg of each primer, 3U of Tag polymerase, 10% DMSO, and dNTPs, each at 0.2 mM. The PCR expansion employs 55 cycles using a thermocycler with 65 seconds melt at 92° C. and a 10 min annealing and extension time at 65° C. The two priming oligonucleotides are TGGCGGACCGCTATC-CCCCAGGAC (SEQ ID NO: 1) and TAGCCTGGGTC-CCTCCTTAC (SEQ ID NO: 2), which correspond respectively to a region 650 bases 3' of the start codon of the neomycin gene and sequences located in the mouse heavy chain gene, 1100 bases 3' of the insertion site. 20 µl of the reaction mix is electrophoresed on agarose gels and transferred to nylon membranes (Zeta Bind). Filters are probed with a ³²P-labelled fragment of the 991 bp XbaI fragment of the J-C region.

EXAMPLE II

II. Deletion of the mouse Ig heavy chain J (J_H) genes in ES cells

A. Construction of the replacement targeting vector

A 6.1-Kb EcoRI fragment, containing the mouse immunoglobulin heavy chain J region genes and flanking sequences, cloned from a BALB/c mouse embryo genomic library and inserted into pUC18 (pJ_H), was digested with XhoI and NaeI to delete an about 2.3 kb fragment containing the four J genes (see FIG. 2A). An about 1.1 kb XhoI-BamHI fragment, blunted at the BamHI site, containing a neomycin resistance gene driven by the Herpes simplex virus thymidine kinase gene (HSV-tk) promoter and polyoma enhancer was isolated from pMC1Neo (Thomas and Capecchi (1987), Cell, 51, 503–512). This fragment was inserted into the XhoI-NaeI deleted pJH to form the deletion vector (pmHδJ, see FIG. 2B), in which the transcriptional orientation of the neomycin and the heavy chain genes is the same. This plasmid was linearized by NdeI digestion before transfection to ES cells. The sequences driving the homologous recombination event are about 2.8 kb and about 1.1 kb fragments, located 5' and 3' to the neomycin gene, respectively.

B. Culturing, Electroporation, and Selection of ES cells

The ES cell line E14TG2a (Koller and Smithies (1989), PNAS USA, 86:8932–8935) was cultured on mitomycin C-treated embryonic fibroblast feeder layers as described (Koller and Smithies (1989), PNAS USA, 86:8932–8935). ES cells were trypsinized, resuspended in HBS buffer (pH 7.05; 137 mM NaCl, 5 mM KCl, 2 mM CaCl₂, 0.7 mM Na₂HPO₄, 21 mM HEPES pH 7.1) at a concentration of 2×10⁷/ml and electroporated in the presence of 50 µg/ml of the linearized inactivation vector. Electroporation was carried out with a BioRad Gene Pulser using 240 volts and 500 µF capacitance. 5×10⁶ electroporated cells were plated onto mitomycin C-treated fibroblasts in 100 mm dishes in the presence of Dulbecco's modified Eagle's media (DMEM) supplemented with 15% fetal bovine serum and 0.1 mM 2-mercaptoethanol. The media was replaced 24 hr after electroporation with media containing 200 µg/ml G418. G418-resistant ES colonies resulting from growth 12–14 days after electroporation were picked with drawn out capillary pipettes for analysis using the polymerase chain reaction (PCR). Half of each picked colony was transferred to an individual well of a 24-well plate, already seeded with mitomycin C-treated feeder cells. The other halves, combined in pools of four, were transferred to Eppendorf tubes containing 0.3 ml of PBS and cell lysates were prepared for PCR analysis as described by Joyner et al (1989) Nature, 338:153–155. The PCR reaction included 5–20 µl of the cell lysate, 1 µM of each primer, 1.5 U of Taq polymerase and 200 µM of dNTPs. The PCR amplification employed 45 cycles using a thermal cycler (Perkin-Elmer Cetus), with 1 min. melt at 94° C., 2 min. annealing at 55° C., and 3 min. extension at 72° C. The two priming oligonucleotides are ACGGTATCGCCGCTCCCGAT (SEQ ID NO:3:) and AGTCACTGTAAAGACTTCGGGTA (SEQ ID NO: 4), which correspond respectively to about 120 bases 5' of the BamHI site of the neomycin gene, and to the sequences located in the mouse heavy chain gene, about 160 bases 3' of the insertion site. Successful homologous recombination gives rise to an about 1.4 kb fragment. 20 µl of the reaction mixture is electrophoresed on 1% agarose gels, stained with ethidium bromide and transferred to nylon membranes (Gene Screen). Filters were probed with a ³²P-labelled EcoRI-PstI about 1.4 kb fragment located in the mouse heavy chain, 3' of the insertion site (see FIG. 2). For further analysis, genomic DNA was prepared from ES cells, digested with restriction enzymes as recommended by the manufacturers, and fragments were separated on 1% agarose gels. DNA was transferred to nylon membranes (Gene Screen) and probed with the ³²P-labelled fragment as described above.

C. Analysis of G418-resistant ES colonies

In the first experiment, PCR analysis of the pooled colonies detected one positive PCR signal of the expected size (about 1.4 kb) out of 34 pools representing 136 G418-resistant colonies. The four individual colonies that had contributed to this positive pool were analyzed individually by PCR, and a positive clone, ES33D5, was identified. Similar analysis of 540 G418-resistant colonies obtained in the second experiment yielded 4 additional positive clones (ES41-1, ES61-1, ES65-1, ES110-1).

In order to verify the targeted disruption of one copy of the J genes, (the gene is autosomal and thus present in two copies), the PCR positive clones were expanded and genomic DNA was prepared, digested with HindIII or with SacI and analyzed by Southern analysis as described using the EcoRI-PstI probe.

Figure 2C:
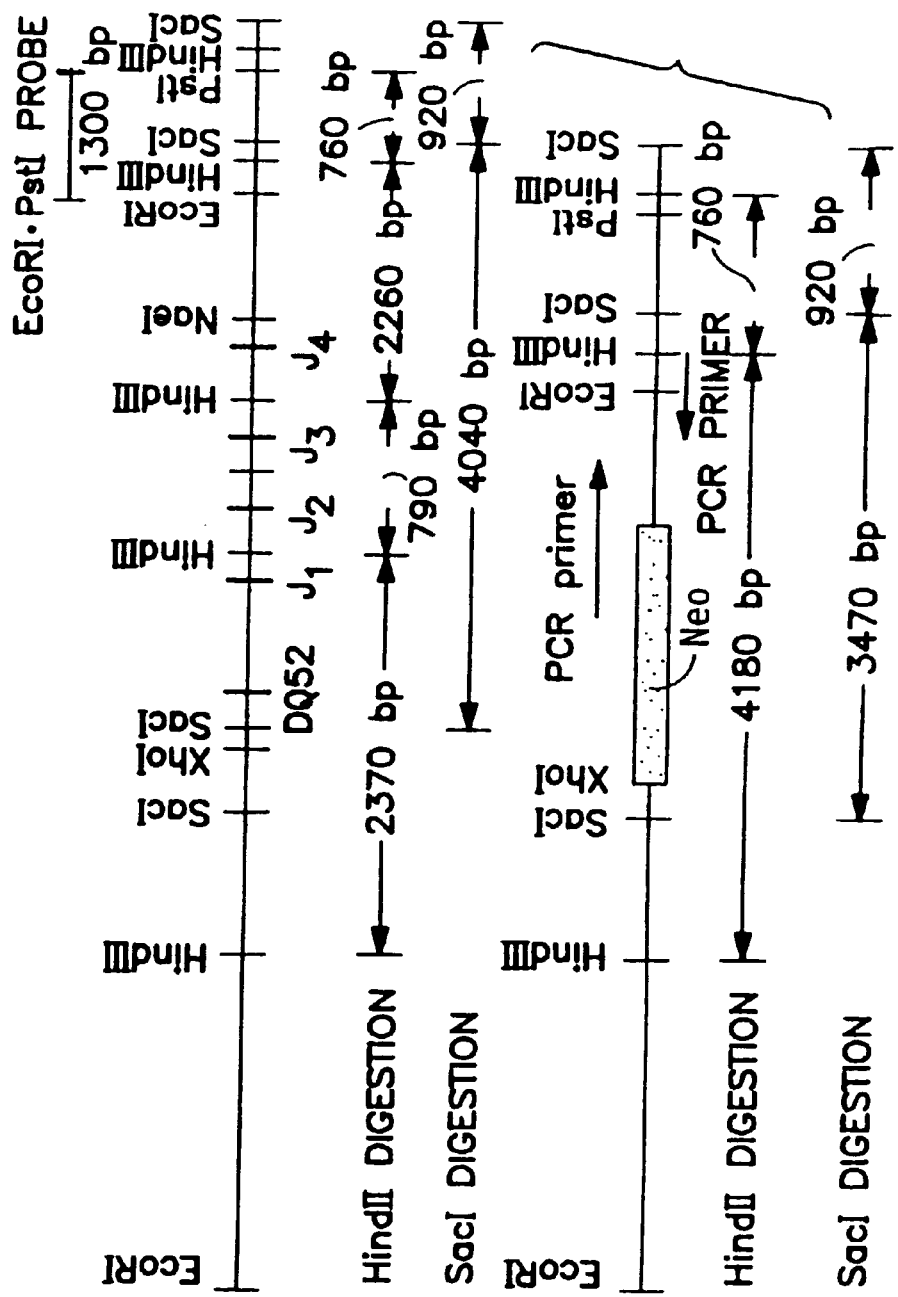
Figure 3A:
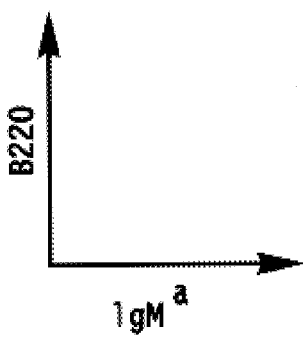
FIGS. 3A–B is a flow cytometry plot of antibody staining for IgM allotypes in mouse strains, as described in Example II, infra.
Figure 3A:
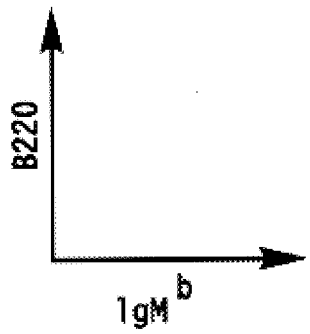
Figure 3A:
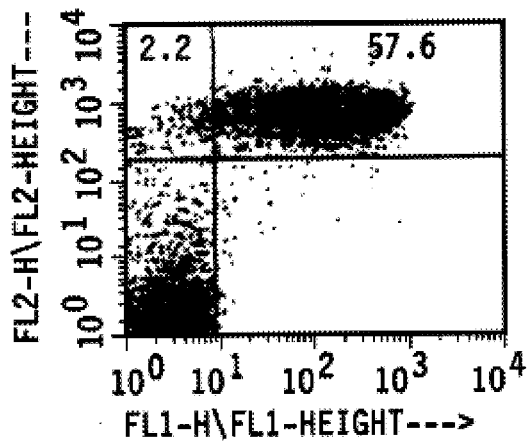
Figure 3A:
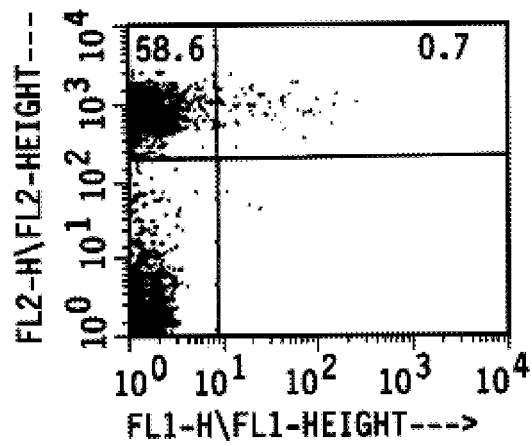
Figure 3A:
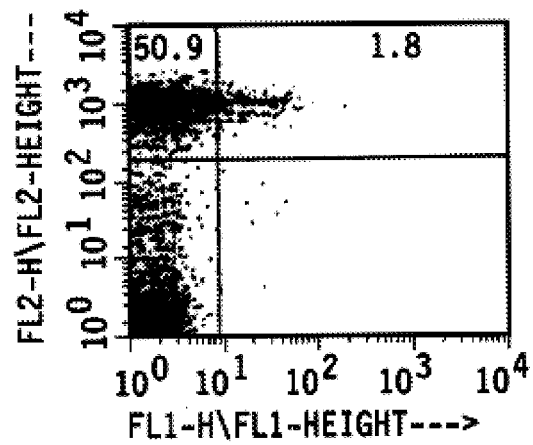
Figure 3A:
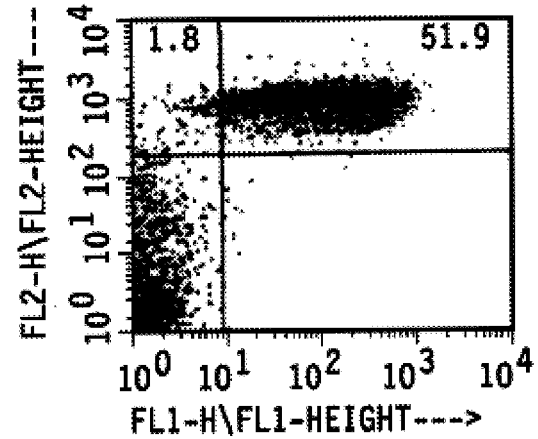
Figure 3B:
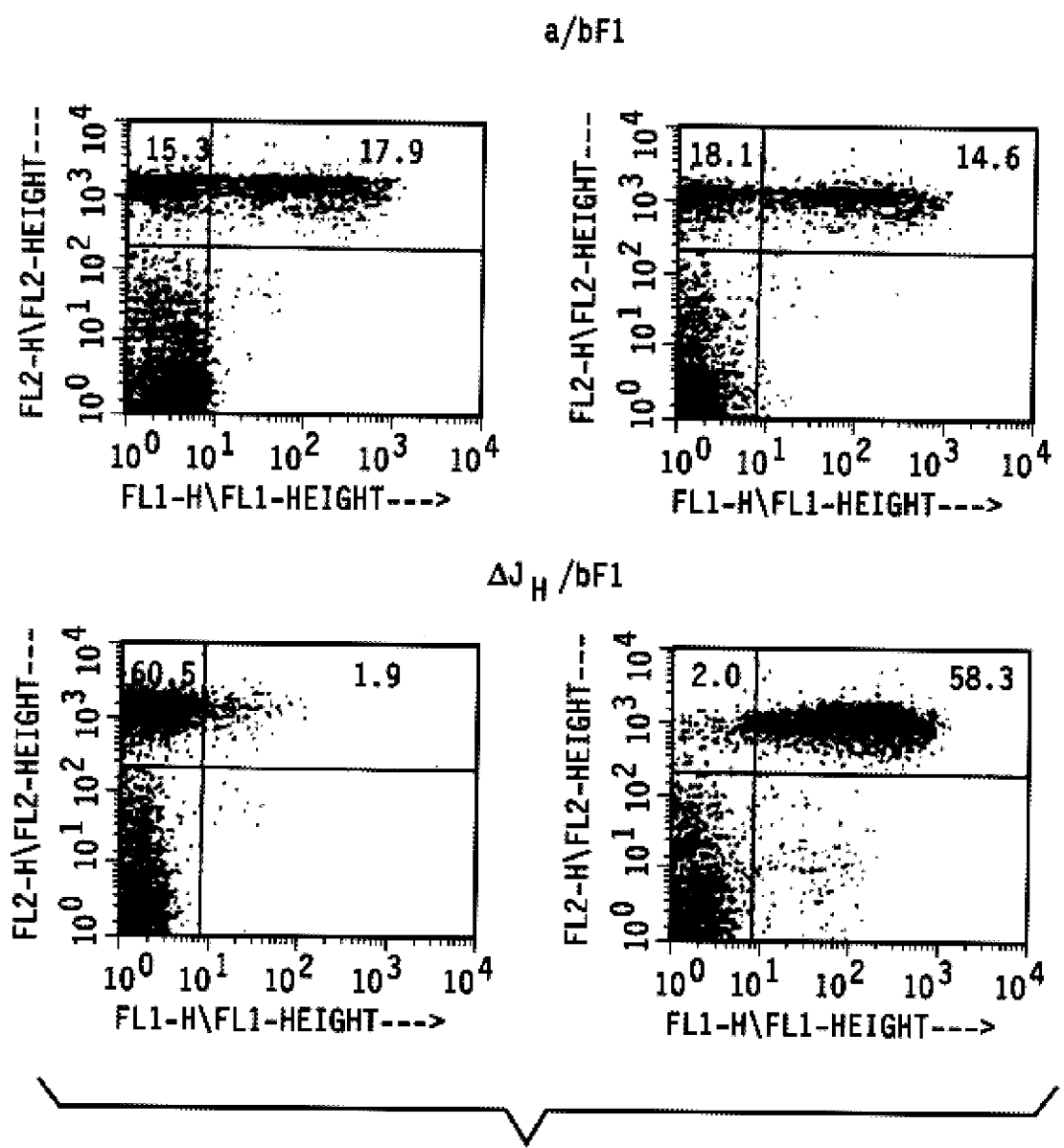

The replacement of the J genes by insertion of the neomycin gene by an homologous recombination event results in a HindIII fragment, detectable with the EcoRI-PstI probe, which is about 1.9 kb longer than the equivalent fragment in the native locus, due to the loss of two HindIII sites located in the deleted J gene region (see FIG. 2C). Southern analysis of each of the 5 positive clones by HindIII digestion gave a pattern which indicated that one of the two copies of the heavy chain J genes had been disrupted. Three labelled fragments were detected: one fragment (about 760 bp), identical in size to that present in untreated cells at the same intensity, one fragment (about 2.3 kb) identical in size to that present in untreated cells, but of decreased intensity in the PCR positive clone, and an additional fragment about 4.2 kb, the size predicted for an homologous recombination event, present only in the PCR-positive clones. Similarly, the replacement of the J genes by the neomycin gene by an homologous recombination event results in a loss of one SacI site and the appearance of a fragment, detectable with the EcoRI-PstI probe, which is about 570 bp smaller than the equivalent fragment in the native locus (see FIG. 2C). Southern analysis of the clones by SacI digestion gave the expected pattern of one native and one targeted allele: about 4.0 kb fragment, identical in size to that detected in untreated cells, but of decreased intensity in the 5 positive clones, and an additional fragment of about 3.4 kb, the size predicted for a targeted homologous recombination event, present only in the identified clones. Rehybridization of the Southern blots with a probe for the neomycin gene showed that only the 4.2 kb and 3.4 kb fragments, resulting from the HindIII and the SacI digestion, respectively, hybridized to the probe as predicted by the targeting event.

D. Generation of chimeric mice with $J_H$ deletions

Three and a half day old C57BL/6J (Jackson Laboratories, Bar Harbor, Me.) blastocysts were obtained from 4–5 week old superovulated females as described by Koller, et al. 1989 (supra). ES cells were trypsinized, washed once with fresh DMEM media, and diluted to about $1 \times 10^6$/ml in DMEM medium containing 10% fetal bovine serum and 20 mM HEPES, pH 7.5. 10 to 15 cells were injected into the blastocoel of each blastocyst. ES-cell containing blastocysts were then surgically transferred to one uterine horn of C57BL/6J×DBA/2 or C57BL/6J×CBA F1 pseudopregnant females.

The contribution of ES cells to the offspring was judged visually by examination of the coat color of the pups. C57BL/6J mice are solid black in color. The ES cell parent line E14TG2a was isolated from 129/Ola embryos, which carry three coat color genes, the dominant $A^W$ allele at the agouti locus, the recessive pink-eyes-dilute allele at the p locus, and the recessive $C^{ch}$ at the c locus. Chimeric offspring in which the ES cells participated in the formation of the animal have coats containing agouti and cream hairs.

Germline transmission ability of the chimeric mice was evaluated by mating with a C57BL/6J mouse and scoring for F1 offspring with agouti color. 50% of these agouti mice would be expected to inherit the mutated heavy chain allele, which can be identified by Southern blot analysis of DNA isolated from tails.

The $J_H$-targeted ES cell line ES65-1, carrying one targeted heavy chain allele, was injected into C57BL/6J mouse blastocysts. About 45% of the surviving pups were chimeras. Two chimeric females, 238-2 and 244-3, upon mating with C57BL/6J males, yielded germline transmission at a frequency of 100% and 15%, as determined by the percent of agouti offspring. Southern blot analysis of DNA from heterozygous offspring indicated the presence of the targeted heavy chain in addition to one native allele in 2 out of 5 agouti progeny tested.

Mice homozygous for the mutation were obtained by intercrossing male and female mice which were identified as $J_H$-deleted ($\delta J_H$) heterozygotes. Offspring of these matings were analyzed for the presence of the two targeted heavy chain alleles by Southern blot analysis.

E. Analysis of B cells from chimeric mice

If deletion of the $J_H$ region is sufficient to inactivate the heavy chain locus, then it should result in complete block of development of IgM-expressing B cells and of antibody production. Mice which are heterozygous at the $J_H$ locus carry one intact and functional heavy chain allele, derived from the C57BL/6J parent, and one $J_H$-deleted heavy chain allele which is derived from the ES cells (129/Ola strain). The 129 and B6 strains differ in Ig heavy chain allotypes. The ES-derived B cells (IgM$^a$ allotype) can be distinguished from B6-derived B cells (IgM$^b$ allotype) with allotype-specific monoclonal antibodies, using flow cytometry analysis of antibody expressing B.

The specificity of these antibodies is shown in FIGS. 3 (A–C). Peripheral blood lymphocytes were stained with antibodies to the B cell specific marker, B220, and with antibodies to the IgM allotype. B cells from C57BL/6J mice stained with antibodies directed against the IgM$^b$ allotype but not the IgM$^a$ allotype (FIG. 3B). B cells derived from 129/Ola mice stained with antibody against the IgM$^a$ allotype, but not the IgM$^b$ allotype (FIG. 3A). In heterozygous (a/b F1) mice carrying one intact ES-derived heavy chain allele and one intact C57BL/6J-derived heavy chain allele, both allotypes were present in equal amounts (FIG. 3C).

When B cells from mice which were heterozygous for the $J_H$ deletion were analyzed, where the $J_H$ deleted heavy chain allele was from the 129/Ola parent, there were no cells positive for the IgM$^a$ allotype. All B cells were IgM$^b$ positive, from the intact C57BL/6J heavy chain allele (FIG. 3D). These results indicated that the $J_H$-deleted heavy chain locus is inactivated and cannot encode a functional IgM antibody.

Figure 4A:
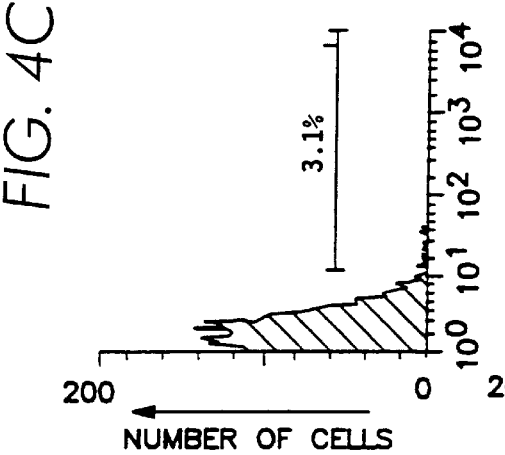
FIGS. 4A–F is a flow cytometry histogram of antibody staining for IgM allotypes in mouse strains, as described in Example II, infra.
Figure 4B:
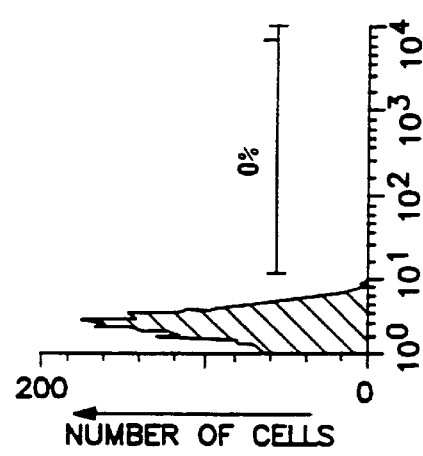
Figure 4C:
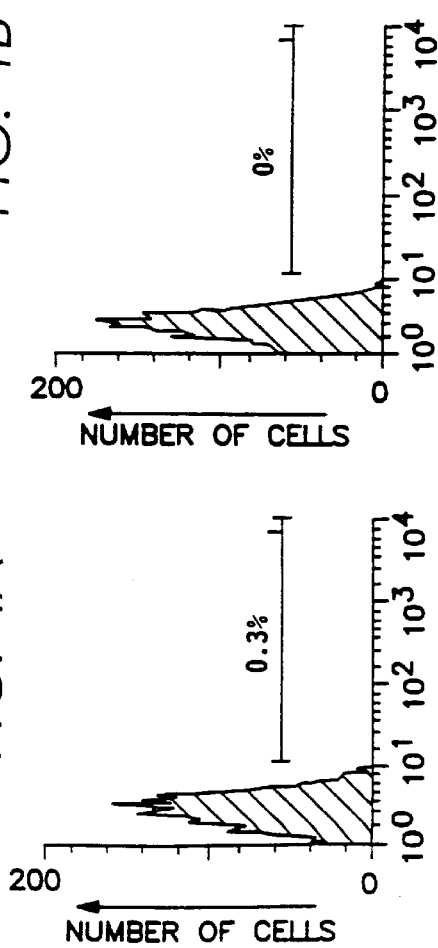
Figure 4D:
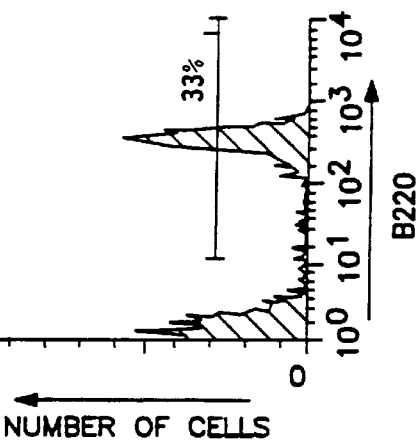
Figure 4E:
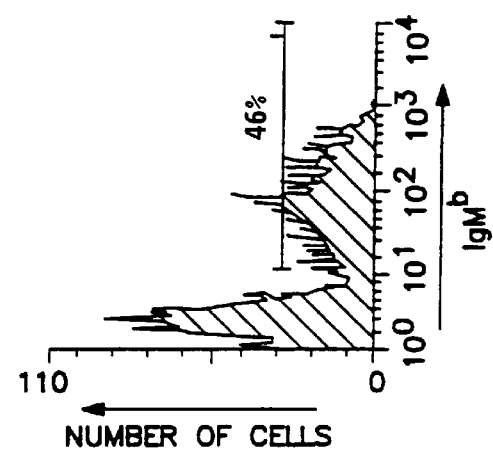
Figure 4F:
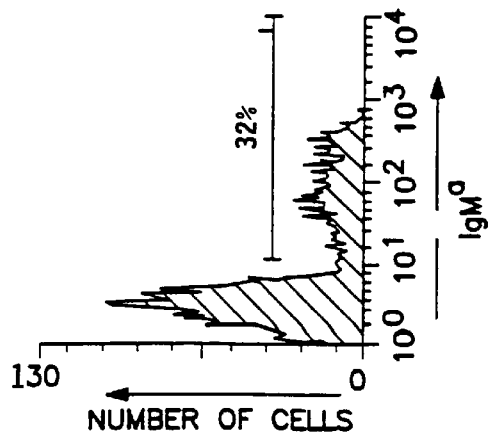

Mice which were homozygous for the $J_H$ deletion were also analyzed for the ability to produce functional antibodies. Peripheral blood lymphocytes from homozygous mutant mice were analyzed by flow cytometry, using antibodies to the B cell specific marker B220, and with the allotype specific markers (see FIG. 4). In contrast to the control mice (FIGS. 4D–F), no B220$^+$ cells, or IgM producing cells could be detected in the mutant mice (FIGS. 4A–C). In addition, the mutant mice had no detectable IgM in the serum. These results indicate that the deletion of the $J_H$ region from both heavy chain alleles leads to complete inhibition of B cell development to mature B cells and production of antibody.

F. Generation of homozygous mutant ES cells

The effect of $J_H$ deletion on B cells can also be analyzed by generating ES cells with both heavy chain alleles targeted, which are then used to produce chimeric mice which contain a population of lymphoid cells homozygous for the mutation.

Homozygous $\delta J_H$ mutant ES cells were generated by subjecting one of the heterozygous mutant ES clones, ES110-1, to elevated levels of G418 (1.4 mg/ml) thus selecting for homogenotization of the targeted allele. Seven of the surviving colonies were screened by Southern blot analysis using SacI digestion for the loss of the wild-type heavy chain allele and acquisition of a second targeted allele. One of these clones, ESDK207 was shown to have lost the native heavy chain allele, as evidenced by the inability of probes to detect the wild type 4.0 kb fragment and by the increased intensity of the 3.4 kb targeted fragment. Karyotypic analysis of ESDK207 indicated that, like the parent line ES110-1, about 80% of the cells had 40 chromosomes, suggesting that two targeted alleles were present. The homozygous mutant ES cells were microinjected into C57BL/6J blastocysts and chimeric mice were generated.

G. Analysis of B cells from homozygous chimeras

B cells from chimeric mice were analyzed to determine the effect of $J_H$ deletion on B cell development and antibody production. Lymphocytes from the ES cell line (129/Ola) can be distinguished from blastocyst-derived (C57BL/6J) lymphocytes by a monoclonal antibody to the Ly-9.1 marker, which is found on lymphocytes of 129 origin, but not those of B6 origin. In addition, the two strains differ in their IgM allotype, as previously described.

The chimeras analyzed had been derived from wild-type E14TG2a ES cells (WT), or from ES cells that were heterozygous (ES110-1, ES65-1) or homozygous (ESDK207) at the targeted $J_H$ region. Peripheral blood mononuclear cells were stained with antibodies to the B cell specific marker B220, and with antibodies to either Ly-9.1 or IgM allotypes, and then analyzed by two-color flow cytometry. To evaluate chimerism in the T cell lineage, the cells were stained with antibody for the T cell marker Thy 1.2, and with anti-Ly-9.1 antibody. Staining of cells from the parental mouse strains provided controls for the specificity and sensitivity of the assay.

Mice with similar degrees of chimerism, as judged by coat color, were compared. ES-derived B and T cells were detected in the peripheral blood of chimeric mice generated from the wild-type E14TG2a ES cells, confirming the ability of this cell line to give rise to lymphoid cells in vivo. Analysis of chimeras generated from single $J_H$-targeted ES65-1 and ES110-1 cells demonstrated the presence of $B220^{a+}/IgM^{a+}/Ly-9.1^+$ B cells containing a single, intact, ES cell-derived Ig heavy chain locus.

In contrast to the WT and single deletion chimeras, mice generated from the homozygous mutant ESDK207 cell line lacked $Ly-9.1^+/B220^+$ or $IgM^{a+}/B220+1$ B cells in peripheral blood. The observed lack of ESDK207-derived B cells was not due to a lack in lymphopoiesis, since ES-derived $Ly-9.1^+/B220^-$ cells represented 12% of the total pool of peripheral blood mononuclear cells. Of these, approximately half were $Thy-1.2^+$ T cells. Thus, deletion of the $J_H$ region from both alleles blocks development of mature $IgM^a$ producing B cells. Similar observations were made for chimeric spleen cells.

Chimeras were also tested for the presence of serum IgM derived from the ES cells. $IgM^a$ levels were high in chimeras from wild-type ES cells and cells with a single targeted mutation, but were undetectable in mice derived from the ESDK207 cell line.

Further analysis showed that the bone marrow of ESDK207 mice contained normal $IgM^{b+}$ B cells derived from the blastocyst host, but lacked ES-derived $IgM^{a+}$ B cells. However, DK207-derived bone marrow did contain a population of cells which were $B220^{dull}/Ly-9.1^+$ derived from the ES cells. The bone marrow is therefore likely to contain a subpopulation of ES cell-derived B cell precursors, whose maturation is blocked by the homozygous deletion of the $J_H$ region.

The bone marrow cells were also analyzed with three-color flow cytometry, using antibodies to Ly-9.1, B220 and either CD43 or Thy-1. 2. The results show the majority of ES-derived cells were CD43 positive, which is consistent with an early block in maturation. Many of the cells were also positive for Thy-1.2, as would be expected of very early B cell precursors. These data show that deleting the $J_H$ region results in the inability of the heavy chain locus to rearrange and produce functional IgM. Lack of IgH rearrangement results in a block of B cell maturation, restricting B cell progenitors to an early stage of development.

EXAMPLE III

Deletion of the Mouse Ig kappa light chain constant ($C_k$) region

A. Construction of the replacement targeting vector

The kappa region was inactivated with a replacement type vector, which was designed to delete the constant region of the kappa locus, and replace it with the G418 drug resistance marker through homologous recombination.

Figure 5:
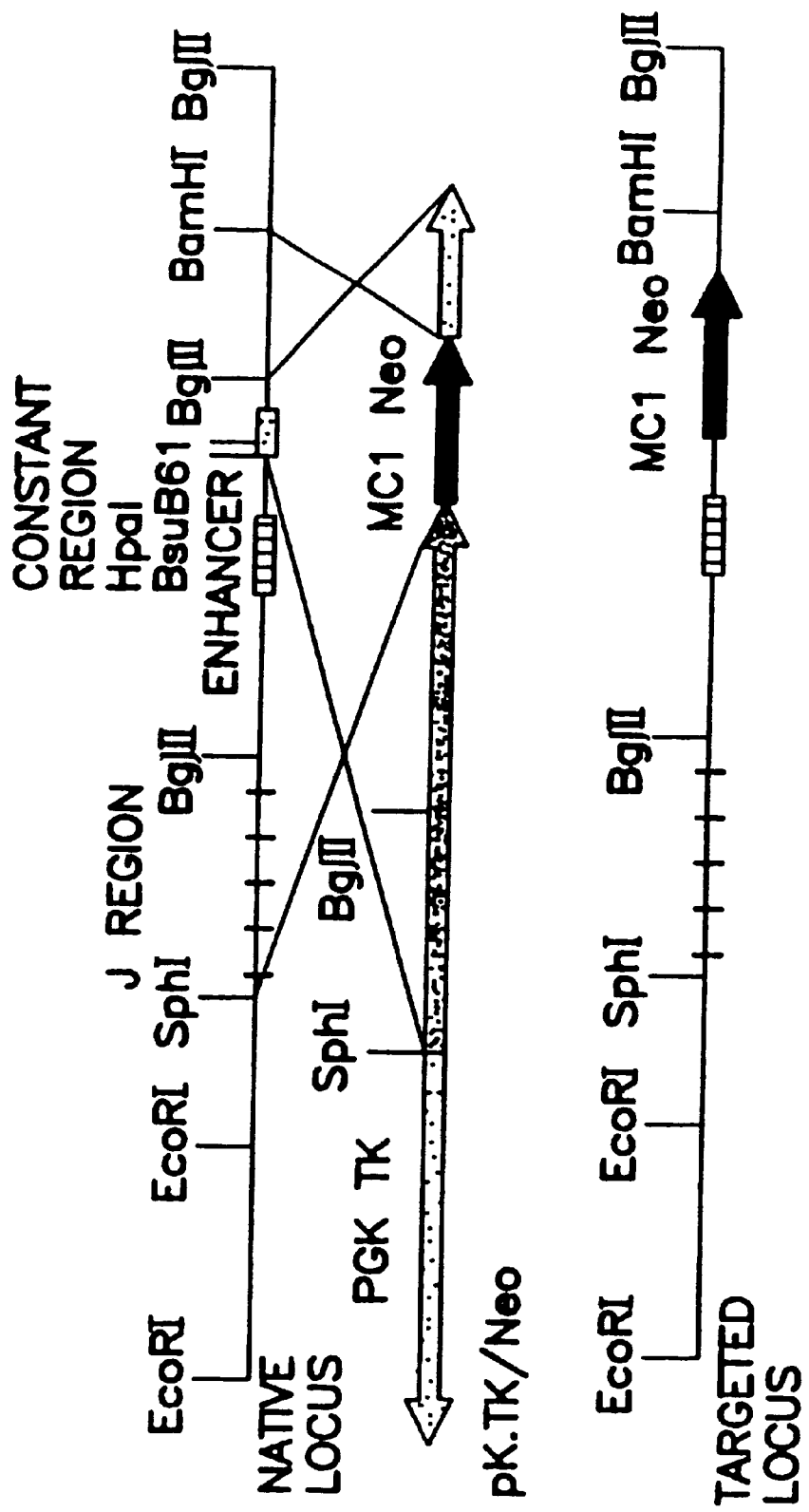
FIG. 5 is a diagram of the inactivation vector for the mouse immunoglobulin kappa constant region genes, as described in Example III, infra.

Homologous recombination was driven by regions of homology which flank the constant region (see FIG. 5).

A genomic library from 129/Ola mouse fetal liver DNA (Stratagene) cloned into lambda phage was screened for the presence of the mouse $C_k$ gene with a 1.6 kb HpaI/BamHI fragment (Steinmetz and Zachau (1980) Nucleic Acids Research 8:1693–1706) that spans the mouse kappa constant region. A lambda phage clone which hybridized to this probe was identified, then purified and used as a source of $C_k$ DNA. Analysis of the phage DNA showed that the kappa constant region probe hybridized to a 5.6 kb SphI/BamHI fragment. This fragment contained the kappa J region genes, an intronic enhancer element and the kappa constant region. It was then isolated and subcloned into the SphI and BamHI sites of the plasmid pUC218 to give the plasmid pUC218/5.6kappa.

Figure 6:
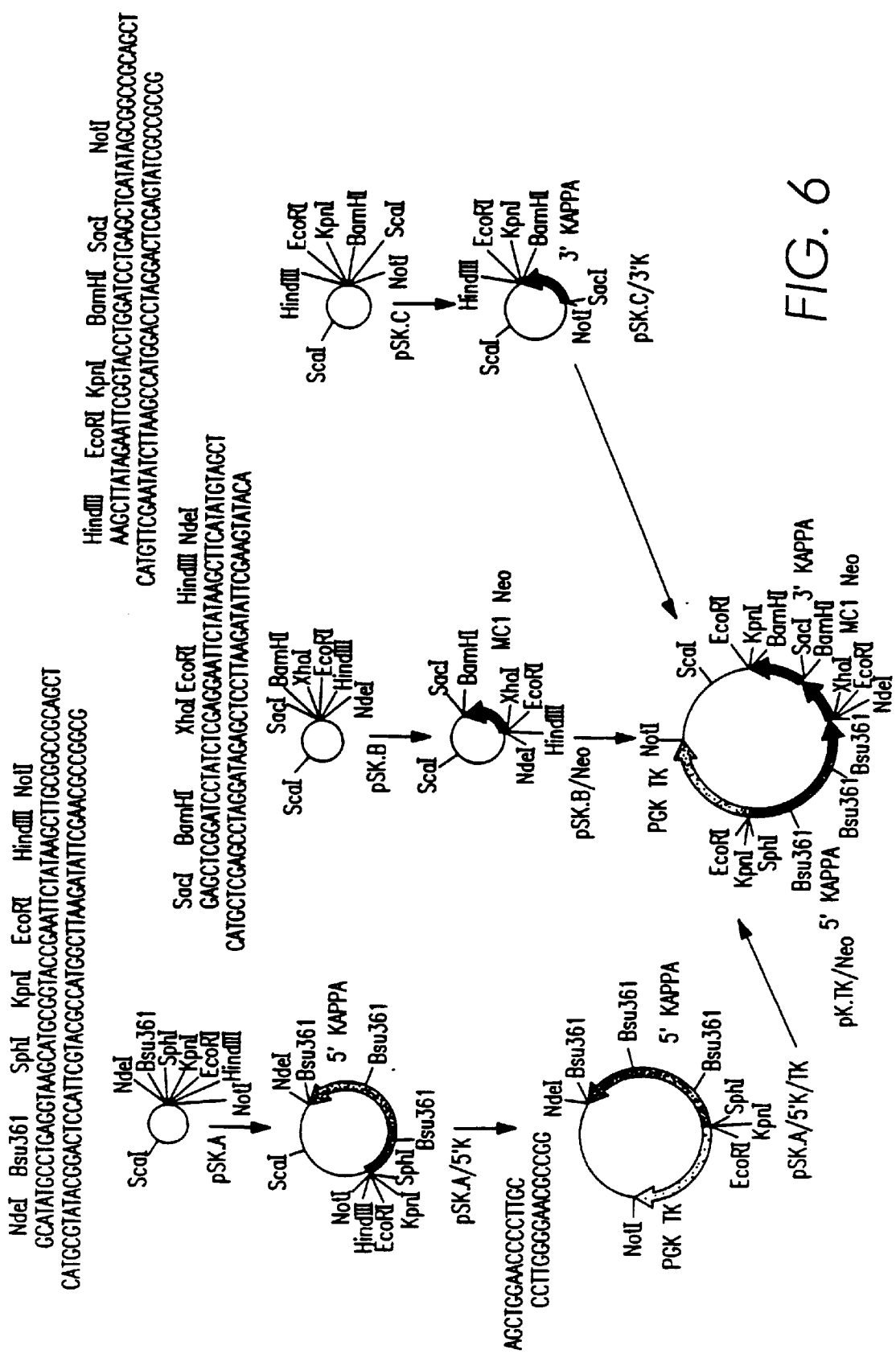
FIG. 6 is a diagram of the derivation of the plasmid pK.TK/Neo, as described in Example III, infra. The Figure dipicts the synthetic polylinker of plasmid pSK.A (SEQ ID NOS: 5 and 6); the synthetic polylinker of plasmid pSK.B (SEQ ID NOS: 8 and 9) and the synthetic polylinker of pSK.C (SEQ ID NOS: 10 and 11). As illustrated, a 4.0 kb SphI/Bsu361 fragment from the plasmid pUC218/5.6 kappa is sublconed into the sphI and Bsu361 sites of the vector pkA to produce plasmid pSK.A/5'K. A 2.7 Kb EcoRI/HindIII fragment containing the herpes thymidine kinase (TK) gene driven by the mouse phosphoglycerate kinase gene (PGK) promoter is inserted into pSK.A/5'K using an adapter (SEQ ID NO: 7) to produce plasmid pSK.A/5'K/TK.

In order to construct the deletion vector, fragments containing the 5' region of the kappa constant region, a thymidine kinase gene for negative selection, a neomycin resistance gene and a 3' region of homology to the kappa constant region were ligated together (see FIG. 6).

A 4.0 kb SphI/Bsu361 fragment from the plasmid pUC218/5.6kappa was subcloned into the SphI and Bsu361 sites of the vector pSK.A to give the plasmid pSK.A/5'K. The vector pSK.A is a modification of pBluescript SK- which has a synthetic polylinker:

5' GCATATGCCTGAGGTAAGCATGCGGTACCGAATTCTATAAGCTTGCC
GCCGCAGCTCATGCGTATACGGACTCCATTCGTACGCCATGGCTTAAGAT
ATTCGAACGCCGGCG 3' inserted between the pBluescript KpnI and SacI sites.

A 2.7 kb EcoRI/HindIII fragment containing the herpes thymidine kinase (TK) gene driven by the mouse phosphoglycerate kinase gene (PGK) promoter from the plasmid pKJtk (Tybulewicz, et al. (1991) Cell 65:1153–1163) was inserted into the EcoRI and NotI sites of pSK.A/5'K by using a HindIII/NotI adapter with the sequence:

5, AGCTGGAACCCCTTGCCCTTGGGGAACGCCGG 3'
(SEQ ID NO: 7).

In the resulting plasmid, pSK.A/5'K/TK, the 5' end of the TK gene and the kappa constant region gene are adjacent to each other, in opposite transcriptional orientations.

A 1.1 kb XhoI/BamHI fragment from pMC1Neo, which contains the mammalian drug selectable marker for resistance to neomycin, was cloned into the XhoI and BamHI sites of the plasmid pSK.B to give the plasmid pSK.B/Neo. The vector pSK.B is a modification of pBluescript SK- which has a synthetic polylinker:

5' GAGCTCGGATCCTATCTCGAGGAATTCTATAAGCTTCATATGTAGCT
CATGCTCGAGCCTAGGATAGAGCTCCTTAAGATATTCGAAGTATACA 3' inserted between the pBluescript KpnI and SacI sites.

A 1.1 kb BglII/BamHI fragment from pUC218/5.6kappa, which contains homology to the 3' end of the kappa region, was cloned into BamHI digested, alkaline phosphatase treated pSK.C vector. The vector pSK.C is a modification of pBluescript SK- which has a synthetic polylinker:

```
5' AAGCTTATAGAATTCGGTACCTGGATCCTGAGCTCATAGCGGCCGCA
GCTCATGTTCGAATATCTTAAGCCATGGACCTAGGACTCGAGTATCGCC
GGCG 3'
``` inserted between the pBluescript KpnI and SacI sites. The resulting plasmid, pSK.C/3'K is oriented such that transcription proceeds from the SacI site in the plasmid polylinker in the direction of the KpnI site.

The final targeting plasmid was constructed with a three part ligation, using (A) 6.1 kb NotI/NdeI fragment from pSK.A/5'K/TK, (B) 1.2 kb NdeI/SacI fragment from pSK.B/Neo and (C) 4.0 kb SacI/NotI fragment from pSK.C/3'K ligated to make the plasmid pK.TK/neo.

B. Electroporation of kappa deletion vector into ES cells

Purified plasmid DNA from pK.TK/Neo was cut with PvuI, extracted with phenol/chloroform and ethanol precipitated. The DNA was resuspended after precipitation at a concentration of 1 mg/ml in 10 mM Tris-HCl, 1 mM EDTA.

The embryonic stem cell line E14-1, a subclone of E14 (Hooper, et al. (1987) Nature 326:292–295) was cultured in DMEM 4.5 g/l glucose (J.R.H. Biosciences) supplemented with 15% heat inactivated fetal calf serum, recombinant murine leukemia inhibitory factor (ESGRO from Gibco BRL, 1000 U/ml), 0.1 mM β-mercaptoethanol, 2 mM glutamine and 100 U/ml penicillin at 37° C. in 5% $CO_2$.

The cells were cultured on mitomycin-treated primary embryonic fibroblast feeder layers essentially as described (Koller and Smithies (1989) supra). The embryonic fibroblasts were prepared from day 14 embryos carrying the homozygous targeted mutation of β2-microglobulin (Koller and Smithies (1990) Science 248:1227–1230). These feeder cells are capable of growth in media containing G418.

At 80% confluency, the ES cells were prepared for electroporation by trypsinization, concentration by brief centrifugation and resuspension in HEPES-buffered saline at $2 \times 10^7$ cells/ml. The cells are equilibrated at room temperature, and linearized targeting vector DNA (20 μg) added. The mixture was electroporated at 960 μF and 250 V with a BioRad Gene Pulser. The cells were left to stand at room temperature for 10 minutes before plating onto 4×10 cm dishes of mitomycin-treated fibroblast feeders ($3 \times 10^6$ feeder cells/plate). After incubation at 37° C. for 48 hours, the cells were fed media containing 150 μg/ml G418 to select for neomycin resistance. After a further 48 hours the cells were fed media containing 150 μg/ml G418 and 2 μM gancyclovir (Syntex) to select for loss of the thymidine kinase gene.

C. Analysis of targeted ES cells

After ten days of drug selection with both G418 and gancyclovir, the individual surviving colonies were picked and dissociated with a drop of trypsin in a 96 well plate, then incubated at 37° for 2 minutes. The cells from each colony were transferred into a well of a 24-well plate containing mitomycin C-treated feeder cells and selective media with G418, but not gancyclovir. After an additional 5–8 days, 20% of the cells in each well were frozen, and the remainder used to prepare genomic DNA. The cells were lysed with 0.4 ml of 10 mM Tris-HCl (pH 7.5), 100 mM NaCl, 10 mM EDTA, 1% SDS and proteinase K (1 mg/ml) by overnight incubation at 50° C. The DNA was purified by phenol extraction and ethanol precipitation, then washed with 70% ethanol and resuspended in 20 μl of 10 mM Tris-HCl, 1 mM EDTA.

Southern analysis was carried out using BglII digested genomic DNA from each sample. An about 1.2 kb BamHI/BglII fragment which contains the region contiguous with the 3' homology fragment in the targeting vector was used as a probe. The native ES cell locus gave an about 2.3 kb fragment, while the targeted ES cell locus gave an about 5.7 kb fragment. The increase in size is due to the loss of a BglII site during the construction of the deletion vector.

A Southern analysis of 166 clones showed two cell lines which had the intended mutation. These clones were further analyzed by reprobing the filters with an about 1.1 kb fragment which spans the neo gene. As expected, the probe only hybridized to the targeted allele.

Figure 7:
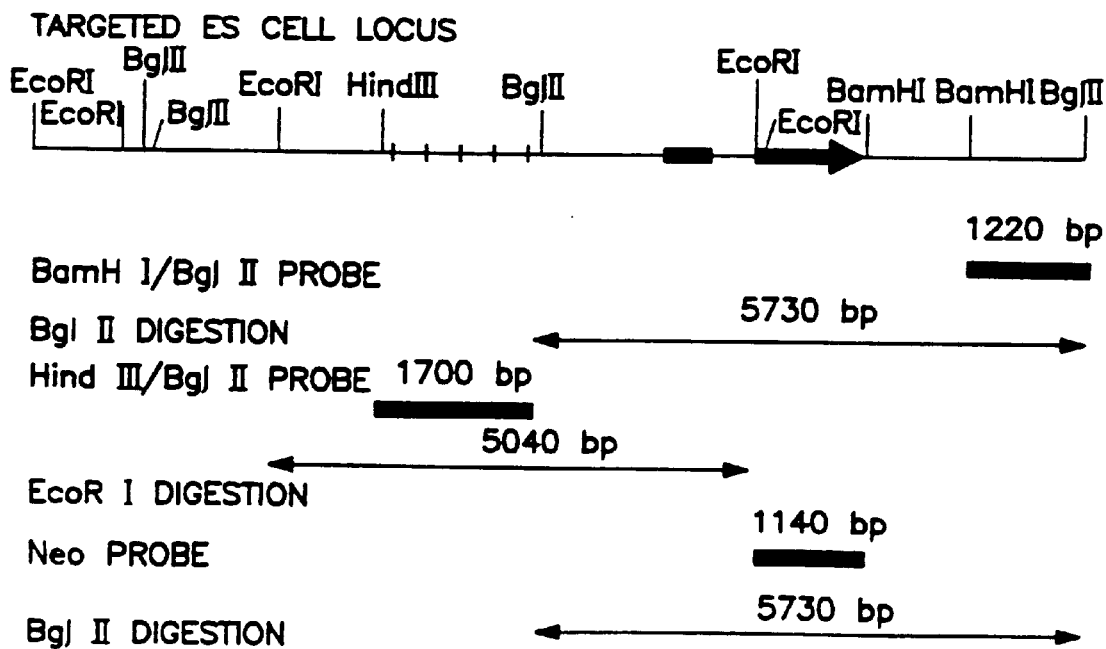
FIG. 7 is a diagram of the restriction map of the light chain targeted locus, as described in Example III, infra.

Further analysis of the genomic DNA from the two positive clones, 1L2-850 and 1L2-972, after being thawed and expanded, reconfirmed the initial observations. A third probe, an about 1.7 kb HindIII/BglII fragment spanning the kappa J region locus, was used to check for the correct integration pattern from the 5' end of the targeting vector. Using this probe with EcoRI digested genomic DNA, an about 15 kb fragment is detected in the native allele, and an about 5 kb fragment from the targeted locus. The additional EcoRI site is introduced by the neo gene during homologous recombination targeting (see FIG. 7).

D. Generation of germline chimeras

The unmodified E14-1 cells have been found to contribute to the germline at a high frequency after injection into C57BL/6J blastocysts. To generate germline chimeras containing the targeted kappa region, the targeted cell lines 1L2-850 and 1L2-972 were grown on primary feeder cells, then trypsinized and resuspended in injection medium, which consists of DMEM supplemented with 15% fetal calf serum, 20 mM HEPES (pH 7.3), antibiotics and β-mercaptoethanol. The ES cells were injected into each blastocyst, and the injected blastocysts then transferred to one uterine horn of a pseudopregnant female mouse. Chimeric pups were identified by chimeric coat color. Chimeric males were bred to C57BL/6J females, and germline transmission of the 129/Ola derived ES cells was detected by agouti coat color of the offspring.

One chimeric male from cell line 1L2-972 (about 40% ES cell derived as judged by its coat color), upon mating with C57B1/6J females yielded germline transmission at a frequency of 25% as determined by the percent of agouti offspring. Chimeric males, about 40%, 70% and 90% chimeric, from cell line 1L2-850 yielded germline transmission at a frequencies of 90%, 63% and 33%, respectively. Among the agouti offspring generated from the 70% chimeric male from 1L2-850, eight F1 animals out of 12 tested were found to be heterozygous at the kappa locus for the targeted $C_K$ mutation by Southern analysis (a Bgl II digest using the 1.2 kb Bam HI/Bgl II fragment described above as a probe) using genomic DNA derived from tail samples. Further breeding of a male and female from this group of 8 F1 animals, both heterozygous for the $C_K$ mutation, yielded one male offspring found to be homozygous for this mutation as confirmed by Southern analysis.

E. Analysis of B cells obtained from mice targeted at the kappa locus

If the kappa (κ) light chain locus is inactivated because of deletion of the light chain constant region (Cκ), the joining region(Jκ), or both Cκ and Jκ, then a complete block in the development of κ-expressing B cells should result. Mouse embryonic stem cells containing a single copy of the complete Cκ deletion (ΔCκ) were introduced into mouse blastocysts as described above to produce chimeric mice. These chimeric mice were then bred with wild-type C57BL/6 (B6) mice, and the F1 progeny were assayed for the presence of the ΔCκ mutation by Southern blotting of tail DNA. F1 mice that carried the ΔCκ mutation were bred and F2 offspring were assayed similarly for ΔCκ. One of 5 F2 offspring was shown to carry a homozygous Cκ deletion, and another was heterozygous, bearing both ΔCκ and a wild-type Cκ allele. The 3 other offspring were wild-type. The presence or absence of κ-positive B cells was assayed by flow cytometric analysis of peripheral blood B cells stained with fluorescent antibodies that react with a pan-B cell marker (B220) or with the κ K light chain. For the homozygous ΔCκ F2 mouse no κ-positive B cells were detected, and in the heterozygote, there was a reduction in the frequency of κ positive B cells, consistent with the presence of a wild-type allele and a non-functional ΔCκ allele. These results demonstrate that deletion of Cκ from the chromosome prevents κ expression by mouse B cells.

Figure 8:
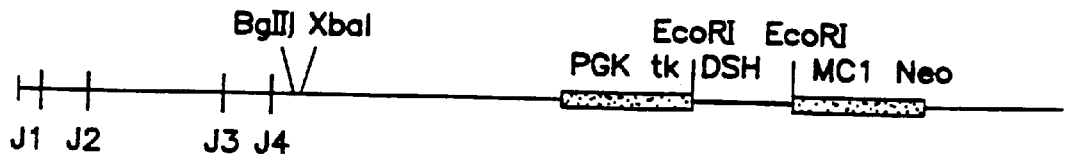
FIG. 8 is a diagram of the targeting vector for inactivation of the kappa light chain J and constant regions and design of the targeting experiment as described in Example IV, infra.
Figure 8:
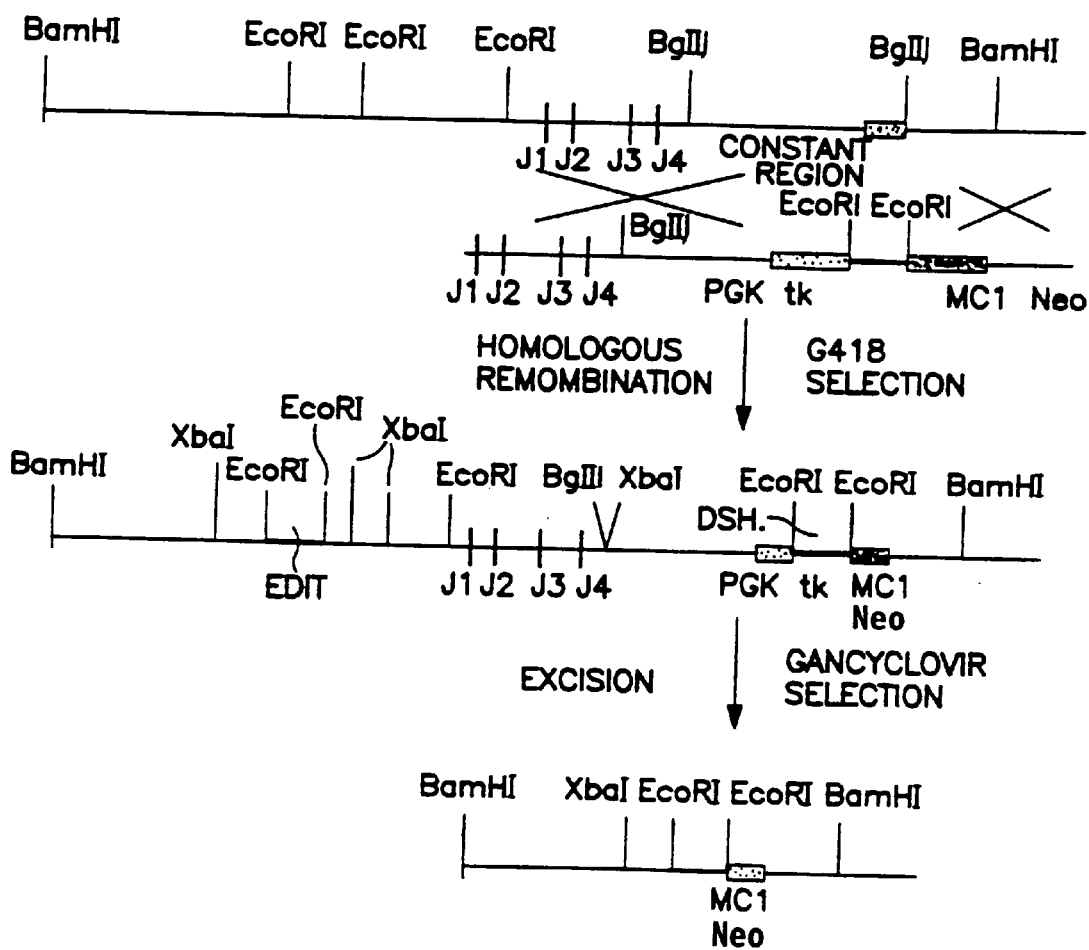

EXAMPLE IV
Inactivation of the mouse immunolobulin kappa light chain J and constant region A. Design of the targeting experiment The targeting vector was designed as a replacement type vector initially to delete the constant region as well as the J region of the kappa locus and replace it with three elements through homologous recombination using regions of homology flanking the constant region (FIG. 8). A diphtheria toxin gene (A chain) flanking either or both regions of homology was included in some cases as a negative selectable marker. The three elements consisted of the G418 resistance drug marker, an additional DNA homology (ADH) sequence of mouse DNA homologous to a region of the kappa locus located upstream of the J region, and a thymidine kinase gene. As a result of the inclusion of the ADH sequence in the vector, this initial targeting placed a second copy of the ADH in the locus. This duplication was then used to effect a defined deletion of the sequences between the segments by applying selective pressure. In this case the cell deletes the thymidine kinase gene that lies between the two segments in order to survive gancyclovir selection.

B. Construction of the targeting vector

The regions of homology were derived from a 129 mouse fetal liver genomic library (Stratagene) which was screened using two probes, as described above in Example III. This subclone contained the J region, an intronic enhancer element and the constant region of the kappa light chain locus. The second probe was a 0.8 kb EcoRI fragment (Van Ness et al. (1981), Cell 27:593–602) that lies 2.8 kb upstream of the J region. Phage DNA from a lambda clone positive for this probe showed that the probe hybridized to a 5.5 kb SacI fragment which was subcloned into the SacI site of pBluescript SK (Stratagene) to give the plasmid pSK.5'kappa (FIG. 8).

The inactivation vectors which contained a 5' region of homology, a thymidine kinase gene, a ADH, a neomycin resistance gene and a 3' region of homology (FIG. 9) flanked in some instances by diphtheria toxin genes were constructed from three plasmids (FIG. 8) containing: (a) the 5' fragment of homology with or without the diphtheria toxin gene (DT) driven by the mouse phosphoglycerate kinase gene (PGK) promoter as a negative selectable marker, (b) the herpes thymidine kinase gene (tk) driven by the mouse phosphoglycerate kinase gene (PGK) promoter as a negative selectable marker along with the DSH and the G418 selectable neomycin (neo) gene from pMC1Neo (Thomas and Capecchi (1987), Cell 51:503–12), and (c) the 3' fragment of homology with or without the PGK driven DT gene. These three plasmids (FIG. 8) were constructed from pSK.A, pSK.B, and pSK.C, respectively, all derived from the plasmid pBluescript SK by modification of the polylinker.

The polylinker of the plasmid pBluescript SK- was modified by cloning between the KpnI and SacI sites a synthetic polylinker defined by the oligonucleotides 5'-GCATATGCCTGAGGGTAAGCATGCGGTACCGAAT TCTA TAAGCTTGCGGCCGCAGCT-3' (SEQ ID NO: 5) AND 5'-GCGGCCGCAAGCTTATAGAATTC GGTACCGCATGCTTACCTCAGGCATATGCGTAC-3' (SEQ ID NO: 6) to create the plasmid pSK.A, 5'-GAGCTCGGATCCTATCTCGAGGAATTCTATAAGC TTCATATGT AGCT-3' (SEQ ID NO: 8) and 5'-ACATATGAAGCTTATAGAATTCCTCGAGATAGGAT CCHA GCTCGTAC-3' (SEQ ID NO: 9) to create plasmid pSK.8, 5'-AAGCTTATAGAATTCGGTACC TGGATCCTGAGCTCATAGCGGCCGCAGCT-3' (SEQ ID NO: 10) to create plasmid psK.B and 5'-GCGGCCGCTATGAGCTCAGGATCCAGGTACCGAA TTCTATAAGCTTG TAC-3' (SEQ ID NO: 11) to create the plasmid pSK.C.

A diphtheria toxin gene cassette was created in which the gene was flanked by the PGK promoter and the bovine growth hormone polyadenylation signal (Woychik et al. (1984), Proc. Natl. Acad. Sci. U.S.A, 81:3944–3948; Pfarr et al. (1986), DNA 5:115–122). A 2.3 kb XbaI/EcoRI fragment from pTH-1 (Maxwell et al. (1986), Cancer Res. 46:4660–4664) containing the diphtheria toxin A chain driven by the human metallothionein (hMTII) promoter was cloned into pBluescript SK- cut with XbaI and EcoRI to give the plasmid pSK.DT. The hMTII promoter of pSK.DT was replaced with the PGK promoter from pKJ1 (Tybulewicz et al. (1991), Cell 65:1153–1163). A 0.5 kb XbaI/PstI fragment from pKJ1 was joined to a 3.1 kb XbaI/NcoI fragment from pSK.DT using a PstI/NcoI adapter formed from the oligonucleotides 5'-GGGAAGCCGCCGC-3' (SEQ ID NO: 12) and 5'-CATGGC GGCGGCTTCCCTGCA-3' (SEQ ID NO: 13) to give the plasmid pSK.pgkDT. A 248 bp fragment containing the bovine growth hormone polyadenylation signal, obtained by PCR amplification of bovine genomic DNA using the oligonucleotide primers 5'-CAGGATCCAGCTGTGCCTTCTAGTTG-3' (SEQ ID NO: 14) and 5'-CTGAGCTCTAGACCCATA GAGCCCACCGCA-3' (SEQ ID NO: 15), was cloned into pCR1000 (Invitron Corp., San Diego, Calif.). The polyadenylation sequence was then cloned behind the DT gene as a HindIII/PvuII fragment into pSK.pgkDT cut with HindIII and HpaI to give the plasmid pSK.pgkDTbovGH. The DT gene cassette from pSK.pgkDTbovGH was moved as a 2.1 kb EcoRI/HindIII fragment into pSK.A cut with EcoRI and NotI using a HindIII/NotI adapter formed from the oligonucleotides 5'-AGCTGGAACCCCTTGC-3' (SEQ ID NO: 16) and 5'-GGCCGCAAGGGGTTCC-3' (SEQ ID NO: 17) to give the plasmid pSK.A/DT. Between the SphI and Bsu36I sites of both pSK.A and pSK.A/DT the 5' region of homology for the kappa locus was cloned. For this purpose a 4.0 kb SphI/Bsu361 fragment resulting from a partial Bsu36I digest followed by a complete SphI digest of plasmid subclone pUC218/5.6kappa was ligated to pSK.A or pSK.A/DT to give the plasmids pSK.A/5'K and pSK.A/DT/ 5'K, respectively. In the plasmid, pSK.A/DT/5'K, the 5'-end of the DT gene and kappa fragment were adjacent to each other running in the opposite transcriptional orientations.

The PGKtk gene from the plasmid pKJtk (Tybulewicz et al. (1991), Cell 65:1153–1163) was cloned as a 2.7 kb EcoRI/HindIII between the unique EcoRI and HindIII sites of pSK.B to give pSK.B/TK. A 0.8 kb EcoRI fragment used for the ADH was cloned from pSK.5'kappa and was ligated into the EcoRI site of pSK.B/TK to give pSK.B/(TK/0.8K) such that the 5'-end of the tk gene and kappa fragment were adjacent to each other running in opposite transcriptional orientations. The 1.1 kb neo gene from pMC1Neo was cloned as an XhoI/BamHI fragment between the same sites of pSK.B/(TK/0.8K) to give pSK.B/(TK/0.8K/Neo). The plasmid pSK.C/3'K containing the 3' fragment of homology was constructed by ligating pSK.C digested with BamHI and treated with alkaline phosphatase to the 1.1 kb BglII/BamHI fragment isolated from pUC218/5.6kappa. In pSK.C/3'K, the kappa fragment was oriented such that transcription proceeded from the SacI in the plasmid polylinker in the direction of the KpnI site. The 2.1 kb DT cassette from pSK.pgkDTbovGH was cloned as an EcoRI/HindIII fragment into the same sites of pSK.C to give pSK.C/3'K/DT.

Figure 9A:
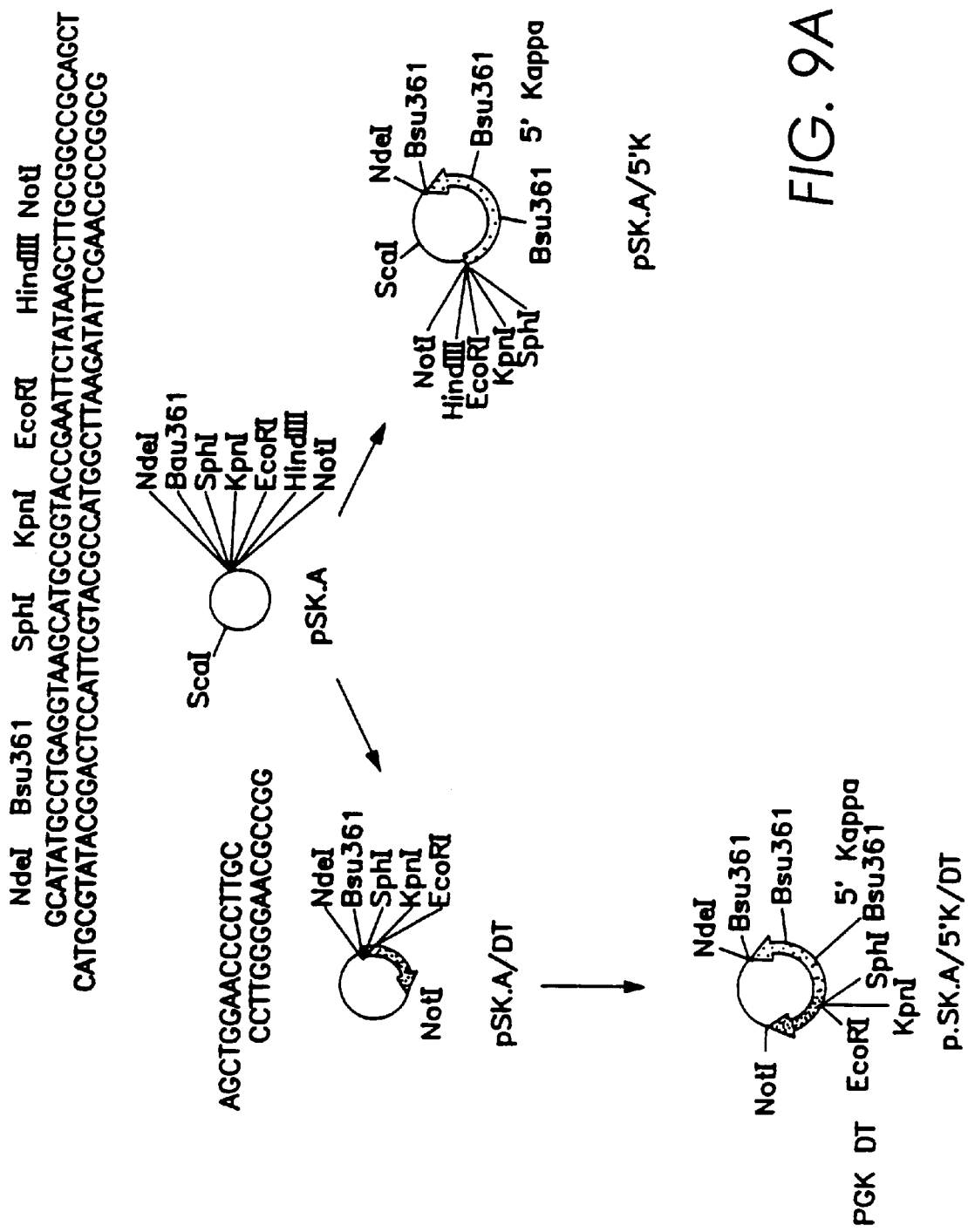
FIG. 9A illustrates the synthetic polylinker of pSK.A illustrates the synythetic polylinker of pSK.A (SEQ ID NOS: 5 and 6). A diptheria toxin A chain gene driven by a PGK promoter are inserted into pSK.A using an adapter (SEQ ID NOS: 12 and 13).
Figure 9B:
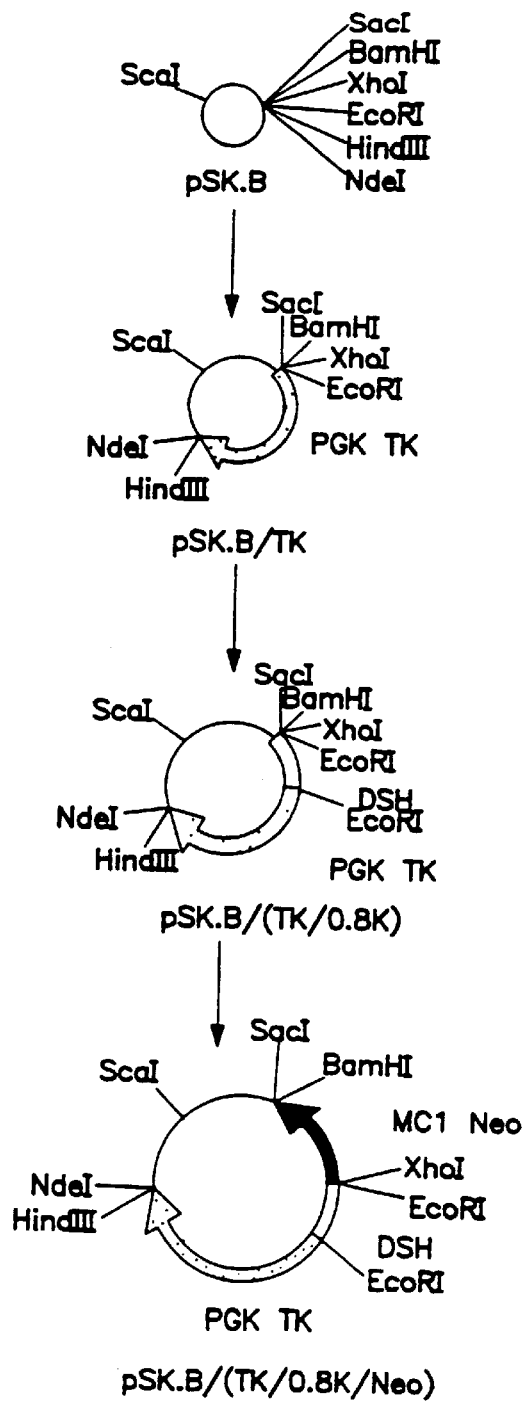
FIG. 9B illustrates the synthetic polylinker of pSK.B (SEQ ID NOS: 8 and 9).
Figure 9C:
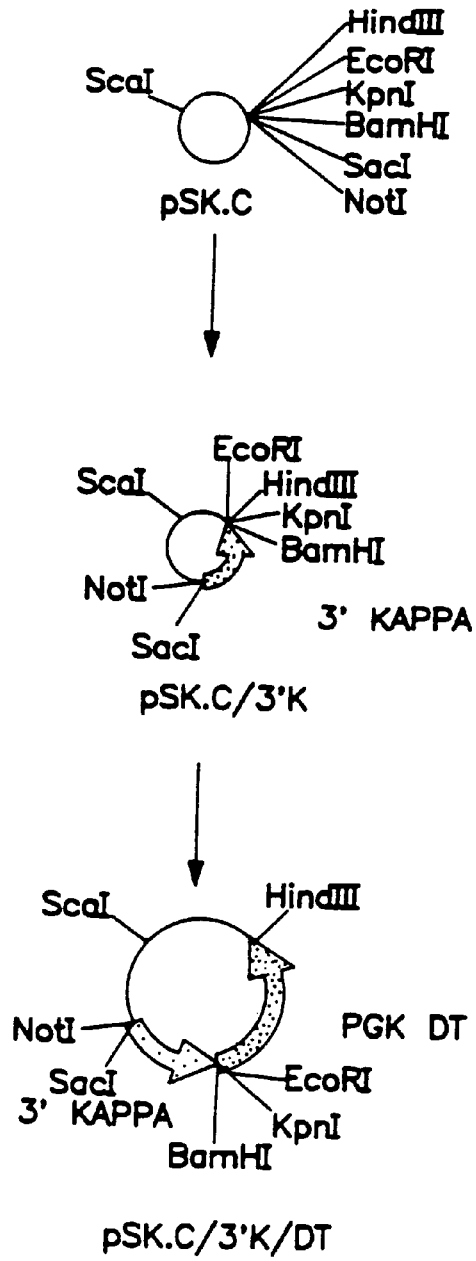
FIG. 9C illustrates the synthetic polylinker of pSK.C (SEQ ID NOS: 10 and 11).
Figure 10:
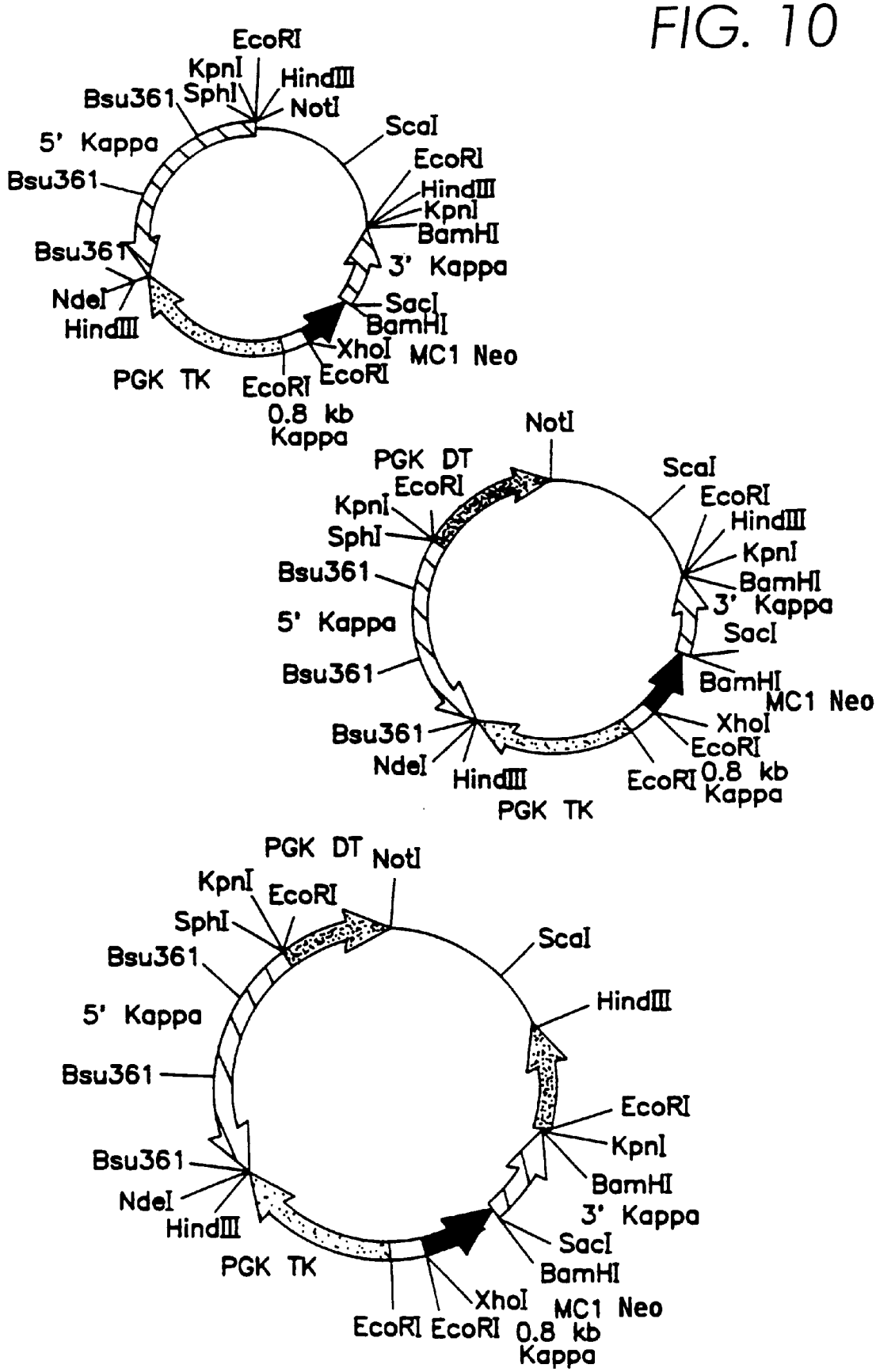
FIG. 10 is a diagram of the final deletion vectors for inactivation of the kappa light chain J and constant regions as described in Example IV, infra.

Three-part ligations were carried out to construct the final targeting plasmids (FIG. 9). The 4.0 kb NotI/NdeI fragment from pSK.A/5'K, the 4.8 kb NdeI/SacI fragment from pSK.B/(TK/0.8K/Neo) (obtained by a SacI partial followed by and NdeI digestion of the plasmid), and the 4.0 kb SacI/NotI fragment from pSK.C/3'K were isolated and ligated together to create pK. (TK/0.8K/Neo). The 6.1 kb NotI/NdeI fragment from pSk.A/DT/5'K, the 4.8 kb NdeI/SacI fragment from pSK.B/(TK/0.8K/Neo), and 4.0 kb SacI/NotI fragment from pSK.C/3'K were isolated and ligated together to create pK.DT/(TK/0.8K/Neo). The 6.1 kb NotI/NdeI fragment from pSK.A/DT/5'K, the 4.8 kb NdeI/SacI fragment from pSK.B/(TK/0.8K/Neo), and 6.1 kb SacI/NotI fragment from pSK.C/3'K/DT (obtained by a SacI partial followed by a NotI digestion of the plasmid) were isolated and ligate together to create pK.DT/(TK/0.8K/Neo)/DT. For electroporation, the purified plasmid DNAs were first cut with PvuI or ApaLI, then extracted with phenol/chloroform and precipitated by the addition of ethanol before centrifugation. The resultant DNA pellets were resuspended at a concentration of 1 mg/ml in 10 mM Tris-HCl, 1 mM EDTA(TE).

C. Introduction of DNA into cells

The embryonic stem cell line E14-1 was cultured as described above in Example III. The cells were equilibrated at room temperature, and DNA (20 μg) linearized with PvuI (as described above) was added. The mixture was electroporated as described above in Example III.

D. Analysis of constant region-targeted ES cells

After 7–10 days under drug selection with G418, the individual surviving colonies were each picked and dissociated in a drop of trypsin as described above in Example III.

Southern analysis was carried out using BglII digested genomic DNA from each sample. A 2.3 kb fragment was detected from the native ES cell locus, while a larger 4.9 kb fragment was detected from a targeted ES cell locus (FIG. 11), using as a probe the 1.2 kb BamHI/BglII fragment isolated from the original phage DNA contiguous with the fragment used for the 3' homology in the targeting vector. The fragment increased in size because the BglII site in the BglII/BamHI fragment was lost in the targeting plasmid due to the joining of a BglII site to a BamHI site in the ligation, and a new BglII site located in the thymidine kinase gene is introduced into the targeted locus.

From a screen by the Southern analysis described above, of a total of 103 clones derived from experiments using three different targeting plasmids, 5 cell lines were identified which carried the intended mutation (Table 1).

TABLE 1

$C_K$ Light Chain Targeting Result in E14-1

| Construct | Number Screened by Southern | Number of Confirmed Targeted Clones | Clone Designation | Frequency of Targeting |
|---|---|---|---|---|
| pK.(TK/0.8K/Neo) | 44 | 2 | 625,691 | 1/22 |
| pK.DT(TK/0.8/Neo) | 42 | 2 | 604,611 | 1/21 |
| pK.DT(TK/0.8K/Neo)DT | 17 | 1 | 653 | 1/17 |

Figure 11:
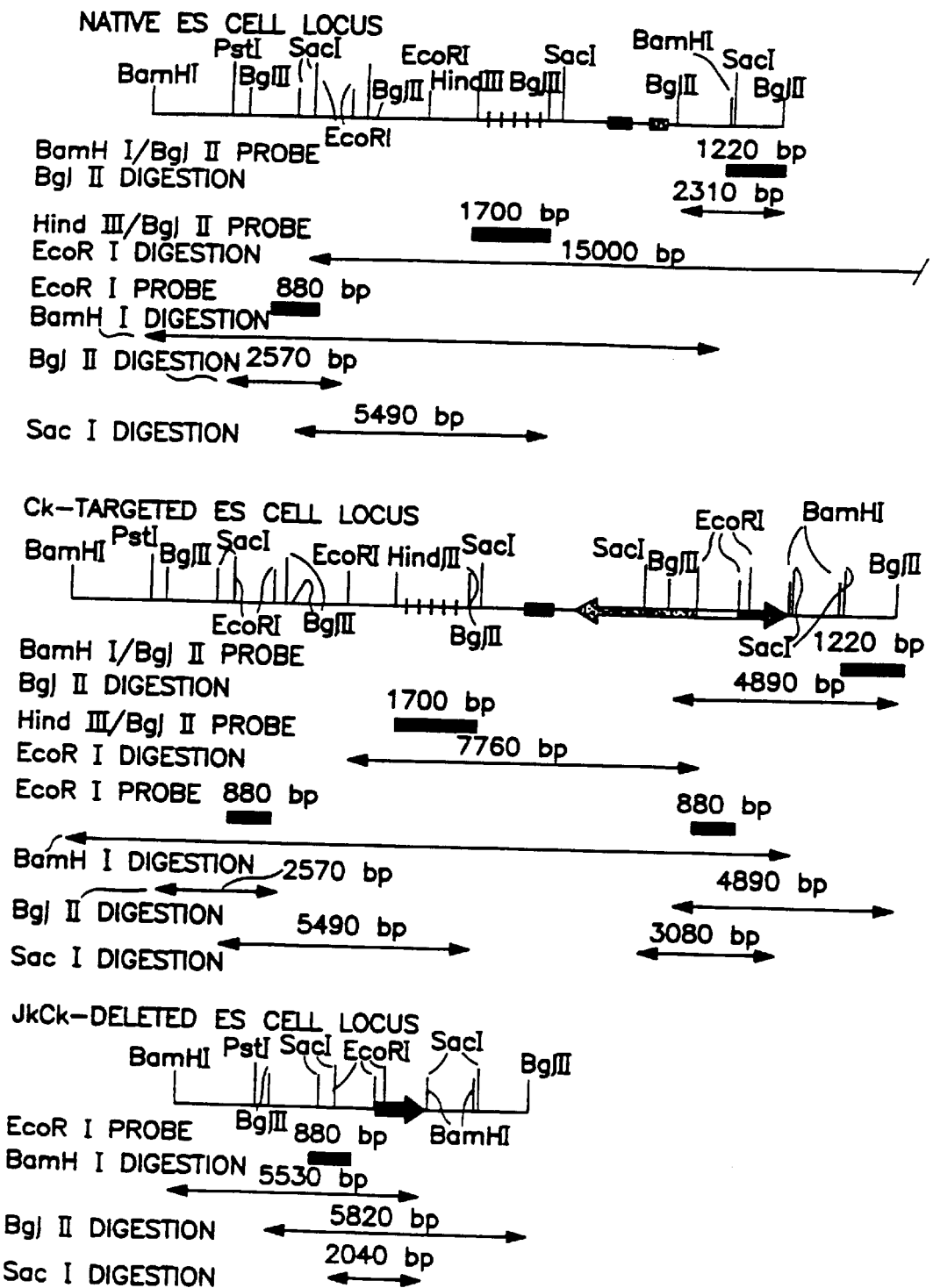
FIG. 11 is an illustration of the Southern analysis of light chain J and constant region deleted cells as described in Example IV, infra.

Further analysis of genomic DNA produced from 4 of the positive clones (clones 625, 604, 611 and 653) after being thawed and expanded, re-confirmed the initial observations. Using a second probe, a 1.7 kb HindIII/BglII fragment which spanned the J region of the kappa locus, the correct integration pattern was checked for homologous targeting at the 5' end of the targeting vector. Thus, using this probe with an EcoRI digest of the genomic DNA, a 15 kb fragment was detected from the unmodified allele. In contrast, a 7.8 kb fragment from the targeted allele was observed as a result of the introduction of a new EcoRI site in the thymidine kinase gene during the homologous integration (FIG. 11).

E. In vitro excision of J region DNA from targeted clones

In order to effect the desired deletion from the homologously targeted kappa locus, cells from clone 653 were plated on feeder cells at a density of 0.5–1×10$^6$ cells/10 cm dish in the presence of both gancyclovir (2 μM) and G418 (150 μg/ml). After growth for 5 days in the presence of both drugs, clones were picked as described above into 24-well plates and grown under G418 selection alone. After an additional 5–8 days, 20% of the cells in each well were frozen and the remainder used to prepare genomic DNA as previously described.

F. Analysis of J/constant region deleted ES cells

Southern analysis was carried out using BamHI digested genomic DNA from each sample. Using as a probe the 0.8 kb EcoRI fragment used as the ADH in the targeting vectors, as 12.7 kb fragment was detected from the native ES cell locus, while a larger 15.8 kb fragment was detected from the constant region-targeted ES cell locus (FIG. 11) using DNA from clone 653. The fragment increased in size because of the insertion of the tk gene, the ADH, and the neo gene into the 12.7 kb BamHI fragment.

There was also a new BamHI site introduced at the 3' end of the neo gene. Using DNA from the J/constant region deleted cells, a 5.5 kb fragment was detected from the modified locus in addition to the 12.7 kb fragment from the untargeted allele as predicted from analysis of the restriction map. From this screen by Southern analysis of 2 clones produced from 1.5×10$^6$ ES cells plated (clone 653), one cell line (clone 653B) was identified which carried the intended deletion of the J and constant regions.

Further analysis of genomic DNA produced from clone 653B after being thawed and expanded re-confirmed the initial observations. Using the 0.8 kb EcoRI fragment, the deletion was checked with two other restriction digests which should cut outside of the excised region on the 5' and 3' ends of the targeting vector. Thus using this probe with a BglII digest of the genomic DNA from the unexcised clone 653, a 2.6 kb fragment was detected from both the unmodified and modified alleles, whereas an additional 4.9 kb fragment was observed from the targeted allele only (FIG. 11). This 4.9 kb fragment was the same as that detected with the 1.2 kb BamHI/BgIII fragment used previously. Using DNA from clone 653B, a BgIII digest revealed a 5.8 kb fragment in addition to the 2.6 kb fragment from the unmodified allele. A SacI digest of clone 653 DNA probed with the 0.8 kb EcoRI fragment showed a 5.5 kb fragment from both the unmodified and modified alleles and a 3.1 kb fragment from the targeted allele only (FIG. 11). The 5.5 kb fragment was also detected in DNA from clone 653B and an additional 2.0 kb fragment. The 5.8 kb BgIII fragment and the 2.0 kb ScaI fragment were consistent with an analysis of the predicted restriction map for a precise excision step in which 10.3 kb of DNA were deleted including the J region, the tk gene, and one copy of the ADH.

G. Generation of Germline Chimeras

The unmodified E14-1 cells contributed to the germline at a high frequency after injection into C57BL/6J blastocysts. The cells from the targeted ES cell line 691, in which only the kappa constant region has been deleted by homologous recombination without any negative selection, were microinjected and chimeric animals were produced as described above in Example III. Cells from the targeted ES cell line 653B in which both the kappa constant and J regions were deleted are also microinjected and chimeric animals are produced as described above. Chimeric pups are identified by chimeric coat color. Germline transmission of the modified ES cell is detected by the agouti coat color of the F1 offspring.

EXAMPLE V

Cloning of Human Heavy Chain Locus using Yeast Artificial Chromosomes

A. Production of Yeast Artificial Chromosome (YAC) containing human heavy chain

Figure 15A:
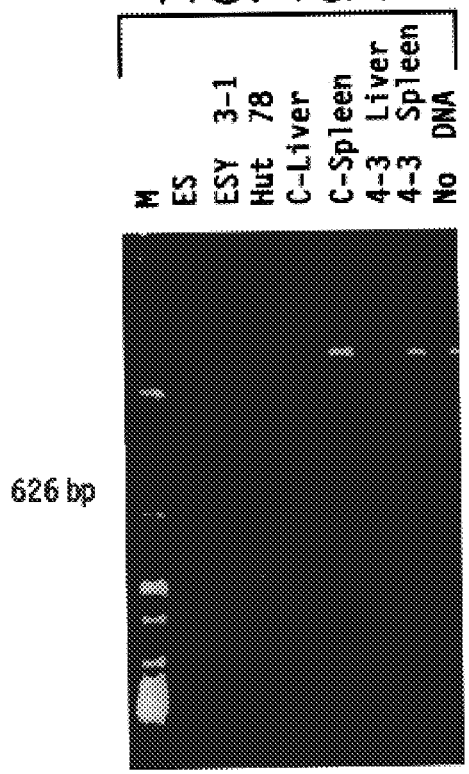
FIGS. 15 A and B are a photograph of an electrophoresis gel showing the expression of the human HPRT gene in various mouse tissues, as described in Example VI, infra (15 A=detection of human HPRT mRNA using reverse transcription-PCR in ES, ESY 3-1 and Hut 78 cells, spleen and liver from control mice or ESY 4-3 agouti offspring; 15 B=detection of mouse γ-interferon receptor mRNA by RT-PCR in samples from 15 A; M=size marker).
Figure 15B:
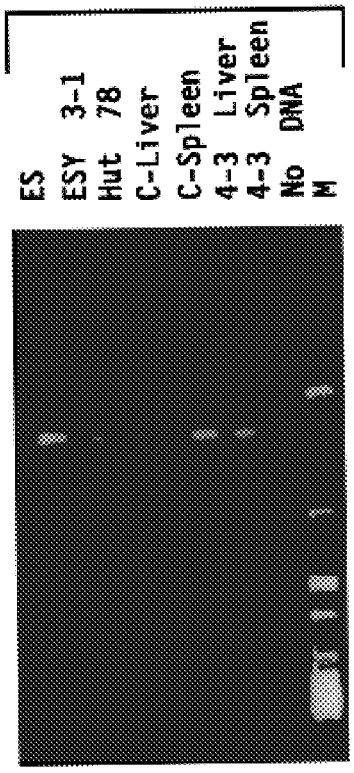

An SpeI fragment, spanning the human heavy chain VH6-D-J-C$\mu$-C$\delta$ region (Berman et al. (1988), *EMBO J.* 7: 727–738; see FIG. 15) is isolated from a human YAC library (Burke, et al., *Science*, 236: 806–812) using DNA probes described by Berman et al. (1988) *EMBO J.* 7:727–738. One clone is obtained which is estimated to be about 100 kb. The isolated YAC clone is characterized by pulsed-field gel electrophoresis (Burke et al., supra; Brownstein et al., *Science*, 244: 1348–1351), using radiolabelled probes for the human heavy chain (Berman et al., supra).

B. Introduction of YAC clones into embryos or ES Cells

High molecular weight DNA is prepared in agarose plugs from yeast cells containing the YAC of interest (i.e., a YAC containing the aforementioned SpeI fragment from the IgH locus). The DNA is size-fractionated on a CHEF gel apparatus and the YAC band is cut out of the low melting point agarose gel. The gel fragment is equilibrated with polyamines and then melted and treated with agarase to digest the agarose. The polyamine-coated DNA is then injected into the male pronucleus of fertilized mouse embryos which are then surgically introduced into the uterus of a psueudopregnant female as described above. The transgenic nature of the newborns is analyzed by a slot-blot of DNA isolated from tails and the production of human heavy chain is analyzed by obtaining a small amount of serum and testing it for the presence of Ig chains with rabbit anti-human antibodies.

As an alternative to microinjection, YAC DNA is transferred into murine ES cells by ES cell: yeast protoplast fusion (Traver et al., (1989) *Proc. Natl. Acad. Sci.*, USA, 86:5898–5902; Pachnis et al., (1990), ibid 87: 5109–5113). First, the neomycin-resistance gene from pMC1Neo or HPRT or other mammalian selectable marker and a yeast selectable marker are inserted into nonessential YAC vector sequences in a plasmid. This construct is used to transform a yeast strain containing the IgH YAC, and pMC1Neo (or other selectable marker) is integrated into vector sequences of the IgH YAC by homologous recombination. The modified YAC is then transferred into an ES cell by protoplast fusion (Traver et al. (1989); Pachnis et al., 1990), and resulting G418-resistant ES cells (or exhibiting another selectable phenotype) which contain the intact human IgH sequences are used to generate chimeric mice. Alternatively, a purified YAC is transfected, for example by lipofection or calcium phosphate-mediated DNA transfer, into ES cells.

EXAMPLE VI

Introduction of Human Ig Genes into Mice

A. Cloning of Human Ig Genes in Yeast

1. Identification and characterization of a human IgH YAC clone containing VH, D, JH, mu and delta sequences:

PCR primers for the human VH6 gene (V6A=5' GCA GAG CCT GCT GAA TTC TGG CTG 3' (SEQ ID NO: 18) and V6B=5' GTA ATA CAC AGC CGT GTC CTG G 3') (SEQ ID NO: 19) were used to screen DNA pools from the Washington University human YAC library (Washington University, St. Louis, Mo.). Positive pools were subsequently screened by colony hybridization and one positive microtiter plate well, A287-C10, was identified. Two different sized (205 kb and 215 kb) VH6-containing YACs were isolated from the microtiter well. In addition to VH6, the smaller of the two IgH YACs, A287-C10 (205 kb), hybridized to probes for the following sequences: delta, mu, JH, D, VH1, VH2, and VH4. The larger of the two IgH YACs, A287-C10 (215 kb), hybridized to the following probes: delta, JH, D, VH1, VH2, and VH4, but not to mu. The YACs contained sequences from at least 5 VH genes including two VH1 genes, one VH2, one VH4 and one VH6 gene. Analysis of restriction digests indicated that the 205 kb YAC contains a deletion (about 20 kb size) that removes some, but not all of the D gene cluster, with the remainder of the YAC appearing to be intact and in germline configuration. PCR and detailed restriction digest analysis of the 205 kb YAC demonstrated the presence of several different D gene family members. The 215 kb YAC appeared to contain the complete major D gene cluster but had a deletion (about 10 kb) that removed the mu gene. This deletion does not appear to affect the JH cluster or the enhancer located between JH and mu genes.

The putative progenitor of the above two related IgH YACs, a YAC of about 225–230 kb containing the entire genomic region between the VH2 gene and the delta gene (Shin et al., 1991, supra) (see FIG. 15), had not been identified in the A287-C10 microtiter well. Hence, an earlier aliquot of the A287-C10 microtiter plate well was examined in order to search for the progenitor YAC under the assumption that it was lost during passaging of the library. The A287-C10 microtiter well was streaked out (Washington University, St. Louis, Mo.), and 2 of 10 clones analyzed contained a 230 kb IgH YAC with another apparently unrelated YAC. Clone 1 contained in addition the IgH YAC, an approximately 220 kb YAC and clone 3 in addition contained an approximately 400 kb YAC. The IgH YAC contained mu, the complete D profile (based on a BamHI digest, see below) and JH. The IgH YAC from clone 1 was physically separated from the unrelated YAC by meiotic segregation in a cross between A287-C10/AB1380 and YPH857 (genotype=MATα ade2 lys2 ura3 trp1 HIS5 CAN1 his3 leu2 cvh2, to yield A287-C10 (230 kb)/MP 313 (host genotype=MATα ade2 leu2 lys2 his3 ura3 trp1 can1 cyh2).

2. Targeting of the A287-C10 kb YAC with a mammalian selectable marker, HPRT:

A YAC right arm targeting vector called pLUTO (15.6 kb) was generated by subcloning a human HPRT minigene contained on a 6.1 kb BamHI fragment (Reid et al., *Proc. Natl. Acad. Sci. USA* 87:4299–4303 (1990)) into the BanHI site in the polylinker of pLUS (Hermanson et al., *Nucleic Acids Research* 19:4943–4938 (1991)). A culture of A287-C10/AB1380 containing both the 230 kb IgH YAC and an unrelated YAC was transformed with linearized pLUTO and Lys+ transformants were selected. The Lys+ clones were screened by colony hybridization for the presence of mu. One clone was identified which contained a single YAC of approximately 245 kb which hybridized to probes for mu, HPRT and LYS2.

Southern analysis of the 230 kb A287-C10 YAC targeted with PLUTO was carried out using a variety of probes to demonstrate the intact, unrearranged nature of the cloned, human IgH sequences. In most cases, the results of BamHI, HindIII and EcoRI digests were compared to restriction data for WI38 (a human embryonic fetal lung-derived cell line), the 205 kb and 215 kb deletion-derivatives of A287-C10 and to published values. The diversity (D) gene profile determined by hybridization with a D region probe (0.45 NcoI/PstI fragment; Berman et al., 1988) demonstrated the expected four D gene segments (D1-D4 (Siebenlist et al., 1981; *Nature* 294:631–635). For example, with BamHI, four restriction fragments, 3.8 kb, 4.5 kb, 6.9 kb and 7.8 kb, were observed in A287-C10 and WI38. WI38 had one additional larger band, presumed to originate from the chromosome 16 D5 region (Matsuda et al., 1988, *EMBO* 7:1047–1051). PCR and Southern analysis with D family-specific primers and probes demonstrated in the 215 kb deletion-derivative YAC (which appeared to have an intact D region with the same restriction pattern as the 230 kb YAC) the presence of 2 to 4 members of each of the following D gene families: DM, DN, DK, DA, DXP and DLR. The J-mu intronic enhancer, which was sequenced from cloned PCR products from the A287-C10 230 kb YAC (primers EnA=5' TTC CGG CCC CGA TGC GGG ACT GC 3' (SEQ ID NO: 20) and EnB1=5' CCT CTC CCT AAG ACT 3') (SEQ ID NO: 21) and determined to be intact, also generated single restriction fragments of approximately the predicted sizes with BamHI, EcoRI and HindIII when probed with the 480 bp PCR product. The JH region was evaluated with an approximately 6 kb BamHI/HindIII fragment probe spanning DHQ52 and the entire JH region (Ravetch et al., 1981, *Cell* 27:583–591). A287-C10 generated restriction fragments of approximately the expected sizes. Furthermore, the same-sized restriction fragments were detected with the enhancer and the JH probes (Ravetch et al., supra; Shin et al., 1991, supra). The approximately 18 kb BamHI JH fragment detected in A287-C10 and WI38 also hybridized to a 0.9 kb mu probe sequence (Ravetch et al., supra). Hybridization with the 0.9 kb EcoRI fragment mu probe (Ravetch et al., supra) showed restriction fragments of approximately the expected sizes (Ravetch et al., supra; Shin et al., supra):>12 kb BamHI (approximately 17 kb expected); 0.9 kb EcoRI (0.9 kb expected) and approximately 12 kb HindIII (approximately 11 kb expected). WI38 gave the same-sized BamHI fragment as A287-C10. The JH and DHQ52 regions were sequenced from both of the deletion derivative YACs and both were in germline configuration. Delta was analyzed with an exon 1 PCR product (containing the approximately 160 bp region between primers D1B=5' CAA AGG ATA ACA GCC CTG 3' (SEQ ID NO: 22) and D1D=5' AGC TGG CTG CTT GTC ATG 3') (SEQ ID NO: 23); restriction fragments for A287-C10 were close to those expected from the literature (Shin et al., supra) and to those determined for WI38. The 3' cloning site of the YAC may be the first EcoRI site 3' of delta (Shin et al., supra) or another EcoRI site further 3'. VH gene probes for VH1, VH4 and VH6 (Berman et al., supra), and for VH2 (Takahashi et al., 1984, *Proc. Nat. Acad. Sci. USA* 81:5194–5198) were used to evaluate the variable gene content of the YAC. A287-C10 contains two VH1 genes that approximate the predicted sizes (Shin et al., supra; Matsuda et al., 1993, supra); restriction analysis with the three enzymes gave close to the expected fragment sies; e.g. with EcoRI observed bands are 3.4 and 7.8 kb (expected are 3.4 and 7.2 kb). The predicted size EcoRI fragments for VH4 (5.3 kb observed, 5.1 kb expected) and for VH6 (0.8 kb observed, 0.9 kb expected) (Shin et al., supra; Matsuda et al., supra) were present in A287-C10. The expected size EcoRI fragment was seen for VH2 (5.5 kb observed, 5.4 kb expected), but the BamHI and HindIII fragments were different from those predicted. Coincident hybridization of the BamHI and HindIII fragments with a pBR322 probe suggested that the EcoRI site which is at the 5' end of the VH2 gene (Shin et al., supra) is the 5' cloning site, thus eliminating the natural 5' HindIII site and BamHI sites. The overall size of the YAC insert (estimated to be approximately 220 kb) fits well with the predicted size for an intact, unrearranged segment starting at the 5' end of the 3'-most VH2 gene and extending to an EcoRI site 3' of the delta locus (Shin et al., supra).

3. Identification and characterization of IgK YACs containing CK and VK sequences:

Two YACs were identified in a screen of pulsed-field gel (PFG) pools from the Washington University (St. Louis, Mo.) human YAC library with a probe from the human kappa constant region (CK) gene (2.5 kb EcoRI fragment ATCC No. 59173, Parklawn Dr., Rockville, Md.). The YACS, designated A80-C7 (170 kb) and A276-F2 (320 kb), contain the kappa deleting element kde, CK, JK and the C-J intronic enhancer and extend 3' beyond kde. Extending 5' from JK, the YACs also contain the B1, B2 and B3 VK genes determined by hybridization and/or PCR, and possibly other VK sequences. The A80-C7/AB1380 strain housed, in addition to the IgK YAC, an unrelated YAC of similar size. Therefore, meiotic segregation was used to separate these YACs; A80-C7 was crossed to YPH8S57 and a meiotic product was obtained which contained only the IgK YAC (MP8–2; host genotype=α ade2 leu2 his3 his5 lys2 ura3 trp1 can1 cyh2). The A80-C7 and A276-F2 YACs have been targeted with pLUTO to incorporate the human HPRT minigene into the YAC right vector arm.

Restriction analysis of the IgK YACs A80-C7 and A276-F2 using a number of enzymes supports the conclusion that both YACs are unrearranged (i.e., in germline configuration). For example, BamHI digestion followed by hybridization with the CX probe demonstrates the expected 13 kb restriction fragment (Klobeck et al., *Biol. Chem. Hoppe-Seyler* 370:1007–1012 (1989)). The same-sized band hybridizes to a JK probe (a 1.2 kb PCR product using primer set to amplify the JK1-5 region), as predicted from the genomic map (Klobeck et al., supra). The B3 class IV gene (probe is a 123 bp PCR product from the B3 gene) gives a 4.9 kb BamHI and a 2.2 kb BglII fragment, close to the published values of 4.6 kb and 2.3 kb, respectively (Lorenz et al., *Molec. Immunol.* 25:479–484 (1988)). PCR analysis of both IgK YACs as well as human genomic DNA for the following kappa locus sequences revealed the predicted band sizes: Kde (120 bp), CK (304 bp), C-J 5 intronic enhancer (455 bp), JK1-5 (1204 bp), B3 VK (123 bp) and B1 VK pseudogene (214 bp). Sequences used to design PCR primers for the CK, JK and C-J enhancer regions are from Whitehurst et al., *Nucl. Acids. Res.* 20:4929–4930 (1992); Kde is from Klobeck and Zachau, *Nucl. Acids. Res.* 14:4591–4603 (1986); B3 is from Klobeck et al., *Nucl. Acids. Res.* 13:6515–6529 (1985); and Bi is from Lorenz et al., supra.

B. Introduction of 680 kb yHPRT YAC into ES Cells

1. Culture of yHPRT yeast strain and preparation of yeast spheroplasts

The 680 kb yHPRT is a YAC containing a functional copy of the human hypoxanthine phosphoribosyltransferase (HPRT) gene cloned from a YAC library, as described in Huxley, et al. (1991) *Genomics* 9:742–750. The yeast strain containing the yHPRT was grown in uracil and tryptophan deficient liquid media, as described in Huxley, et al. (1991) supra.

To prepare the yeast spheroplasts, a 400 ml culture of yeast containing yHPRT was spun down and the yeast pellet was washed once with water and once with 1 M sorbitol. The yeast pellet was resuspended in SPEM (1 M sorbitol, 10 mM sodium phosphate pH 7.5, 10 nM EDTA pH 8.0, 30 mM β-mercaptoethanol) at a concentration of $5 \times 10^8$ yeast cells/ml. Zymolase 20T was added at a concentration of 150 μg/ml of yeast cells, and the culture was incubated at 30° C. until 90% of the cells were spheroplasts (usually for 15–20 minutes). The cells were washed twice in STC (1 M sorbitol, 10 mM Tris pH 7.5, 10 mM $CaCl_2$) and resuspended in STC at a concentration of $2.5 \times 10^8$/ml.

2. Culture of E14TG2a ES Cells

HPRT-negative ES cell line E14TG2a was cultured as previously described.

3. Fusion of ES Cells and Yeast Spheroplasts

Exponentially growing E14TG2a ES cells growing on gelatin-coated dishes were trypsinized and washed three times with serum-free DMEM. A pellet of $2.5 \times 10^8$ yeast spheroplasts was carefully overlaid with $5 \times 10^6$ ES cells which were spun down onto the yeast pellet. The combined pellet was resuspended in 0.5 ml of either 50% polyethylene glycol (PEG) 1500 or 50% PEG 4000 (Boeringer Mannheim) containing 10 mM CaCl2. After 1.5 minutes incubation at room temperature or at 37° C., 5 ml of serum-free DMEM were added slowly, and the cells were left at room temperature for 30 minutes. The cells were then pelleted and resuspended in 10 ml of ES cell complete medium (as previously described) and were plated onto one 100 mm plate coated with feeder cells. After 24 hours the medium was replaced with fresh medium. Forty-eight hours post-fusion, HAT (ES media containing $1 \times 10^{-4}$ M hypoxanthine, $4 \times 10^{-7}$ M aminopterin, $1.6 \times 10^{-5}$ thymidine) selection was imposed. HAT-resistant ES colonies were observed 7–10 days post-fusion in the plates from both the different fusion conditions used. yHPRT-ES ("ESY") fusion colonies were picked and plated onto feeder-coated wells, and expanded for further analysis.

4. Analysis of YAC DNA Integrated into yHPRT-ES Fusion Clones

DNA extracted form 23 yHPRT-ES fusion colonies was digested with HindIII and subjected to Southern blot analysis (FIG. 12) using the probes: a human repetitive Alu sequence (A); pBR322-specific sequences for the right (B) and left (C) YAC vector arms; yeast Ty repetitive sequence (D); yeast single copy gene LYS2 (E). The human HPRT probe, a 1.6 kb full length cDNA (Jolly et al., *Proc. Natl. Acad. Sci. USA* 80:477–481 (1983)) was used to confirm the presence of the human HPRT gene in ESY clones. The Alu probe was a 300 bp BamHI fragment from the BLUR8 Alu element in pBP63A (Pavan et al., *Proc. Natl. Acad. Sci. USA* 78:1300–1304 (1990)). The right and left vector arm probes were pBR322-derived BamHI-PvuII 1.7 and 2.7 kb fragments, respectively, which correspond to the vector sequences in pYAC4 (scheme a, b (Burke et al., in: Guide to Yeast Genetics and Molecular Biology, Methods in Enzymology, Guthrie and Fink, eds., Academic Press, 194:251–270 (1991)). The 4.5 kb fragment, detected by the right arm probe, spans the region between the HindIII site at the telomere 5' end and the first HindIII site within the human insert (scheme a). The 3 kb and 4.1 kb fragments detected by the left end probe correspond to the region between the HindIII site at the telomere end and the HindIII site 5' of the yeast sequences, and the region spanning from the HindIII site 3' of the centromere into the human insert, respectively (scheme b). The difference in the hybridization intensity of these two bands relates to the difference in the amount of homology between these fragments and the probe. The yeast Ty repetitive probe (Philippsen et al., in Gene Expression in Yeast, Proceedings of the Alko Yeast Symposium, Helsinki, Korhola and Vaisanen, eds., Foundation for Biotechnical and Industrial Fermentation Research, 1:189–200 (1983)) was a 5.6 kb XhoI fragment isolated from Ty1-containing pJEF742 which could also detect the 3' HindIII fragment of Ty2, due to the homology between the two elements. The LYS2 gene probe was a 1.7 BamHI fragment from pLUS (Hermanson et al., *Nuc. Acids. Res.* 19:4943–4948 (1991)).

Figure 12A:
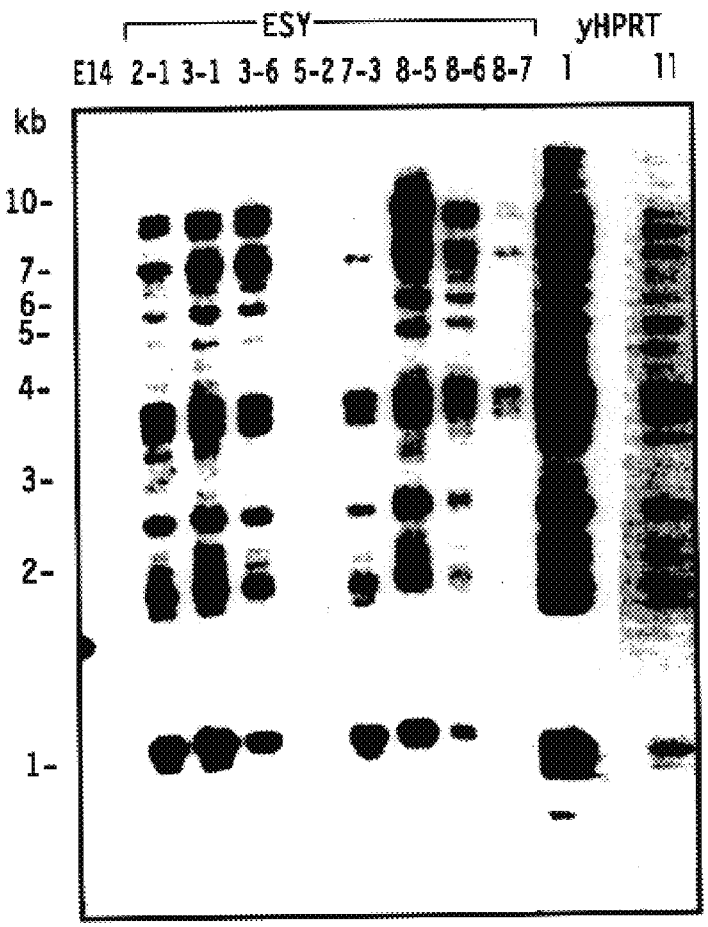
FIGS. 12 A–E are photographs of the results of Southern blot analysis to characterize yHPRT and yeast genomic DNA integrated in ES clones as described in Example VI, infra (A=human repetitive Alu sequence; B,C=pBR322-specific sequences for the right (B) and left (C) YAC arms; D=yeast Ty repetitive sequence; E=yeast single copy gene LYS2. Shorter exposure times (12 hrs for II as compared to 48 hrs for I) of yHPRT probed with Alu and Ty sequences also are also shown. Positions of molecular weight markers are indicated. Schemes of right (a) and left (b) vector arms and the locations of pBR322-derived YAC vector fragments are shown (=telomere; =yeast-derived sequences; 0=yeast centromere; =pBR322-derived sequences; =human insert; =EcoRI cloning site; H=HindIII sites).
Figure 12B:
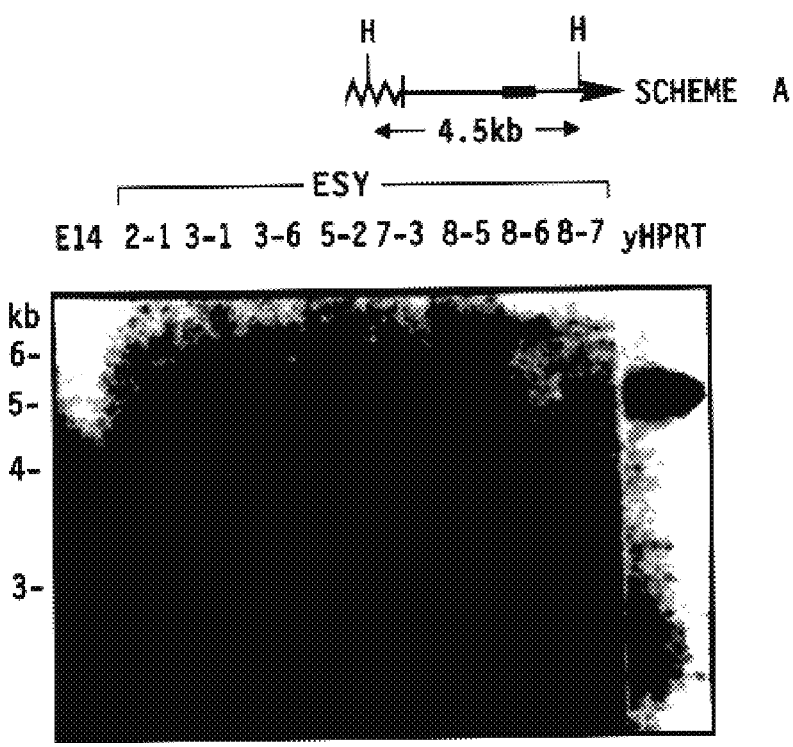
Figure 12C:
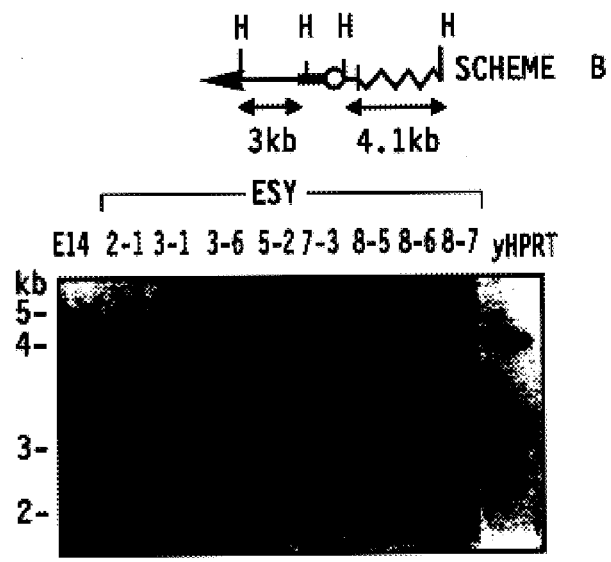
Figure 12D:
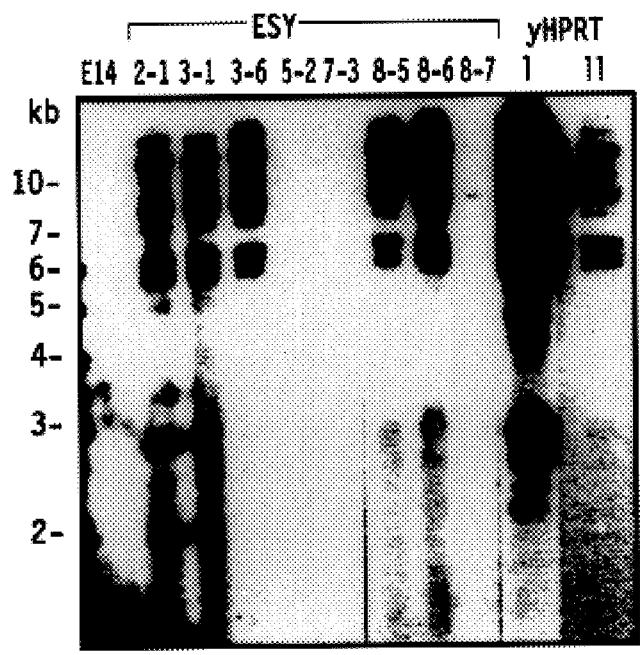
Figure 12E:
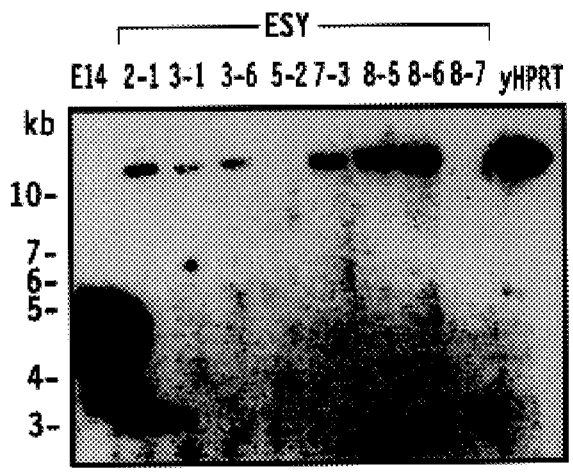

Hybridization with a human HPRT probe (full length 1.6 kb cDNA probe) demonstrated that all the clones analyzed contained the same 15, 7 and 5 kb exon-containing fragments of the human HPRT gene as the yHPRT YAC. Reprobing the same blots with a human repetitive Alu sequence 300 bp probe indicated that all the clones analyzed contained most, if not all, the Alu-containing fragments present in yHPRT (FIG. 12A). These data indicate that in most of the clones analyzed the 680 kb human insert had not been detectably rearranged or deleted upon integration into the ES cell genome. Integration of YAC vector sequences was examined using probes specific for the vector arms. Rehybridization of the same blots with a probe for the right YAC vector arm, detecting a 4.5 kb HindIII fragment, indicated that in 10 out of 23 of the clones analyzed, the right YAC arm up to the telomere was still intact and unrearranged and linked to the human insert (FIG. 12B) thus providing further evidence for the integrity of the YAC in these clones. The left arm probe detected the 3 kb and 4.1 kb HindIII yHPRT fragments in 18 out of the 20 clones analyzed (FIG. 12C), indicating a high frequency of left arm retention.

Figure 13A:
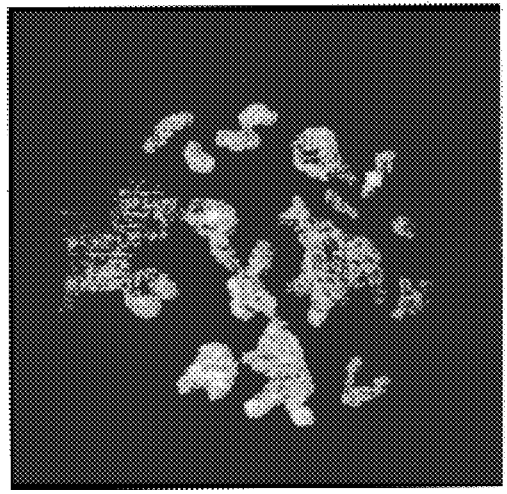
FIGS. 13 A–D are photomicrographs of the results of in situ hybridization to detect integration of yHPRT and yeast genomic sequences in ES cell chromosomes as described in Example VI, infra (A, B=metaphase spreads from ESY 8-7 cells hybridized to biotinylated human genomic sequences and C=metaphase spreads or D=interphase nuclei from ESY 8-6 cells hybridized to biotinylated yeast repeated DNA sequences).
Figure 13B:
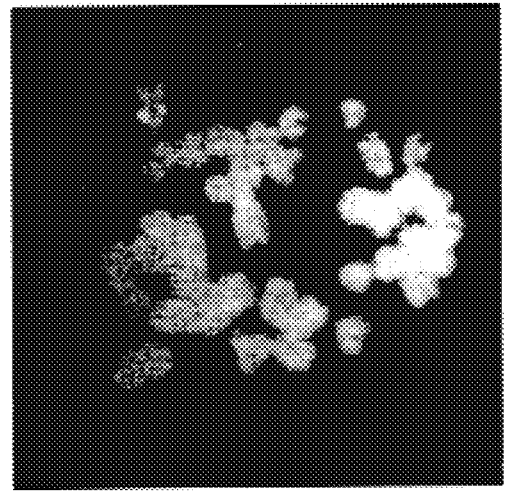
Figure 13C:
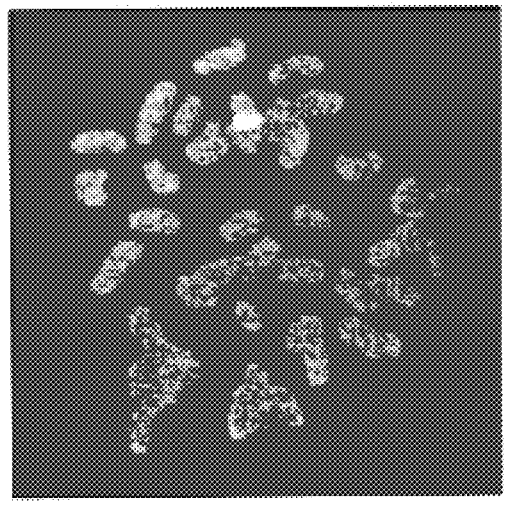
Figure 13D:
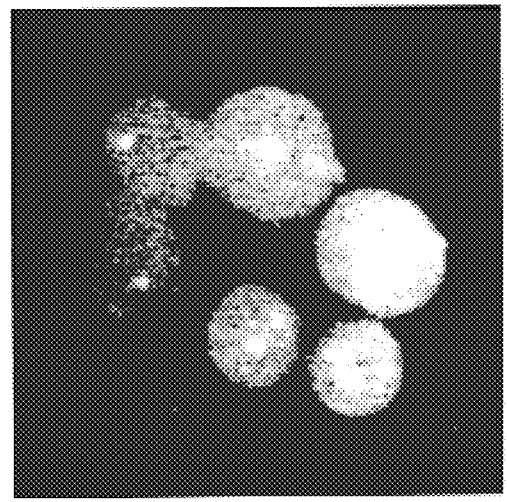
Figure 14A:
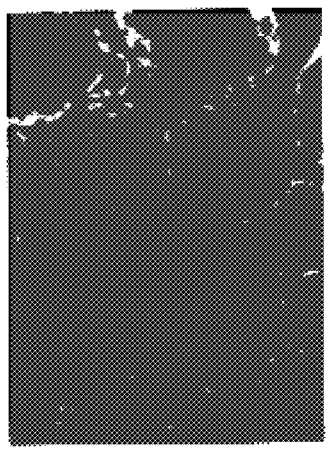
FIGS. 14 A, B, C demonstrates the stable retention of yHPRT during in vitro ES cell differentiation and transmission through the mouse germline, as described in Example VI, infra (A: a, b=embryoid bodies; and differentiated cell types:c=blood islands; d=contracting muscle; e=neuronal cells; f=neural tubules formed by ESY clones; B: Southern blot analysis of DNA extracted from differentiated ESY 5-2, 3-6, 8-5 and 8-6 (20 μg) and yHPRT in AB1380 (40 ng) using a=human Alu probe; b=yeast Ty sequences; C: Southern blot analysis of tail DNA (20 μg) from 2 agouti offspring (4-2 and 4-3) derived from ESY chimeric male 394/95-2 using a=human Alu and b=Ty sequences; shorter exposures (12 hr) of 8-6 and yHPRT probed with Ty are shown (II).
Figure 14B:
Figure 14C:
Figure 14D:
Figure 14E:
Figure 14F:
Figure 14G:
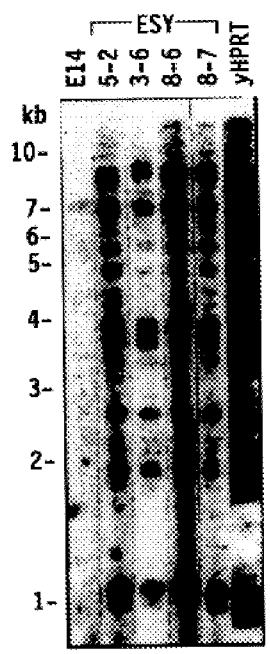
Figure 14H:
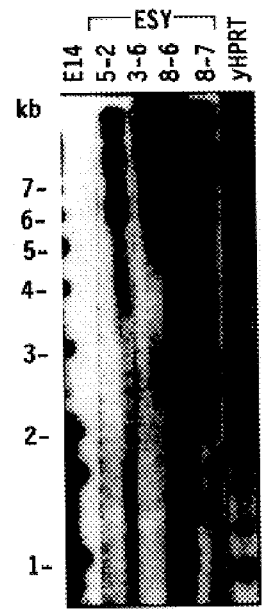
Figure 14I:
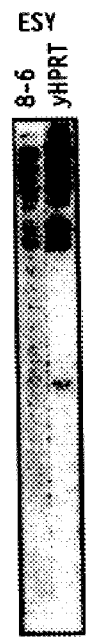
Figure 14J:
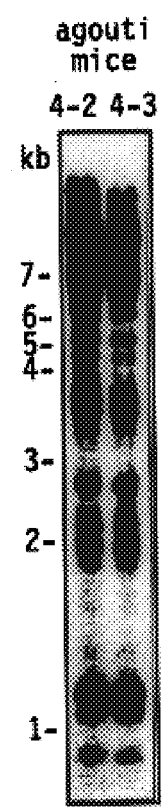
Figure 14K:
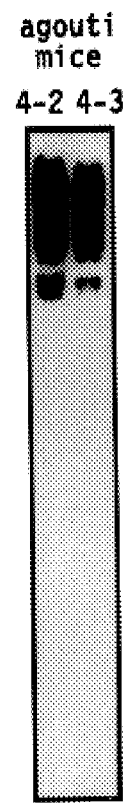

The structural integrity of yHPRT in ESY clones was further evaluated for two clones (ESY 5-2 and 8-7) using pulsed-field gel restriction analysis. In yeast carrying yHPRT, five Sfi fragments of the following approximate sizes were defined by different probes: 315 kb (Alu, left arm), 145 kb (Alu, HPRT); 95 kb (Alu, right arm), 70 and 50 kb (Alu only). In both ES clones, the internal HPRT and Alu-specific fragments were similar in size to the yHPRT fragments. The end fragments detected for both clones were larger than those in yHPRT, as expected for YACs integrated within a mouse chromosome: 185 and 200 kb for the right end fragment, respectively, and over 800 kb for the left end fragment for both clones. These data, together with the Alu profile, provide additional evidence for the retention of the structural integrity of the YAC in these clones. These studies were complemented by fluorescence in-situ hybridization carried out on ESY 8-7 (FIGS. 13 A, B) and ESY 8-6 metaphase chromosome spreads in which a single integration site was detected for the human sequences. Photomicrographs of representative metaphase spreads (FIGS. 13 A, B, C) or interphase nuclei (FIG. 13D) from ESY 8-7 cells (FIGS. 13 A, B) hybridized with biotinylated human genomic sequences and ESY 8-6 cells (FIGS. 13 C, D) hybridized with biotinylated yeast repeated DNA sequences. The human probe was generated from human genomic placental DNA (Clontech, Palo Alto, Calif.). The yeast probe consisted of a mix of DNA fragments encoding the yeast repeated elements; delta (a 1.08 kb Sau3A fragment of pdelta6 (Gafner et al., *EMBO J.* 2:583–591 (1983)) and Ty (a 1.35 kb EcoRI-SaII fragment of p29 (Hermanson et al., *Nuc. Acids. Res.* 19:4943–4948 (1991)), the rDNAs (a 4.6 kb BgIIIk-A L90 and a 4.4 kb BgIII-B L92 fragment (Keil and Roeder, *Cell* 39:377–386 (1984)), and the Y' telomere elements (2.0 and 1.5 kb BgIII-HindIII fragments of p198 (Chan and Tye, *Cell* 33:563–573 (1983)). Hybridization of sequences on chromosome metaphase spreads with biotinylated probes and detection by Avidin-FITC followed by biotin-anti-Avidin and Avidin-FITC amplification was carried as described by Trask and Pinkel, *Methods Cell Biol.* 30:383–400 (1990), using a Zeiss Axiophot microscope. Chromosomes were counterstained with propidium iodide. The photomicrographs shown are representative of 95% of the metaphase spreads or interphase nuclei scanned in three independent experiments carried out with the human or the yeast probes. A single integration site was detected for the human sequences.

The same blots were also probed with the yeast Ty repetitive element sequence to detect the presence of yeast genomic DNA sequences in the ESY clones (FIG. 12 D). Whereas some of the clones were found to contain most of the Ty-containing fragments present in the parental yeast strain, some of the clones were found to have a very small fraction, if at all, of the Ty-containing fragments. These results indicate that in some ES clones, although the YAC DNA is integrated intact, little or no yeast genomic DNA was integrated. To determine if the yeast chromosomal DNA was integrated at single or multiple sites within the ES cell genome, fluorescent in-situ hybridization was performed on ESY clone 8-6 which had a complete Ty profile. A single integration site was detected using a combined yeast repetitive probe (FIGS. 13 C, D), indicating that within the limits of resolution, all yeast DNA fragments integrated in one block.

Using the ability of ES cells to undergo in vitro orderly differentiation, YAC stability and the effect of integrated DNA on the pluripotency of ES cells was investigated. Four ES clones, containing different amounts of yeast DNA (ESY 5-2, 3-6, 8-6 and 8-7) exhibited a differentiation pattern indistinguishable from that of unfused ES cells: formation of embryoid bodies giving rise to a variety of differentiated cell types (FIG. 14 A). Southern blot analysis was performed on DNA extracted from differentiated ESY 5-2, 3-6, 8-5 and 8-6 (20 µg) and yHPRT in AB1380 (40 ng) using (a) a human Alu probe; (b) yeast Ty sequences. ES clones were induced to form embryoid bodies by culturing them as aggregates in suspension for 10–14 days as described by Martin and Evans, *Cell* 6:467–474 (1975). Following their reattachment to tissue culture substratum, ESY-derived embryoid bodies gave rise to differentiated cell types. YAC and yeast DNA sequences were stably retained by the differentiated ES clones during 40 days of culture in non-selective medium, demonstrating that the stably integrated foreign DNA did not impair the pluripotency of the ES cells (FIG. 14 B). The differentiated cultures maintained a functional human HPRT gene as evidenced by their normal growth and differentiation when transferred to HAT-selective medium.

5. Generation of chimeric mice from VHPRT-ES cell lines

The ability of ESY cells to repopulate mice, including the germline, was demonstrated by microinjection of ES cells into mouse blastocysts and the generation of chimeric mice. ESY cells were microinjected into C57BL/6J mouse blastocysts, and chimeric mice were generated as previously described. Chimeric males were mated with C57BL/6J females and germline transmission was determined by the presence of agouti offspring. Genomic DNA prepared from the tails of the chimeric mice were analyzed for the presence of the yHPRT DNA in the mouse genome by PCR analysis. The presence of the YAC left arm was analyzed using the two priming oligonucleotides, 5' TTCTCGGAGCACTGTC CGACC (SEQ ID NO: 24) and 5 ' CTTGCGCCTTAAAC-CAACTTGGTACCG (SEQ ID NO: 25), which were derived, respectively, from the pBR322 sequences and the SUP4 gene within the YAC left vector arm. A 259 bp PCR product was obtained from the analysis of the yeast containing yHPRT and the ESY cell lines. PCR analysis of tail DNA prepared from 18 chimeric mice generated from ESY cell lines ESY3-1 ESY3-6 and ESY5-2, gave rise to the expected PCR product, thus indicating the presence of the YAC left vector arm in the genome of the chimeric mice.

6. Germline transmission of VHPRT

Chimeric males, with coat color chimerism of 30–60%, derived from the ESY cell lines ESY3-1 and ESY5-2 were set up for mating for germline transmission evaluation, i.e. to determine whether the genetic modification was passed via the germ cells (sperm or oocytes) to the progeny of the animals. Three of the chimeric ESY3-1 derived males, 394/95-1, 394/95-2 and 411-1 transmitted the ES cell genome to their offspring at a frequency of 20%, 30% and 30%, respectively. Southern blot analysis of tail DNA from the agouti pups indicated the presence of the yHPRT in the genome of three mice, 4-2, 4-3 and 5-1, derived from the 394/395-2 chimera. The Alu profile obtained from such analysis was indistinguishable from that of the parent ES3-1 cell line (FIG. 14 C), demonstrating that the 680 kb human insert was transmitted faithfully through the mouse germline.

Using a human HPRT-specific PCR assay on mRNA-derived cDNAs from a yHPRT-containing offspring, the expression of the human HPRT gene in all the tissues tested was detected (FIGS. 15 A and B), thus demonstrating the transmitted YAC retained its function with fidelity. In this experiment, human HPRT mRNA was detected by reverse transcription (RT)-PCR in ES, ESY 3-1 and Hut 78 (human) cells, spleen and liver from a control mouse (C) or the 4-3 agouti offspring (derived from the 394/95-2 chimera) and a sample containing no template DNA (indicated as "-" in FIG. 15A). Reverse transcription of poly (A+) RNA and PCR amplification of specific cDNA sequences were performed using the cDNA Cycle Kit (Invitrogen). Specific amplification of a 626 bp fragment from human HPRT cDNA in the presence of murine HPRT cDNA was performed as outlined by Huxley et al, supra. Integrity of all RNA samples was demonstrated by PCR amplification of cDNAs for the mouse γ-interferon receptor. The primers used to amplify a 359 bp fragment were: GTATGTGGAG-CATAACCGGAG (SEQ ID NO: 26) and CAG-GTTTTGTCTCTAACGTGG (SEQ ID NO: 27). The human HPRT and the γ-interferon receptor primers were designed to eliminate the possibility of obtaining PCR products from genomic DNA contamination. PCR products were analyzed by electrophoresis and visualized with ethidium bromide. The size markers are 1 kb ladder (BRL). The results of detection of mouse γ-interferon receptor mRNA by RT-PCR in the samples described above are shown in FIG. 15B. The specific human HPRT mRNA was also detected in the other tissues tested (brain, kidney and heart) derived from the 4-3 mouse. Comparable steady-state levels of mouse and human HPRT mRNA were detected in the liver of yHPRT-containing progeny. These results indicate that the uptake of as much as 13 megabases of yeast genomic DNA was not detrimental to proper development, germline transmission or gene expression.

The above results demonstrate that yeast spheroplasts are an effective vehicle for the delivery of a single copy large molecular weight DNA fragment into ES cells and that such molecules are stably and functionally transmitted through the mouse germline. The Alu profiles, complemented by PFGE analysis and in situ hybridization for some of the ES clones, strongly argue that the majority of the clones contained virtually all the human insert in unrearranged form (i.e. in "germline configuration"), with a high frequency of clones (40%) also retaining both YAC arms. The significant uptake of yeast genomic DNA was not detrimental to proper differentiation of ES cells in vitro and in vivo and did not prevent germline transmission or gene expression. Using these methods, one can transmit large fragments of genomic DNA as inserts into non-human animal genomes, where the inserts may be transmitted intact by germline transmission. Therefore, a wide variety of xenogeneic DNA can be introduced into non-human hosts such as mammals, particularly small laboratory animals, that may impart novel phenotypes or novel genotypes. For example, one can provide in small laboratory animals genes of a mammal, such as a human, to study the etiology of a disease, the response to human genes to a wide variety of agents. Alternatively, one can introduce large loci into a mammalian host to produce products of other species, for example humans, to provide human protein sequences of proteins such as immunoglobulins, T-cell receptors, major histocompatibility complex antigens, etc.

Introduction of heavy chain YAC A287-C10 and kappa chain YAC A80-C into ES cells and Embryos Yeast containing the human heavy chain YAC A287-C10 targeted with PLUTO (yA287-C10) were spheroplasted and fused with the HPRT-deficient ES cell line E14.1TG3B1 as described above. Ten HAT-resistant ES (ESY) clones (2B, 2C, 2D, 3A, 3B, 5C, 1125A, 1125E, 100/1500 and 100/4000) were picked and were expanded for DNA analysis. Evaluation of the integrated YAC was performed by Southern blot analysis of HindIII-digested DNA from these clones, using human heavy chain probes for the D, $J_H$, $\mu$, and VH2 regions, decribed above. All ESY clones were found to contain the expected >10 kb $J_H$ and $\mu$ fragments. All ESY clones except 2D and 5C clones, were found to contain the 4.8 kb VH2 kb fragment. All ESY clones, except 2D and 3B were found to contain the expected 10 and 7.6 kb D gene fragments. Yeast genomic sequences were detected by hybridization to the yeast repetitive Ty element in all ESY clones except 2B, 2D, 100/1500 and 5C. ESY clones 2B, 3A and 5C were microinjected into C57B/6 blastocysts as described above and chimeric mice (10 from 2B clone, 1 from 3A clone and 1 from 5C clone) were generated. Southern blot analysis of tail DNA from 10 of these chimeric animals, indicated the presence of most, if not all, of the apparent 10 Alu fragments, detected in yA287-C10 in yeast, as well as the presence of VH2 and D gene fragments. The generated chimeric mice were bred with C57BL16J mice for germline transmission evaluation. A chimeric male 78K-3 derived from the 2B clone transmitted the ES cell genome to its offspring at a frequency of 100%. Southern blot analysis of tail DNA from 4 out of 6 agouti mice pups indicated the presence of human heavy chain sequences.

Fusion experiments with yeast containing the human kappa chain YAC A80-C7 targeted with pLUTO (yA80-C7) with E14.1TG3B1 ES cells generated 2 HAT-resistant ESY clones: M4.4.1 and M5.2.1. Southern blot analysis of HindIII-digested DNAs from these clones revealed the presence of all the apparent 10 Alu fragments detected in yA80-C7 in yeast. In both clones yeast genomic sequences were integrated. ESY clones were microinjected into C57B1/6J blastocysts and chimeric mice were generated.

EXAMPLE VII

Production of human Ia by chimeric mice by Introduction of Human Ig using Homologous Recombination As an alternative approach to that set forth in Examples I–VI, human Ig genes are introduced into the mouse Ig locus by replacing mouse heavy and light chain immunoglobulin loci directly with fragments of the human heavy and light chain loci using homologous recombination. This is followed by the generation of chimeric transgenic animals in which the embryonic stem-cell derived cells contribute to the germ line.

A. Construction of human heavy chain replacement vector.

Figure 16A:
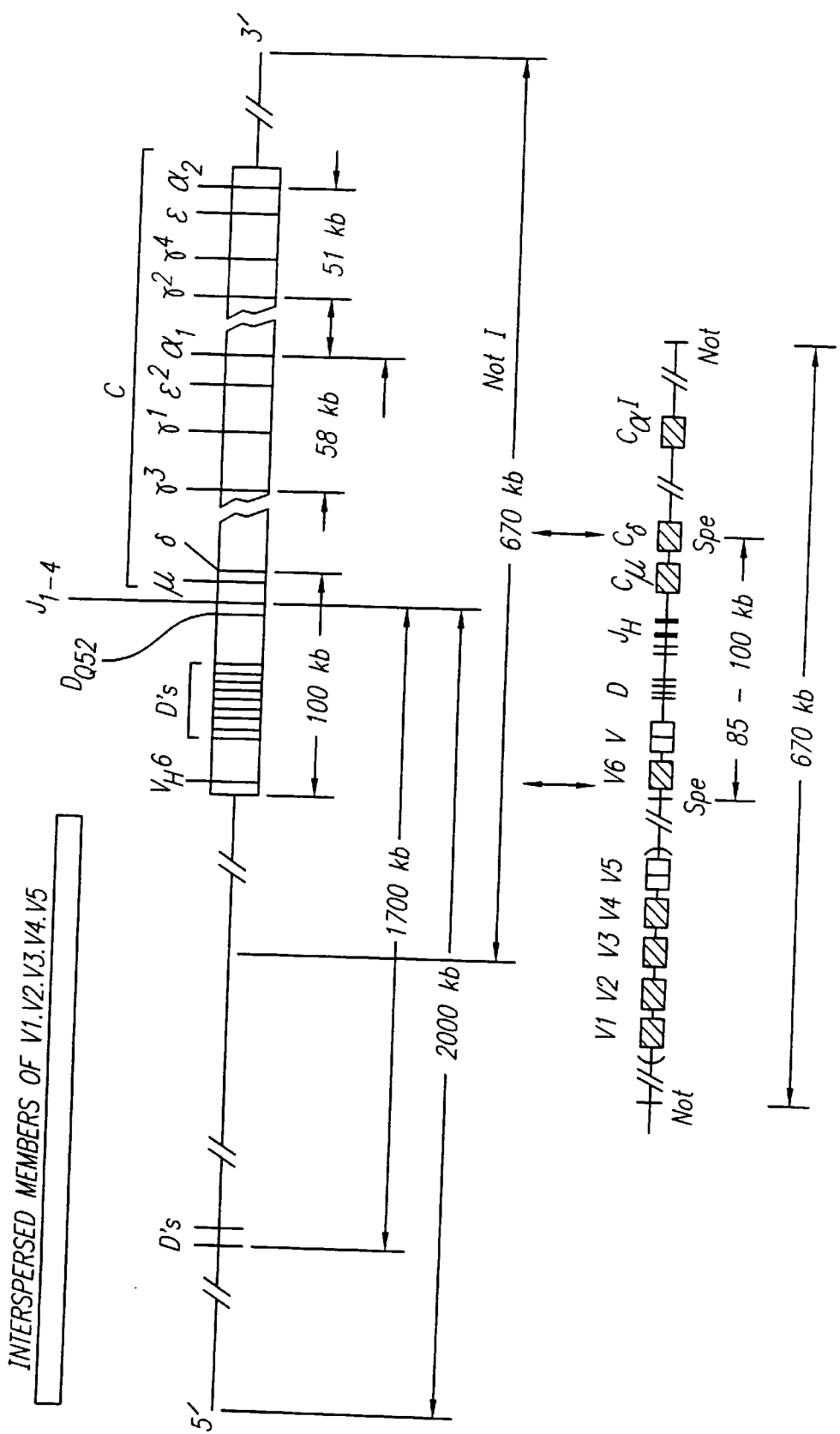
FIGS. 16 A–C is a diagram of the human immunoglobulin heavy chain locus, and a human heavy chain replacement YAC vector, as described in Example VII, infra.
Figure 16B:
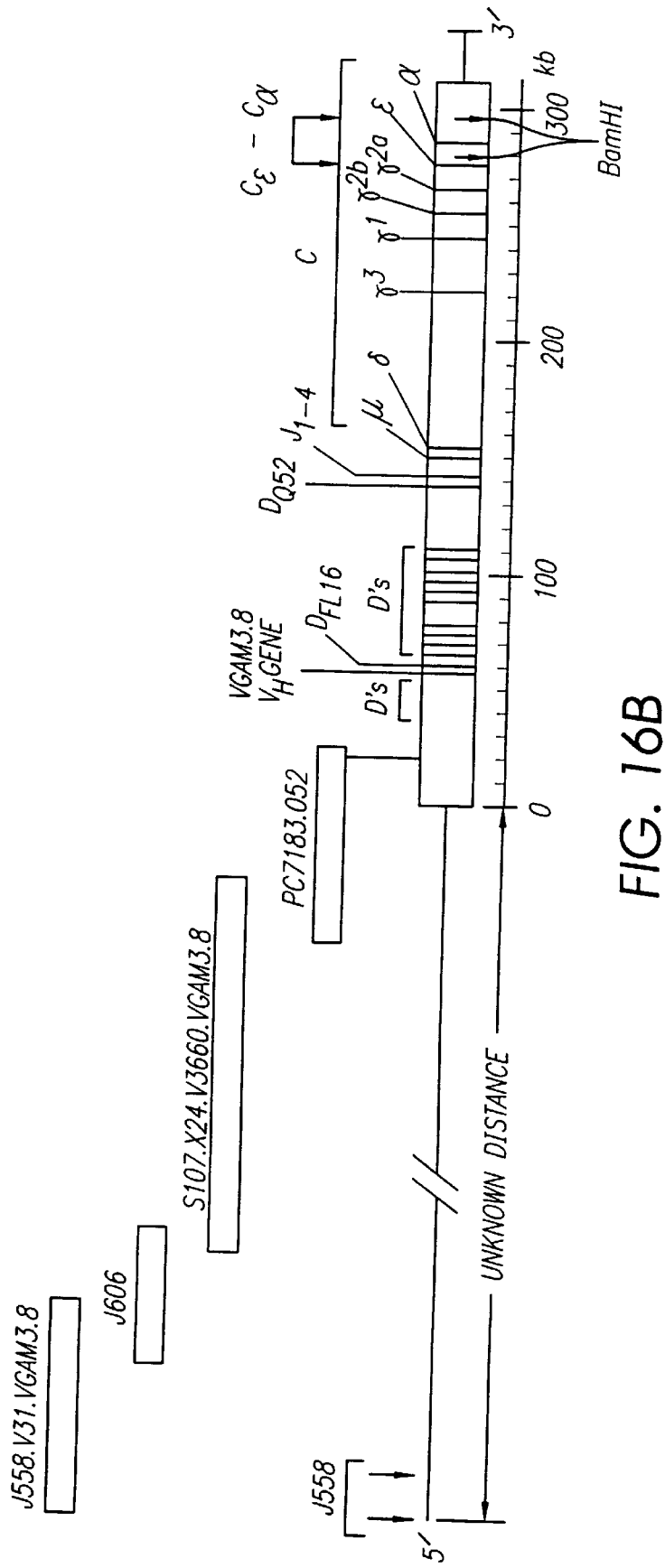
Figure 16C:
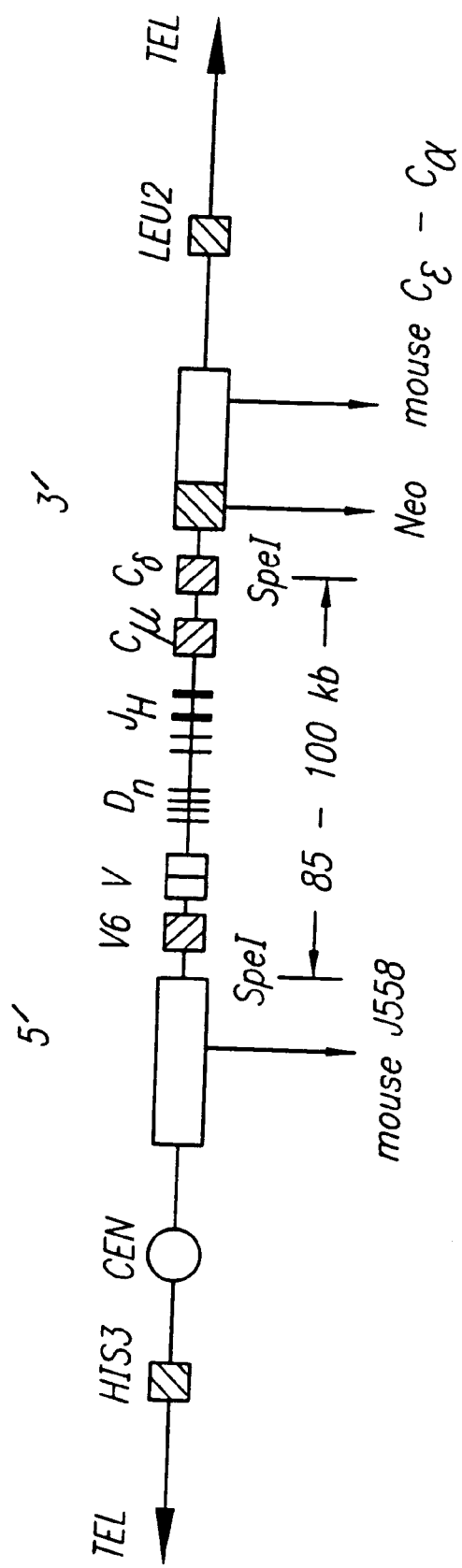

The replacing human sequences include the SpeI 100 kb fragment of genomic DNA which encompasses the human VH6-D-J-C$\mu$-C$\delta$ heavy chain region isolated from a human-YAC library as described before. The flanking mouse heavy chain sequences, which drive the homologous recombination replacement event, contain a 10 kb BamHI fragment of the mouse C$\epsilon$-C$\alpha$ heavy chain and a 5' J558 fragment comprising the 5' half of the J558 fragment of the mouse heavy chain variable region, at the 3' and 5' ends of the human sequences, respectively (FIG. 16). These mouse sequences are isolated from a mouse embryo genomic library using the probes described in Tucker et al. (1981), *PNAS USA,* 78: 7684–7688 and Blankenstein and Krawinkel (1987, supra), respectively. The 1150 bp XhoI to BamHI fragment, containing a neomycin-resistance gene driven by the Herpes simplex virus thymidine kinase gene (HSV-tk) promoter and a polyoma enhancer is isolated from pMC1Neo (Koller and Smithies, 1989, supra). A synthetic adaptor is added onto this fragment to convert the XhoI end into a BamHI end and the resulting fragment is joined to the BamHI mouse C$\epsilon$-C$\alpha$ in a plasmid.

From the YAC clone containing the human heavy chain locus, DNA sequences from each end of the insert are recovered either by inverse PCR (Silverman et al. (1989), *PNAS,* 86:7485–7489), or by plasmid rescue in *E. coli,* (Burke et al., (1987); Garza et al. (1989) *Science,* 246:641–646; Traver et al., 1989) (see FIG. 8). The isolated human sequence from the 5'V6 end of the YAC is ligated to the mouse J558 sequence in a plasmid and likewise, the human sequence derived from the 3' Cd end of the YAC is ligated to the Neo gene in the plasmid containing Neo and mouse C$\epsilon$-C$\alpha$ described above. The human V6-mouse J558 segment is now subcloned into a half-YAC cloning vector that includes a yeast selectable marker (HIS3) not present in the original IgH YAC, a centromere (CEN) and a single telomere (TEL). The human C$\delta$-Neo-mouse C$\epsilon$-C$\alpha$ is likewise subcloned into a separate half-YAC vector with a different yeast selectable marker (LEU2) and a single TEL. The half-YAC vector containing the human V6 DNA is linearized and used to transform a yeast strain that is deleted for the chromosomal HIS3 and LEU2 loci and which carries the IgH YAC. Selection for histidine-prototrophy gives rise to yeast colonies that have undergone homologous recombination between the human V6 DNA sequences and contain a recombinant YAC. The half-YAC vector containing the human Cδ DNA is then linearized and used to transform the yeast strain generated in the previous step. Selection for leucine-prototrophy results in a yeast strain containing the complete IgH replacement YAC (see FIG. 16). Preferably, both targeting events are performed in a single transformation step, selecting simultaneously for leucine and histidine prototrophy. This is particularly useful when the original centric and acentric YAC arms are in opposite orientation to that shown in FIG. 16. This YAC is isolated and introduced into ES cells by microinjection as described previously for embryos.

EXAMPLE VIII

Crossbreeding of transgenic mice

A. Generation of human monoclonal antibody producing mice

Mice containing the human immunoglobulin locus are mated to mice with inactivated murine immunoglobulin genes to generate mice that produce only human antibodies. Starting with four heterozygous strains, three generations of breeding are required to create a mouse that is homozygous for inactive murine kappa and heavy chain immunoglobulins, and heterozygous for human heavy and kappa chain immunoglobulin loci. The breeding scheme is shown in FIG. 17.

EXAMPLE IX

Production of Human Monoclonal Antibodies

A. Immunization of mice

Germline chimeric mice containing integrated human DNA from the immunoglobulin loci are immunized by injection of an antigen in adjuvant. The mice are boosted with antigen 14 days after the primary immunization, repeated after 35 and 56 days. A bleed is done on the immunized animals to test the titer of serum antibodies against the immunizing antigen. The mouse with the highest titer is sacrificed, and the spleen removed.

B. Fusion of splenocytes

Myeloma cells used as the fusion partner for the spleen cells are thawed 6 days prior to the fusion, and grown in tissue culture. One day before the fusion, the cells are split into fresh medium containing 10% fetal calf serum at a concentration of $5 \times 10^5$ cells/ml. On the morning of the fusion the cells are diluted with an equal volume of medium supplemented with 20% fetal calf serum and 2× OPI (3 mg/ml oxaloacetate, 0.1 mg/ml sodium pyruvate and 0.4 IU/ml insulin) solution.

After sacrificing the mouse, the spleen is aseptically removed, and placed in a dish with culture medium. The cells are teased apart until the spleen is torn into fine pieces and most cells have been removed. The cells are washed in fresh sterile medium, and the clumps allowed to settle out.

The splenocytes are further washed twice by centrifugation in medium without serum. During the second 5 wash, the myeloma cells are also washed in a separate tube. After the final wash the two cell pellets are combined, and centrifuged once together.

A solution of 50% polyethylene glycol (PEG) is slowly added to the cell pellet while the cells are resuspended, for a total of two minutes. 10 ml of prewarmed medium is added to the cell solution, stirring slowly for 3 minutes. The cells are centrifuged and the supernatant removed. The cells are resuspended in 10 ml of medium supplemented with 20% fetal calf serum, 1× OPI solution and 1× AH solution (58 μM azaserine, 0.1 mM hypoxanthine). The fused cells are aliquoted into 96-well plates, and cultured at 37° for one week.

Supernatant is aseptically taken from each well, and put into pools. These pools are tested for reactivity against the immunizing antigen. Positive pools are further tested for individual wells. When a positive well has been identified, the cells are transferred from the 96-well plate to 0.5 ml of medium supplemented with 20% fetal calf serum, 1× OPI, and 1× AH in a 24-well plate. When that culture becomes dense, the cells are expanded into 5 ml, and then into 10 ml. At this stage the cells are sub-cloned so that a single antibody producing cell is in the culture.

In accordance with the above procedures, a chimeric non-human host, particularly a murine host, may be produced which can be immunized to produce human antibodies or analogs specific for an immunogen. In this manner, the problems associated with obtaining human monoclonal antibodies are avoided, because the transgenic host can be immunized with immunogens which could not be used with a human host. Furthermore, one can provide for booster injections and adjuvants which would not be permitted with a human host. The resulting B-cells may then be used for immortalization for the continuous production of the desired antibody. The immortalized cells may be used for isolation of the genes encoding the immunoglobulin or analog and be subjected to further molecular modification by methods such as in-vitro mutagenesis or other techniques to modify the properties of the antibodies. These modified genes may then be returned to the immortalized cells by transfection to provide for a continuous mammalian cellular source of the desired antibodies. The subject invention provides for a convenient source of human antibodies, where the human antibodies are produced in analogous manner to the production of antibodies in a human host. The animal host cells conveniently provide for the activation and rearrangement of human DNA in the host cells for production of human antibodies.

In accordance with the subject invention, human antibodies can be produced to human immunogens, eg. proteins, by immunization of the subject host mammal with human immunogens. The resulting antisera will be specific for the human immunogen and may be harvested from the serum of the host. The immunized host B cells may be used for immortalization, eg. myeloma cell fusion, transfection, etc. to provide immortal cells, eg. hybridomas, to produce monoclonal antibodies. The antibodies, antiserum and monoclonal antibodies will be glycosylated in accordance with the species of the cell producing the antibodies. Rare variable regions of the Ig locus may be recruited in producing the antibodies, so that antibodies having rare variable regions may be obtained.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A mouse embryonic stem cell with at least one inactivated endogenous immunoglobulin heavy chain locus in which all of the J segment genes are deleted to prevent rearrangement of the locus and to prevent formation of a transcript of a rearranged immunoglobulin heavy chain locus, said inactivated endogenous locus comprising a gene encoding a selectable marker.

2. The mouse embryonic stem cell according to claim 1, wherein said gene encoding a selectable marker is selected from the group consisting of: a neomycin resistance gene; an acyclovir resistance gene and a gancyclovir resistance gene.

3. A transgenic mouse wherein the germ cells comprise at least one inactivated endogenous immunoglobulin heavy chain locus in which all of the J segment genes are deleted to prevent rearrangement and to prevent formation of a transcript of a rearranged locus and the expression of an endogenous immunoglobulin heavy chain from the inactivated locus.

4. A transgenic mouse or the progeny thereof, wherein the somatic and germ cells comprise at least one inactivated endogenous immunoglobulin heavy chain locus in which all of the J segment genes are deleted to prevent rearrangement and to prevent formation of a transcript of a rearranged locus and the expression of an endogenous immunoglobulin heavy chain from the inactivated locus.

5. A transgenic mouse or the progeny thereof, wherein the somatic and germ cells comprise inactivated endogenous immunoglobulin loci in which all of the J segment genes are deleted to prevent rearrangement and to prevent formation of a transcript of a rearranged locus, wherein the transgenic mouse and progeny lack expression of endogenous immunoglobulin heavy chains.

* * * * *

SEQUENCE LISTING

<160> NUMBER OF SEQ ID NOS: 27

<210> SEQ ID NO 1
<211> LENGTH: 24
<212> TYPE: DNA
<213> ORGANISM: Artificial Sequence
<220> FEATURE:
<223> OTHER INFORMATION: Description of Artificial Sequence: priming
      oligonucleotide

<400> SEQUENCE: 1
tggcggaccg ctatccccca ggac                                              24

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: priming
      oligonucleotide

<400> SEQUENCE: 2
tagcctgggt ccctccttac                                                   20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: priming
      oligonucleotide

<400> SEQUENCE: 3
acggtatcgc cgctcccgat                                                   20

<210> SEQ ID NO 4
<211> LENGTH: 23
<212> TYPE: DNA
<213> ORGANISM: Artificial Sequence
<220> FEATURE:
<223> OTHER INFORMATION: Description of Artificial Sequence: priming
      oligonucleotide

<400> SEQUENCE: 4
agtcactgta aagacttcgg gta                                               23

<210> SEQ ID NO 5
<211> LENGTH: 56
<212> TYPE: DNA
<213> ORGANISM: Artificial Sequence
<220> FEATURE:
<223> OTHER INFORMATION: Description of Artificial Sequence: synthetic
      polylinker

<400> SEQUENCE: 5
gcatatgcct gaggtaagca tgcggtaccg aattctataa gcttgcggcc gcagct           56

<210> SEQ ID NO 6
<211> LENGTH: 56
<212> TYPE: DNA
<213> ORGANISM: Artificial Sequence
<220> FEATURE:
<223> OTHER INFORMATION: Description of Artificial Sequence: synthetic
      polylinker

<400> SEQUENCE: 6
gcggccgcaa gcttatagaa ttcggtaccg catgcttacc tcaggcatat gcgtac          56

<210> SEQ ID NO 7
<211> LENGTH: 32
<212> TYPE: DNA
<213> ORGANISM: Artificial Sequence
<220> FEATURE:
<223> OTHER INFORMATION: Description of Artificial Sequence: adapter

<400> SEQUENCE: 7
agctggaacc ccttgccctt ggggaacgcc gg                                   32

<210> SEQ ID NO 8
<211> LENGTH: 47
<212> TYPE: DNA
<213> ORGANISM: Artificial Sequence
<220> FEATURE:
<223> OTHER INFORMATION: Description of Artificial Sequence: synthetic
      polylinker

<400> SEQUENCE: 8
gagctcggat cctatctcga ggaattctat aagcttcata tgtagct                   47

<210> SEQ ID NO 9
<211> LENGTH: 47
<212> TYPE: DNA
<213> ORGANISM: Artificial Sequence
<220> FEATURE:
<223> OTHER INFORMATION: Description of Artificial Sequence: synthetic
      polylinker

<400> SEQUENCE: 9
acatatgaag cttatagaat tcctcgagat aggatccgag ctcgtac                   47

<210> SEQ ID NO 10
<211> LENGTH: 50
<212> TYPE: DNA
<213> ORGANISM: Artificial Sequence
<220> FEATURE:
<223> OTHER INFORMATION: Description of Artificial Sequence: synthetic
      polylinker

<400> SEQUENCE: 10
aagcttatag aattcggtac ctggatcctg agctcatagc ggccgcagct                50

<210> SEQ ID NO 11
<211> LENGTH: 50
<212> TYPE: DNA
<213> ORGANISM: Artificial Sequence
<220> FEATURE:
<223> OTHER INFORMATION: Description of Artificial Sequence: synthetic
      polylinker

<400> SEQUENCE: 11
gcggccgcta tgagctcagg atccaggtac cgaattctat aagcttgtac                50

<210> SEQ ID NO 12
<211> LENGTH: 13
<212> TYPE: DNA
<213> ORGANISM: Artificial Sequence
<220> FEATURE:
<223> OTHER INFORMATION: Description of Artificial Sequence: adapter

<400> SEQUENCE: 12
gggaagccgc cgc                                                        13

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: adapter

<400> SEQUENCE: 13
catggcggcg gcttccctgc a                                                   21

<210> SEQ ID NO 14
<211> LENGTH: 26
<212> TYPE: DNA
<213> ORGANISM: Artificial Sequence
<220> FEATURE:
<223> OTHER INFORMATION: Description of Artificial Sequence: primer

<400> SEQUENCE: 14
caggatccag ctgtgccttc tagttg                                              26

<210> SEQ ID NO 15
<211> LENGTH: 30
<212> TYPE: DNA
<213> ORGANISM: Artificial Sequence
<220> FEATURE:
<223> OTHER INFORMATION: Description of Artificial Sequence: primer

<400> SEQUENCE: 15
ctgagctcta gacccataga gcccaccgca                                          30

<210> SEQ ID NO 16
<211> LENGTH: 16
<212> TYPE: DNA
<213> ORGANISM: Artificial Sequence
<220> FEATURE:
<223> OTHER INFORMATION: Description of Artificial Sequence: adapter

<400> SEQUENCE: 16
agctggaacc ccttgc                                                         16

<210> SEQ ID NO 17
<211> LENGTH: 16
<212> TYPE: DNA
<213> ORGANISM: Artificial Sequence
<220> FEATURE:
<223> OTHER INFORMATION: Description of Artificial Sequence: adapter

<400> SEQUENCE: 17
ggccgcaagg ggttcc                                                         16

<210> SEQ ID NO 18
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 18
gcagagcctg ctgaattctg gctg                                                24

<210> SEQ ID NO 19
<211> LENGTH: 22
<212> TYPE: DNA
<213> ORGANISM: Artificial Sequence
<220> FEATURE:
<223> OTHER INFORMATION: Description of Artificial Sequence: primer

```
<400> SEQUENCE: 19
gtaatacaca gccgtgtcct gg                                          22

<210> SEQ ID NO 20
<211> LENGTH: 23
<212> TYPE: DNA
<213> ORGANISM: Artificial Sequence
<220> FEATURE:
<223> OTHER INFORMATION: Description of Artificial Sequence: primer

<400> SEQUENCE: 20
ttccggcccc gatgcgggac tgc                                         23

<210> SEQ ID NO 21
<211> LENGTH: 15
<212> TYPE: DNA
<213> ORGANISM: Artificial Sequence
<220> FEATURE:
<223> OTHER INFORMATION: Description of Artificial Sequence: primer

<400> SEQUENCE: 21
cctctcccta agact                                                  15

<210> SEQ ID NO 22
<211> LENGTH: 18
<212> TYPE: DNA
<213> ORGANISM: Artificial Sequence
<220> FEATURE:
<223> OTHER INFORMATION: Description of Artificial Sequence: primer

<400> SEQUENCE: 22
caaaggataa cagccctg                                               18

<210> SEQ ID NO 23
<211> LENGTH: 18
<212> TYPE: DNA
<213> ORGANISM: Artificial Sequence
<220> FEATURE:
<223> OTHER INFORMATION: Description of Artificial Sequence: primer

<400> SEQUENCE: 23
agctggctgc ttgtcatg                                               18

<210> SEQ ID NO 24
<211> LENGTH: 21
<212> TYPE: DNA
<213> ORGANISM: Artificial Sequence
<220> FEATURE:
<223> OTHER INFORMATION: Description of Artificial Sequence: priming
      oligonucleotide

<400> SEQUENCE: 24
ttctcggagc actgtccgac c                                           21

<210> SEQ ID NO 25
<211> LENGTH: 27
<212> TYPE: DNA
<213> ORGANISM: Artificial Sequence
<220> FEATURE:
<223> OTHER INFORMATION: Description of Artificial Sequence: priming
      oligonucleotide

<400> SEQUENCE: 25
cttgcgcctt aaaccaactt ggtaccg                                     27
```

```
<210> SEQ ID NO 26
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 26
gtatgtggag cataaccgga g                                           21

<210> SEQ ID NO 27
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 27
caggttttgt ctctaacgtg g                                           21
```